US008617884B2

(12) United States Patent
Berenson et al.

(10) Patent No.: US 8,617,884 B2
(45) Date of Patent: Dec. 31, 2013

(54) METHODS FOR ELIMINATING AT LEAST A SUBSTANTIAL PORTION OF A CLONAL ANTIGEN-SPECIFIC MEMORY T CELL SUBPOPULATION

(75) Inventors: Ronald J Berenson, Mercer Island, WA (US); Mark Bonyhadi, Sammamish, WA (US); Dale Kalamasz, Redmond, WA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 12/324,593

(22) Filed: Nov. 26, 2008

(65) Prior Publication Data

US 2009/0148404 A1 Jun. 11, 2009

Related U.S. Application Data

(63) Continuation of application No. 10/900,046, filed on Jul. 27, 2004, now abandoned, which is a continuation-in-part of application No. 10/729,822, filed on Dec. 5, 2003, now abandoned, which is a continuation of application No. 10/603,577, filed on Jun. 24, 2003, now abandoned.

(60) Provisional application No. 60/442,001, filed on Jan. 22, 2003.

(51) Int. Cl.
C12N 5/00 (2006.01)
(52) U.S. Cl.
USPC ......... 435/375; 435/377; 435/325; 435/372.3
(58) Field of Classification Search
None
See application file for complete search history.

(56) References Cited

U.S. PATENT DOCUMENTS

| | | | |
|---|---|---|---|
| 5,081,029 A | 1/1992 | Zarling et al. | 435/172.3 |
| 5,106,746 A | 4/1992 | Ho | 435/240.25 |
| 5,190,878 A | 3/1993 | Wilhelm | 435/285 |
| 5,223,426 A | 6/1993 | Skibbens et al. | 435/240.27 |
| 5,260,422 A | 11/1993 | Clark et al. | 530/403 |
| 5,443,983 A | 8/1995 | Ochoa et al. | 435/240.2 |
| 5,468,635 A | 11/1995 | Komiya et al. | 435/240.21 |
| 5,470,730 A | 11/1995 | Greenberg et al. | 435/172.3 |
| 5,635,354 A | 6/1997 | Kourilsky et al. | 435/6 |
| 5,674,704 A | 10/1997 | Goodwin et al. | |
| 5,677,139 A | 10/1997 | Johnson et al. | 435/29 |
| 5,688,915 A | 11/1997 | Ron et al. | 530/380 |
| 5,728,388 A | 3/1998 | Terman | 424/237.1 |
| 5,735,279 A | 4/1998 | Klaveness et al. | 128/654 |
| 5,738,852 A | 4/1998 | Robinson et al. | 424/199.1 |
| 5,759,546 A | 6/1998 | Weinberg et al. | 424/179.1 |
| 5,766,947 A | 6/1998 | Rittershaus et al. | 435/334 |
| 5,773,573 A | 6/1998 | Holms | 530/327 |
| 5,776,966 A | 7/1998 | North | 514/410 |
| 5,804,442 A | 9/1998 | Romet-Lemonne et al. | 435/374 |
| 5,824,551 A | 10/1998 | Damme et al. | 435/375 |
| 5,827,642 A | 10/1998 | Riddell et al. | 435/2 |
| 5,830,462 A | 11/1998 | Crabtree et al. | 424/93.21 |
| 5,830,473 A | 11/1998 | Thierfelder | 424/172.1 |
| 5,837,447 A | 11/1998 | Gorski | 435/6 |
| 5,837,477 A | 11/1998 | Germain et al. | 435/7.24 |
| 5,843,435 A | 12/1998 | Slavin | 424/93.71 |
| 5,843,635 A | 12/1998 | Schlossman et al. | 435/5 |
| 5,858,358 A | 1/1999 | June et al. | 424/130.1 |
| 5,869,270 A | 2/1999 | Rhode et al. | 435/7.24 |
| 5,869,337 A | 2/1999 | Crabtree et al. | 435/372.3 |
| 5,871,753 A | 2/1999 | Crabtree et al. | 424/280.1 |
| 5,872,222 A | 2/1999 | Chang | 530/391.1 |
| 5,883,223 A | 3/1999 | Gray | 530/328 |
| 5,888,511 A | 3/1999 | Skurkovich et al. | 424/145.1 |
| 5,888,807 A | 3/1999 | Palsson et al. | 435/293.2 |
| 5,910,403 A | 6/1999 | Hellerstein | 435/4 |
| 5,928,639 A | 7/1999 | Slavin | 424/93.71 |
| 5,935,575 A | 8/1999 | Lenardo et al. | 424/184.1 |
| 5,942,607 A | 8/1999 | Freeman et al. | 536/23.5 |
| 5,962,319 A | 10/1999 | Ogawa et al. | 435/325 |
| 5,962,320 A | 10/1999 | Robinson | 435/366 |
| 5,976,533 A | 11/1999 | Skibbens et al. | 424/144.1 |
| 5,980,892 A | 11/1999 | Skibbens et al. | 424/144.1 |
| 5,985,552 A | 11/1999 | Howell et al. | 435/6 |
| 5,985,653 A | 11/1999 | Armstrong et al. | 435/303.1 |
| 5,989,546 A | 11/1999 | Lenardo | 424/184.1 |
| 6,004,942 A | 12/1999 | Firestein et al. | 514/44 |
| 6,010,902 A | 1/2000 | Ledbetter et al. | 435/328 |
| 6,011,018 A | 1/2000 | Crabtree et al. | 514/31 |

(Continued)

FOREIGN PATENT DOCUMENTS

| | | |
|---|---|---|
| CA | 2304268 A1 | 4/1999 |
| EP | 242216 A1 | 10/1987 |

(Continued)

OTHER PUBLICATIONS

Allegretta et al., "Homologies between T Cell Receptor Junctional Sequences Unique to Multiple Sclerosis and T Cells Mediating Experimental Allergic Encephalomyelitis," *The Journal of Clinical Investigation* 94:105-109, Jul. 1994.

Anderton et al., "Therapeutic potential of TCR antagonists is determined by their ability to modulate a diverse repertoire of autoreactive T cells," *Eur. J. Immunol.* 29(6):1850-1857, Jun. 1999.

Arenz et al., "Antigen-independent in vitro expansion of T cells does not affect the T cell receptor Vβ repertoire," *J. Mol. Med.* 75:678-686, 1997.

Azuma et al., "Induction of apoptosis of activated murine splenic T cells by cycloprodigiosin hydrochloride, a novel immunosuppressant," *Immunopharmacology* 46(1):29-37, Jan. 2000.

Baroja et al., "The Anti-T Cell Monoclonal Antibody 9.3 (Anti-CD28) Provides a Helper Signal and Bypasses the Need for Accessory Cells in T Cell Activation with Immobilized Anti-CD3 and Mitogens," *Cellular Immunology* 120:205-217, 1989.

(Continued)

*Primary Examiner* — Michail Belyavskyi

(57) ABSTRACT

The present invention relates generally to methods for stimulating T cells, and more particularly, to methods to eliminate undesired (e.g., autoreactive, alloreactive, pathogenic) subpopulations of T cells from a mixed population of T cells, thereby restoring the normal immune repertoire of said T cells. The present invention also relates to compositions of cells, including stimulated T cells having restored immune repertoire and uses thereof.

6 Claims, 17 Drawing Sheets

(56) References Cited

U.S. PATENT DOCUMENTS

| | | | |
|---|---|---|---|
| 6,040,177 A | 3/2000 | Riddell et al. | 435/372.3 |
| 6,043,082 A | 3/2000 | Crabtree et al. | 435/320.1 |
| 6,046,047 A | 4/2000 | Crabtree et al. | 435/320.1 |
| 6,048,526 A | 4/2000 | Skibbens et al. | 424/144.1 |
| 6,056,951 A | 5/2000 | Torres | 424/93.1 |
| 6,063,625 A | 5/2000 | Crabtree et al. | 435/375 |
| 6,083,503 A | 7/2000 | Lenardo | 424/184.1 |
| 6,090,387 A | 7/2000 | Howell et al. | 424/185.1 |
| 6,096,532 A | 8/2000 | Armstrong et al. | 435/286.5 |
| 6,113,901 A | 9/2000 | Bluestone | 424/154.1 |
| 6,117,982 A | 9/2000 | Chang | 530/391.1 |
| 6,126,945 A | 10/2000 | Terman et al. | 424/237.1 |
| 6,129,916 A | 10/2000 | Chang | 424/179.1 |
| 6,140,120 A | 10/2000 | Crabtree et al. | 435/372.3 |
| 6,143,291 A | 11/2000 | June et al. | 424/93.21 |
| 6,143,292 A | 11/2000 | Slavin | 424/93.7 |
| 6,143,297 A | 11/2000 | Bluestone | 424/184.1 |
| 6,165,787 A | 12/2000 | Crabtree et al. | 435/372.3 |
| 6,171,799 B1 | 1/2001 | Skibbens et al. | 435/7.1 |
| 6,180,097 B1 | 1/2001 | Terman | 424/93.1 |
| 6,197,298 B1 | 3/2001 | Chang | 424/179.1 |
| 6,210,669 B1 | 4/2001 | Aruffo et al. | 424/144.1 |
| 6,221,351 B1 | 4/2001 | Terman | 424/93.71 |
| 6,221,352 B1 | 4/2001 | Howell et al. | 424/139.1 |
| 6,232,445 B1 | 5/2001 | Rhode et al. | 530/387.3 |
| 6,251,385 B1 | 6/2001 | Terman | 424/93.7 |
| 6,258,357 B1 | 7/2001 | Spaner | 424/93.71 |
| 6,284,879 B1 | 9/2001 | Faustman | 536/23.1 |
| 6,290,955 B1 | 9/2001 | Thierfelder | 424/130.1 |
| 6,309,645 B1 | 10/2001 | Rhode et al. | 424/192.1 |
| 6,316,257 B1 | 11/2001 | Flyer et al. | 435/372.3 |
| 6,333,032 B1 | 12/2001 | Skurkovich et al. | 424/130.1 |
| 6,338,845 B1 | 1/2002 | Terman | 424/93.1 |
| 6,340,461 B1 | 1/2002 | Terman | 424/193.1 |
| 6,352,694 B1 * | 3/2002 | June et al. | 424/93.71 |
| 6,355,779 B1 | 3/2002 | Goodwin et al. | 530/388.23 |
| 6,399,054 B1 | 6/2002 | Casorati et al. | 424/93.21 |
| 6,406,699 B1 | 6/2002 | Wood | 424/184.1 |
| 6,461,806 B1 | 10/2002 | Hellerstein | 435/4 |
| 6,465,251 B1 | 10/2002 | Schultze et al. | 435/377 |
| 6,488,933 B2 | 12/2002 | Cohen et al. | 424/185.1 |
| 6,534,055 B1 | 3/2003 | June et al. | 424/93.71 |
| 6,566,082 B1 | 5/2003 | Weinberg et al. | 435/7.24 |
| 6,576,428 B1 | 6/2003 | Assenmacher et al. | 435/7.1 |
| 6,576,466 B2 | 6/2003 | Jungfer et al. | 435/372.3 |
| 6,602,709 B1 | 8/2003 | Albert et al. | 435/372 |
| 6,610,542 B1 | 8/2003 | Bell et al. | 435/377 |
| 6,656,471 B1 | 12/2003 | Sastry et al. | 424/188.1 |
| 6,689,605 B1 | 2/2004 | Mountz et al. | 435/320.1 |
| 6,692,746 B1 | 2/2004 | Terman et al. | 424/184.1 |
| 6,719,972 B1 | 4/2004 | Gribben et al. | 424/154.1 |
| 6,867,041 B2 * | 3/2005 | Berenson et al. | 435/377 |
| 6,887,466 B2 | 5/2005 | June et al. | 424/93.71 |
| 6,905,680 B2 | 6/2005 | June et al. | 424/93.71 |
| 6,905,874 B2 * | 6/2005 | Berenson et al. | 435/375 |
| 7,572,631 B2 * | 8/2009 | Berenson et al. | 435/375 |
| 2001/0012514 A1 | 8/2001 | Skurkovich et al. | 424/143.1 |
| 2001/0028879 A1 | 10/2001 | Spaner | 424/93.7 |
| 2001/0031253 A1 | 10/2001 | Gruenberg | 424/93.1 |
| 2001/0051151 A1 | 12/2001 | Lamb, Jr. | 424/93.7 |
| 2002/0004041 A1 | 1/2002 | Albert et al. | 424/93.21 |
| 2002/0006409 A1 | 1/2002 | Wood | 424/184.1 |
| 2002/0009448 A1 | 1/2002 | Weiner et al. | 424/154.1 |
| 2002/0031496 A1 | 3/2002 | Firestein et al. | 424/93.6 |
| 2002/0034513 A1 | 3/2002 | Rhode et al. | 424/184.1 |
| 2002/0034517 A1 | 3/2002 | Brasel et al. | 424/192.1 |
| 2002/0037860 A1 | 3/2002 | D'Andrea et al. | 514/19 |
| 2002/0039569 A1 | 4/2002 | Jungfer et al. | 424/85.2 |
| 2002/0058019 A1 | 5/2002 | Berenson et al. | 424/93.7 |
| 2002/0090362 A1 | 7/2002 | Stauss | 424/93.21 |
| 2002/0091079 A1 | 7/2002 | Rhode et al. | 514/12 |
| 2002/0119568 A1 | 8/2002 | Berenson et al. | 435/446 |
| 2002/0119571 A1 | 8/2002 | Ritter et al. | 435/456 |
| 2002/0123472 A1 | 9/2002 | Faustman | 514/44 |
| 2002/0146396 A1 | 10/2002 | Albert et al. | 424/93.21 |
| 2002/0164331 A1 | 11/2002 | Exley et al. | 424/144.1 |
| 2002/0176850 A1 | 11/2002 | Slavin | 424/93.21 |
| 2002/0177554 A1 | 11/2002 | Verheijden et al. | 514/12 |
| 2002/0182730 A1 | 12/2002 | Gruenberg | 435/375 |
| 2002/0197716 A1 | 12/2002 | Flyer et al. | 435/372 |
| 2003/0022210 A1 | 1/2003 | Bonyhadi et al. | 435/6 |
| 2003/0039650 A1 | 2/2003 | Gruenberg | 424/144.1 |
| 2003/0082806 A1 | 5/2003 | Berenson et al. | 435/372 |
| 2003/0113328 A1 | 6/2003 | Roifman et al. | 424/146.1 |
| 2003/0113341 A1 | 6/2003 | Lynch et al. | 424/185.1 |
| 2003/0118659 A1 | 6/2003 | August et al. | 424/491 |
| 2003/0119185 A1 | 6/2003 | Berenson et al. | 435/372 |
| 2003/0124122 A1 | 7/2003 | Berenson et al. | 424/144.1 |
| 2003/0134341 A1 | 7/2003 | Gruenberg | 435/7.21 |
| 2003/0134415 A1 | 7/2003 | Gruenberg | 435/372 |
| 2003/0165531 A1 | 9/2003 | Lynch et al. | 424/192.1 |
| 2003/0170238 A1 | 9/2003 | Gruenberg | 424/144.1 |
| 2003/0175242 A1 | 9/2003 | Gruenberg | 424/93.2 |
| 2003/0175272 A1 | 9/2003 | Gruenberg | 424/144.1 |
| 2003/0176378 A1 | 9/2003 | Weiner et al. | 514/44 |
| 2003/0190323 A1 | 10/2003 | Cohen et al. | 424/185.1 |
| 2003/0194395 A1 | 10/2003 | Gruenberg et al. | 424/93.7 |
| 2003/0219463 A1 | 11/2003 | Falkenburg et al. | 424/277.1 |
| 2003/0235908 A1 | 12/2003 | Berenson et al. | 435/372 |
| 2004/0005298 A1 | 1/2004 | Bonyhadi et al. | 424/93.7 |
| 2004/0023377 A1 | 2/2004 | Assenmacher et al. | 435/372 |
| 2004/0037845 A1 | 2/2004 | Brasel et al. | 424/185.1 |
| 2004/0072749 A1 | 4/2004 | Zochoer et al. | 514/12 |
| 2004/0151704 A1 | 8/2004 | Berenson et al. | 424/93.7 |
| 2004/0156860 A1 | 8/2004 | Weiner et al. | 424/185.1 |
| 2004/0157792 A1 | 8/2004 | Mountz et al. | 514/44 |
| 2004/0161433 A1 | 8/2004 | Teshigawara et al. | 424/277.1 |
| 2004/0180050 A1 | 9/2004 | Hoffman | 424/144.1 |
| 2004/0180808 A1 | 9/2004 | Nye et al. | 514/2 |
| 2004/0185048 A1 | 9/2004 | Strom et al. | 424/145.1 |
| 2004/0241162 A1 | 12/2004 | Berenson et al. | 424/144.1 |
| 2005/0084967 A1 | 4/2005 | Berenson et al. | 435/372 |
| 2005/0153447 A1 | 7/2005 | Berenson et al. | 435/372 |
| 2005/0214942 A1 | 9/2005 | Berenson et al. | 435/372 |
| 2005/0226857 A1 | 10/2005 | Bonyhadi et al. | 424/93.7 |
| 2006/0121005 A1 | 6/2006 | Berenson et al. | 424/93.7 |

FOREIGN PATENT DOCUMENTS

| | | |
|---|---|---|
| EP | 440373 B1 | 4/1997 |
| EP | 340109 B1 | 5/1997 |
| EP | 953351 A2 | 11/1999 |
| EP | 633930 B1 | 4/2000 |
| EP | 1241249 A1 | 9/2002 |
| WO | WO 86/04334 | 7/1986 |
| WO | WO 90/10449 | 9/1990 |
| WO | WO 91/15236 | 10/1991 |
| WO | WO 91/18629 | 12/1991 |
| WO | WO 92/06117 | 4/1992 |
| WO | WO 92/09628 | 6/1992 |
| WO | WO 93/02690 | 2/1993 |
| WO | WO 93/14789 | 8/1993 |
| WO | WO 93/19605 | 10/1993 |
| WO | WO 93/19767 | 10/1993 |
| WO | WO 93/24127 | 12/1993 |
| WO | WO 93/24136 | 12/1993 |
| WO | WO 94/02156 | 2/1994 |
| WO | WO 94/03202 | 2/1994 |
| WO | WO 94/12196 | 6/1994 |
| WO | WO 94/18317 | 8/1994 |
| WO | WO 94/19009 | 9/1994 |
| WO | WO 94/23734 | 10/1994 |
| WO | WO 94/28912 | 12/1994 |
| WO | WO 94/28926 | 12/1994 |
| WO | WO 95/09652 | 4/1995 |
| WO | WO 95/13082 | 5/1995 |
| WO | WO 95/20649 | 8/1995 |
| WO | WO 95/21251 | 8/1995 |
| WO | WO 95/24910 | 9/1995 |
| WO | WO 95/32735 | 12/1995 |
| WO | WO 95/33770 | 12/1995 |
| WO | WO 95/33823 | 12/1995 |
| WO | WO 96/06929 | 3/1996 |
| WO | WO 96/14874 | 5/1996 |

(56) References Cited

FOREIGN PATENT DOCUMENTS

| | | |
|---|---|---|
| WO | WO 96/15153 | 5/1996 |
| WO | WO 96/33265 | 10/1996 |
| WO | WO 96/34622 | 11/1996 |
| WO | WO 96/37208 | 11/1996 |
| WO | WO 96/38158 | 12/1996 |
| WO | WO 97/00270 | 1/1997 |
| WO | WO 97/01304 | 1/1997 |
| WO | WO 97/02016 | 1/1997 |
| WO | WO 97/02045 | 1/1997 |
| WO | WO 97/05233 | 2/1997 |
| WO | WO 97/05239 | 2/1997 |
| WO | WO 97/10361 | 3/1997 |
| WO | WO 97/12633 | 4/1997 |
| WO | WO 97/32970 | 9/1997 |
| WO | WO 97/37004 | 10/1997 |
| WO | WO 97/39722 | 10/1997 |
| WO | WO 97/44667 | 11/1997 |
| WO | WO 98/21314 | 5/1998 |
| WO | WO 98/33891 | 8/1998 |
| WO | WO 98/41090 | 9/1998 |
| WO | WO 98/51820 | 11/1998 |
| WO | WO 98/52615 | 11/1998 |
| WO | WO 98/56819 | 12/1998 |
| WO | WO 98/56823 | 12/1998 |
| WO | WO 98/58541 | 12/1998 |
| WO | WO 99/00143 | 1/1999 |
| WO | WO 99/13904 | 3/1999 |
| WO | WO 99/21572 | 5/1999 |
| WO | WO 99/21576 | 5/1999 |
| WO | WO 99/29883 | 6/1999 |
| WO | WO 99/38953 | 8/1999 |
| WO | WO 99/51247 | 10/1999 |
| WO | WO 99/52928 | 10/1999 |
| WO | WO 99/55843 | 11/1999 |
| WO | WO 99/58977 | 11/1999 |
| WO | WO 00/02520 | 1/2000 |
| WO | WO 00/06588 | 2/2000 |
| WO | WO 00/15767 | 3/2000 |
| WO | WO 00/22124 | 4/2000 |
| WO | WO 00/29008 | 5/2000 |
| WO | WO 00/31138 | 6/2000 |
| WO | WO 00/44893 | 8/2000 |
| WO | WO 00/51432 | 9/2000 |
| WO | WO 00/52046 | 9/2000 |
| WO | WO 00/53209 | 9/2000 |
| WO | WO 00/56356 | 9/2000 |
| WO | WO 00/59538 | 10/2000 |
| WO | WO 00/66764 | 11/2000 |
| WO | WO 01/22970 | 4/2001 |
| WO | WO 01/24771 | 4/2001 |
| WO | WO 01/29192 | 4/2001 |
| WO | WO 01/43694 | 6/2001 |
| WO | WO 01/43695 | 6/2001 |
| WO | WO 01/49743 | 7/2001 |
| WO | WO 01/52664 | 7/2001 |
| WO | WO 01/70938 | 9/2001 |
| WO | WO 01/87333 | 11/2001 |
| WO | WO 01/88116 | 11/2001 |
| WO | WO 01/88159 | 11/2001 |
| WO | WO 01/98357 | 12/2001 |
| WO | WO 02/09674 | 2/2002 |
| WO | WO 02/16414 | 2/2002 |
| WO | WO 02/22790 | 3/2002 |
| WO | WO 02/22805 | 3/2002 |
| WO | WO 02/28385 | 4/2002 |
| WO | WO 02/060376 | 8/2002 |
| WO | WO 02/087627 | 11/2002 |
| WO | WO 03/020904 | 3/2003 |
| WO | WO 03/024312 | 3/2003 |
| WO | WO 03/024989 | 3/2003 |
| WO | WO 03/025158 | 3/2003 |
| WO | WO 03/034820 | 5/2003 |
| WO | WO 03/043643 | 5/2003 |
| WO | WO 03/067221 | 8/2003 |
| WO | WO 03/077658 | 9/2003 |

OTHER PUBLICATIONS

Bender et al., "T Cell Receptor Repertoire in Polymyositis: Clonal Expansion of Autoaggressive CD8$^+$ T Cells," *J. Exp. Med.* 181:1863-1868, May 1995.

Berge et al., "Selective Expansion of a Peripheral Blood CD8$^+$ Memory T Cell Subset Expressing Both Granzyme B and L-Selectin During Primary Viral Infection in Renal Allograft Recipients," Transplantation Proceedings 30:3975-3977, 1988.

Bergstresser et al., "T Cell-Mediated Terminal Maturation of Dendritic Cells," in *Dendritic Cell in Fundamental and Clinical Immunology*, Ricciardi-Castognoli (Ed.), Plenum Press, New York, 1997, pp. 65-69.

Bierer et al., "Cyclosporin A and FK506: Molecular Mechanisms of Immunosuppression and Probes for Transplantation Biology," *Curr. Opin. Immun.* 5(5):763-773, 1993.

Bishop et al., "Assessing Apoptosis in Developing T Cells by Flow Cytometry" in *Methods in Molecular Biology*, vol. 134: *T Cell Protocols: Development and Activation*, Kearse, K.P. ed., Humana Press, 1999, pp. 117-131.

Boehncke et al., "T-Cell-Receptor Repertoire in Chronic Plaque-Stage Psoriasis Is Restricted and Lacks Enrichment of Superantigen-Associated Vβ Regions," *J. Invest. Dermatol.* 104:725-728, 1995.

Bonyhadi et al., "Xcellearate: An Autologous T Cell Immunotherapy Approach for Treating B-Cell Lymphocytic Leukemia (B-CLL)," in *Proceedings of the 42$^{nd}$ Annual Meeting of the American Society of Hematology*, San Francisco, Dec. 1-5, 2000, vol. 96, No. 11, part 1, Abstract # 3616.

Bonyhadi et al., "Expansion of Antigen-Specific CTL Using CD3/CD28 Paramagnetic Microbeads Xcellerate™ Beads) for Adoptive Cellular Therapy of Melanoma," *Blood* 98(11):32b-33b, Abstract No. 3728, 2001.

Borthwick et al., "Loss of CD28 expression on CD8$^+$ T cells is induced by IL-2 receptor γ chain signaling cytokines and type I IFN, and increases susceptibility to activation-induced apoptosis," *International Immunology* 12(7):1005-1013, 2000.

Bour et al., "T-Cell Repertoire Analysis in Chronic Plaque Psoriasis Suggests an Antigen-Specific Immune Response," *Human Immunology* 60:665-676, 1999.

Bretscher, "The Two-Signal Model of Lymphocyte Activation Twenty-One Years Later," *Immunology Today* 13(2):74-76, 1992.

Broomé et al., "Preferential Vβ3 usage by hepatic T lymphocyteds in patients with primary sclerosing cholangitis," *Journal of Hepatology* 26:527-534, 1997.

Bruserud et al., "Cyclosporine A and FK506 Show Similar Immunosuppressive Effects on Long-term in Vitro T-Cell Proliferation," *Int. J. Immunopharmac.* 15(2):93-97, 1993.

Bulfone-Paus et al., "An interleukin-2-IgG-Fas ligand fusion protein suppresses delayed-type hypersensitivity in mice by triggering apoptosis in activated T cells as a novel strategy for immunosuppression," *Transplantation* 69(7):1386-1391, Apr. 2000.

Carlens et al., "Ex vivo T lymphocyte expansion for retroviral transduction: Influence of serum-free media on variations in cell expansion rates and lymphocyte subset distribution," *Experimental Hematology* 28:1137-1146, 2000.

Carpenter et al., "Non-Fc receptor-binding humanized anti-CD3 antibodies induce apoptosis of activated human T cells," *J. Immunol.* 165(11):6205-6213, Dec. 2000.

Carpenter et al., "Non-FcR-binding, humanized anti-CD3 antibody Hu291 induces apoptosis of human T cells more effectively than OKT3 and is immunosuppressive in vivo," *Transplant Proc.* 32(7):1545-1546, Nov. 2000.

Carroll et al., "Accelerating the induction of Fas-mediated T cell apoptosis: a strategy for transplant tolerance?," *Clin. Exp. Immunol.* 126(3):589-597, Dec. 2001.

Christen et al., "Apoptosis of Autoreactive CD8 Lymphocytes as a Potential Mechanism for the Abrogation of Type 1 Diabetes by Islet-Specific TNF-α Expression at a Time When the Autoimmune Process Is Already Ongoing," *Ann. N.Y. Acad. Sci.* 958:166-169, 2002.

Cioca et al., "Apoptosis of peripheral blood lymphocytes is induced by catecholamines," *Jpn. Heart J.* 41(3):385-398, May 2000.

Claret et al., "Characterization of T Cell Repertoire in Patients with Graft-Versus-Leukemia After Donor Lymphocyte Infusion," *Journal of Clinical Investigation* 100(4):855-866, Aug. 1997.

(56) References Cited

OTHER PUBLICATIONS

Cohen et al., "Propagation of Mouse and Human T Cells with Defined Antigen Specificity and Function," *CIBA Foundation Symp.* 187:179-197, 1994.
Cohen et al., "T-Cell Adoptive Therapy of Tumors: Mechanisms of Improved Therapeutic Performance," *Critical Reviews in Immunology* 21:215-248, 2001.
Combadière et al., "Selective Induction of Apoptosis in Mature T Lymphocytes by Variant T Cell Receptor Ligands," *Journal of Experimental Medicine* 187(3):349-355, Feb. 2, 1998.
Creson et al., "The Mode and Duration of Anti-CD28 Costimulation Determine Resistance to Infection by Macrophage-Tropic Strains of Human Immunodeficiency Virus Type 1 in Vitro," *Journal of Virology* 73(11):9337-9347, Nov. 1999.
Dao et al., "Natural Human Interferon-α Augments Apoptosis in Activated T Cell Line," *Cellular Immunology* 155:304-311, 1994.
Davey et al., "TCRB Clonotypes Are Present in CD4+ T Cell Populations Prepared Directly from Rheumatoid Synovium," *Human Immunology* 55:11-21, 1997.
Davies, "A new role for methimazole in autoimmune thyroid disease: inducing T cell apoptosis," *Thyroid* 10(7):525-526, Jul. 2000.
Di Renzo et al., "Enhanced apoptosis of T cells in common variable immunodeficiency (CVID): role of defective CD28 co-stimulation," *Clin. Exp. Immunol.* 120:503-511, 2000.
Di Sabatino et al., "Apoptosis and peripheral blood lymphocyte depletion in celiac disease," *Immunology* 103:435-440, 2001.
Dietrich et al., "TCR analysis reveals significant repertoire selection during in vitro lymphocyte culture," *International Immunology* 9(8):1073-1083, 1997.
Ebata et al., "Rapid induction of CD95 ligand and CD4+ T cell-mediated apoptosis by CD137 (41BB) costimulation," *Eur. J. Immunol.* 31(5):1410-1416, May 2001.
Ebert et al., "Lymphocyte apoptosis: induction by gene transfer techniques," *Gene Therapy* 4:296-302, 1997.
Epperson et al., "Oligoclonal T cell expansion in myelodysplastic syndrome: evidence for an autoimmune process," *Leukemia Research* 25:1075-1083, 2001.
Fishman-Lobell et al., "CD4 mAb induced apoptosis of peripheral T cells: multiparameter subpopulation analysis by flow cytometry using Attractors," *J. Immunol. Methods* 257(1-2):71-82, Nov. 2001.
Fowler et al., "Donor CD4-Enriched Cell of Th2 Cytokine Phenotype Regulate Graft Versus-Host Disease without Impairing Allogeneic Engraftment in Sublethally Irradiated Mice," *Blood* 87(10):3540-3549, 1994.
Friedman et al., "Repertoire Analysis of CD8+ T Cell Responses to Minor Histocompatibility Antigens Involved in Graft-Versus-Host Disease," *The Journal of Immunology* 161:41-48, 1998.
Fukumoto et al., "Activation-induced apoptosis of peripheral lymphocytes treated with 7-hydroxystaurosporine, UCN-01," *Investigational New Drugs* 17:335-341, 1999.
Fuss et al., "Anti-Interleukin 12 Treatment Regulates Apoptosis of Th1 T Cells in Experimental Colitits in Mice," *Gastroenterology* 117:1078-1088, 1999.
Fyhr et al., "T cell receptor β-chain repertoire in inclusion body myositis," *Journal of Neuroimmunology* 91:129-134, 1998.
Garland et al., "The Use of Teflon Cell Culture Bags to Expand Functionally Active CD8+ Cytotoxic T Lymphocytes," *J. Immunol. Meth.* 227(1-2):53-63, 1999.
Goronzy et al., "Thymic function and peripheral T-cell homeostasis in rheumatoid arthritis," *Trends in Immunology* 22(5):251-255, May 2001.
Goronzy et al., "T Cell Receptor Repertoire in Rheumatoid Arthritis," *Intern. Rev. Immunol.* 17:339-363, 1998.
Greer et al., "T Cell and NK Cell Lymphoproliferative Disorders," *Hematology Am Soc Hematol Educ Program.* 2001:259-81.
Groh et al., "Stimulation of T cell autoreactivity by anomalous expression of NKG2D and its MIC ligands in rheumatoid arthritis," *Proceedings of the National Academy of Sciences* 100(16):9452-9457, Aug. 5, 2003.
Haanen et al., "Selective Expansion of Cross-Reactive CD8+ Memory T Cells by Viral Variants," *J. Exp. Med.* 190(9):1319-1328, Nov. 1999.
Haegert et al., "Does a shift in the T-cell receptor repertoire precede the onset of MS," *Neurology* 53:485-490, 1999.
Hall et al., "TCRβ spectratyping in RA: evidence of clonal expansions in peripheral blood lymphocytes," *Ann. Rheum. Dis.* 57:319-322, 1998.
Hami et al., "Xcellerate™: A Platform Process for the GMP Manufacture of Activated T Cells for the Treatment of Patients with Cancer and Immune Dysfunction," in *Proceedings of the 42nd Annual Meeting of the American Society of Hematology*, San Francisco, Dec. 1-5, 2000, vol. 96, No. 11, part 1, abstract # 3630.
Hashimoto et al., "Novel immunosuppressive effect of FK506 by augmentation of T cell apoptosis," *Clinical Exp. Immunol.* 125(1):19-24, Jul. 2001.
Hayashi et al., "Implications of altered apoptosis in diabetes mellitus and autoimmune disease," *Apoptosis* 6(1/2):31-45, 2001.
Heimfeld et al., "Improvements in Gene Therapy: Rapid Purification of Specific Target Cells Using the CEPRATE® System," *British Journal of Haematology* 87(1):193, Abstract No. 754, 1994.
Henderson et al., "Comparison of the Effects of Fk-506, Cyclosporin A and Rapamycin on IL-2 Production," *Immunology* 73(3):316-321, Jul. 1991.
Hildeman et al., "Reactive Oxygen Species Regulate Activation-Induced T Cell Apoptosis," *Immunity* 10:735-744, Jun. 1999.
Holbrook et al., "Restrictions of T cell receptor β chain repertoire in the peripheral blood of patients with systemic lupus erythematosus," *Ann. Rheum. Dis.* 55:627-631, 1996.
Holtzman et al., "Regulation of T cell apoptosis," *Apoptosis* 5(5):459-471, 2000.
Husebekk et al., "Selection and expansion of T cells from untreated patients with CLL: source of cells for immune reconstitution," *Cytotherapy* 2(3):187-193, 2000.
Iezzi et al., "The Duration of Antigenic Stimulation Determines the Fate of Naive and Effector T Cells," *Immunity* 8:89-95, Jan. 1998.
Inada et al., "T Cell Repertoire in the Liver of Patients with Primary Biliary Cirrhosis," *Human Immunology* 61:675-683, 2000.
Ino et al., "Activation-induced T cell apoptosis by monocytes from stem cell products," *International Immunopharmacology* 1:1307-1319, 2001.
Jason et al., "The Effects of Mitogens, IL-2 and Anti-CD3 Antibody on the T-Cell Receptor VE3 Repertoire," *Scand. J. Immunol* 43:652-661, 1996.
June et al., "The B7 and CD28 Receptor Families," *Immunology Today* 15(7):321-331, 1994.
Kalamasz et al., "Storage Shipment of Freshly Harvested or Cryopreserved Xcellerate™ Activated T Cells for Clinical Applications," in *Proceedings of the 42nd Annual Meeting of the American Society of Hematology*, San Francisco, Dec. 1-5, 2000, vol. 96, No. 11, part 2, abstract # 5113.
Kallan et al., "Th1-like Cytokine Production Profile and Individual Specific Alterations in TCRBV-gene Usage of T Cells from Newly Diagnosed Type 1 Diabetes Patients after Stimulation with β-cell Antigens," *Journal of Autoimmunity* 10(6): 589-598, 1997.
Kang et al., "Clonal Expansion of Infiltrating T Cells in the Spinal Cords of SJL/J Mice Infected with Theiler's Virus," *The Journal of Immunology* 165:583-590, 2000.
Karadimitris et al., "Abnormal T-cell repertoire is consistent with immune process underlying the pathogenesis of paroxysmal nocturnal hemoglobinuria," *Blood* 96:2613-2620, 2000.
Kato et al., "Gene Transfer of CD40-Ligand Induces Autologous Immune Recognition of Chronic Lymphocytic Leukemia B Cells," *J. Clin. Invest.* 101(5):1133-1141, Mar. 1998.
Kay et al., "Interleukin 4 content in chronic lymphocytic leukemia (CLL) B cells and blood CD8+ T cells from B-CLL patients: impact on clonal B-cell apoptosis," British Journal of Haematology 112:760-767, 2001.
Kim et al., "CDR3 Size Spectatyping and Sequencing of Spectratype-Derived TCR of Spinal Cord T Cells in Autoimmune Enchephalomyelitis," *The Journal of Immunology* 160:509-513, 1998.

(56) References Cited

OTHER PUBLICATIONS

Kirsch et al., "Apoptosis of human T-cells: induction by glucocorticoids or surface receptor ligation in vitro and ex vivo," *J. Biol. Regul. Homeost. Agents* 13(2):80-89, 1999.

Koetz et al., "T cell homeostasis in patients with rheumatoid arthritis," *Proc. Natl. Acad. Sci.* 97(16):9203-9208, Aug. 1, 2000.

Kolowos et al., "Detection of restricted junctional diversity of peripheral T cells in SLE patients by spectratyping," *Lupus* 6:701-707, 1997.

Kornacker et al., "Survivin expression correlates with apoptosis resistance after lymphocyte activation and is found preferentially in memory T cells," *Immunology Letters* 76:169-173, 2001.

Krawczyk et al., "Cbl-b Is a Negative Regulator of Receptor Clustering and Raft Aggregation in T Cells," *Immunity* 13:463-473, Oct. 2000.

Lamy et al., "Large Granular Lymphocyte Leukemia," *Cancer Control* 5(1):25-33, 1998. Available at www.moffitt.usf.edu.

Lanzavecchia et al., "In vitro selective expansion of allergen specific T cells from atopic patients," *Clinical Exp. Immunol.* 52(1):21-28, Apr. 1983.

Lanzavecchia, "The Role of Dendritic Cells in the Generation of Effector and Memory T Cell Responses," from *The Midwinter Conference of Immunologists*, Jan. 22-25, 2000, available at www.midwconfimmunol.org/Midwinter00/sessions/lanzavecchia.html.

Larsson et al., "Productive Cytomegalovirus (CMV) Infection Exclusively in CD13-Positive Peripheral Blood Mononuclear Cells from CMV-Infected Individuals," *Transplantation*, 65(3):411-415, Feb. 15, 1998.

Laytragoon-Lewin et al., "Alteration of Cellular Mediated Cytotoxicity, T Cell Receptor Zeta (TcR ζ) and Apoptosis Related Gene Expression in Nasopharyngeal Carcinoma (NPC) Patients: Possible Clinical Relevance," *Anticancer Research* 20:1093-1100, 2000.

Lehmann et al., "Determinant spreading and the dynamics of the autoimmune T-cell repertoire," *Immunology Today* 14(5):203-208, 1993.

Levine et al., "Antiviral Effect and Ex Vivo CD4$^+$ T Cell Proliferation in HIV-Positive Patients as a Result of CD28 Costimulation," *Science* 272:1939-1943, Jun. 28, 1996.

Levings et al., "Human CD25$^+$ CD4$^+$ T regulatory cells suppress naïve and memory T cell proliferation and can be expanded in vitro without loss of function," *J. Exp. Med.* 193(11):1295-1302, Jun. 2001.

Li et al., "Expanded Tumor-reactive CD4$^+$ T-Cell Responses to Human Cancers Induced by Secondary Anti-CD3/Anti-CD28 Activation," *Clinical Cancer Research* 5:461-469, Feb. 1999.

Li et al, "Immunological Effects of BCG as an Adjuvant in Autologous Tumor Vaccines," *Clinical Immunology* 94(1):64-72, Jan. 2000.

Li et al., "CDR3 Sequence Motifs Shared by Oligoclonal Rheumatoid Arthritis Synovial T Cells. Evidence for an Antigen-driven Response," *Journal of Clinical Investigation* 94:2525-2531, Dec. 1994.

Liebowitz et al., "Costimulatory approaches to adoptive immunotherapy," *Current Opinion in Oncology* 10:533-541, 1998.

Lim et al., "Spread of Clonal T-Cell Expansions in Rheumatoid Arthritis Patients," *Human Immunology* 48:77-83, 1996.

Lin et al., "Stability and Diveristy of T Cell Receptor Repertoire Usage during Lymphocytic Choriomenigitis Virus Infection of Mice," *Journal of Experimental Medicine* 188(11):1993-2005, Dec. 7, 1998.

Liu et al., "Calcineurin is a Common Target of Cyclophilin-Cyclosporin A and FKBP-FK506 Complexes," *Cell* 66:807-815, 1991.

Liuzzo et al., "Monoclonal T-Cell Proliferation and Plaque Instability in Acute Coronary Syndromes," *Circulation* 102:2883-2888, 2000.

Liuzzo et al., "Perturbation of the T-Cell Repertoire in Patients with Unstable Angina," *Circulation* 100:2135-2139, Nov. 1999.

Lopez et al., "CD58/LFA-3 and IL-12 provided by activated monocytes are critical in the in vitro expansion of CD56$^+$ T cells," *Cancer Immunol. Immunother.* 49:629-640, 2001.

Lum et al., "Immune Modulation in Cancer Patients After Adoptive Transfer of Anti-CD3/Anti-CD28-Costimulated T Cells—Phase I Clinical Trial," J. Immunotherapy, 24(5):408-419, 2001.

Mantegazza et al., "Analysis of T Cell Receptor Repertoir of Muscle-infiltrating T Lymphocytes in Polymyositis. Restricted Vα/β Rearragements May Indicate Antigen-driven Selection," *Journal of Clinical Investigation* 91:2880-2886, Jun. 1993.

Marijt et al., "Specific T Cell Therapy in Leukemia," *Journal of Hematotherapy & Stem Cell Research* 10:493-500, 2001.

Martin et al., "T-Cell Receptors and Autoimmune Thyroid Disease—Signposts for T-Cell-Antigen Driven Diseases," *Intern. Rev. Immunol.* 18:111-140, 1999.

Martin et al., "Diversity in fine specificity and T cell receptor usage of the human CD4$^+$ cytotoxic T cell response specific for the immunodominant myelin basic protein peptide 87-106," *Journal of Immunology* 148(5):1359-1366, Mar. 1, 1992.

McCarty, "Upregulation of lymphocyte apoptosis as a strategy for preventing and treating autoimmune disorders: a role for whole-food vegan diets, fish oil and dopamine agonists," *Med. Hyposetheses* 57(2):258-275, Aug. 2001.

McFarland et al., "Amelioration of Autoimmune Reactions by Antigen-Induced Apoptosis of T Cells," *Adv. Exp. Med. Biol.* 383:157-166, 1995.

McIntosh et al., "Induction of Apoptosis in Activated T Cell Blasts by Suppressive Macrophages: A Possible Immunotherapeutic Approach for Treatment of Autoimmune Disease," *Cellular Immunology* 193:24-35, 1999.

McIntosh et al., "Analysis of the T Cell Receptor Vα Repertoire in Hashimoto's Thyroiditis: Evidence for the Restricted Accumulation of CD8$^+$ T Cells in the Absence of CD4$^+$ T Cell Restriction," *Journal of Clinical Endocrinology and Metabolism* 82(4):1140-1146, 1997.

Melms et al., "Specific immune complexes augment in vitro acetylcholine receptor-specific T-cell proliferation," *Neurology* 43:583-588, Mar. 1993.

Migita et al., "FK506 Markedly Enhances Apoptosis of Antigen-Stimulated Peripheral T Cells BY Down-Regulation of Bcl-$x_L$," *Transplantation* 68(7):1018-1023, Oct. 15, 1999.

Moebius et al., "T cell receptor gene rearrangements of T lymphocytes infiltrating the liver in chronic active hepatitis B and primary biliary cirrhosis (PBC): oligoclonality of PBC-derived T cell clones," *Eur. J. Immunol.* 20:889-896, 1990.

Müller et al., "Induction of Apoptosis and Anergy in Resting Human T-Lymphocytes After CD3-Triggering and its Modulation by CD28 and Cytokines," *European J. of Cancer* 31(1003):S34, Abstract No. 70, Oct. 1995.

Müller et al., "Reduction of CD3-Mediated Apoptosis in Human T Cells by CD28-Costimulation: Possible Mechanisms," *European J. of Cancer* 33:S35, Abstract No. 82, Jun. 1997.

Murata et al., "Limited TCR Repertoire of Infiltrating T Cells in the Kidneys of Sjögren's Syndrome Patients with Interstitial Nephritis," *The Journal of Immunology* 155:4084-4089, 1995.

Murphy et al., "Clinical Clearing of Psoriasis by 6-Thioguanine Correlates With Cutaneous T-Cell Depletion via Apoptosis," *Arch. Dermatol.* 135:1495-1502, Dec. 1999.

Musette et al., "Expansion of a recurrent Vβ5.3$^+$ T-cell population in newly diagnosed and untreated HLA-DR2 multiple sclerosis patients," *Proc. Natl. Acad. Sci.* 93:12461-12466, Oct. 1996.

Nagahara et al., "Evidence that FTY720 induces T cell apoptosis in vivo," *Immunopharmacology* 48:75-85, 2000.

Nakashima et al., "The Role of T Cells Expressing TcR Vβ13 in Autoimmune Thyroiditis Induced by Transfer of Mouse Thyroglobulin-Activated Lymphocytes: Identification of Two Common CDR3 Motifs," *Clinical Immunology and Immunopathology* 80(2):204-210, 1996.

Namekawa et al., "Killer Cell Activating Receptors Function as Costimulatory Molecules on CD4$^+$ CD29$^{null}$ T Cells Clonally Expanded in Rheumatoid Arthritis," *The Journal of Immunology* 165:1138-1145, 2000.

Nijhuis et al., "Stochastic processes strongly influence HIV-1 evolution during suboptimal protease-inhibitor therapy," *Proc. Natl. Acad. Scie. USA* 95:14441-14446, Nov. 1998.

(56) References Cited

OTHER PUBLICATIONS

Nikolic-Paterson et al., "T-Cell-Specific Therapy in Autoimmune Glomerulonephritis," *American Journal of Kidney Diseases* 38(6):1321-1328, Dec. 2001.
Nomura et al., "Twenty-five types of T-cell receptor Vβ family repertoire in patients with Kawasaki syndrome," *Eur. J. Pediatr.* 157:981-986, 1998.
O'Reilly et al., "Apoptosis and autoimmune disease," *Inflamm. Res.* 48:5-21, 1999.
Ogura et al., "Induction of apoptosis by novel synthesized acylamides of human lymphocytes," *Biochimica et Biophysica Acta* 1483:111-118, 2000.
Okamoto et al., "T Cell Repertoir in Primary Biliary Cirrhosis: A Common T Cell Clone and Repertoire Change After Treatment," *Journal of Clinical Immunology* 21(4):278-285, 2001.
Olive et al., "Restricted junctional diversity of T cell receptor δ gene rearrangements expressed in systemic lupus erythematosus (SLE) patients," *Clin. Exp. Immunol.* 97:430-438, 1994.
Paillot et al., "Activation-dependent lymphocyte apoptosis induced by methotrexate," *Transplant Proc.* 30(5):2348-2350, Aug. 1998.
Perkins et al., "Restriction of the TCR Repertoire Inhibits the Development of Memory T Cells and Prevents Autoimmunity in *lpr* Mice," *The Journal of Immunology* 156:4961-4968, 1996.
Pinkoski et al., "Lymphocyte apoptosis: refining the paths to perdition," *Current Opinion in Hematology* 9:43-49, 2002.
Planey et al., "Flucocorticoid-induced apoptosis in lymphocytes," *Biochem. Biophys. Res. Commun.* 279(2):307-312, Dec. 2000.
Polanski et al., "Xcellerate( : A Closed, Scalable Process for the GMP Manufacture of Stable Activated T Cells," in *Proceedings of the 15th Annual Scientific Meeting of the Society for Biological Therapy*, Seattle, Oct. 26-29, 2000, and *Journal of Immunotherapy*, (23)5:599, Sep. 2000.
Prinz et al., "Selection of conserved TCR VDJ rearrangements in chronic psoriatic plaques indicates a common antigen in psoriasis vulgaris," *Eur. J. Immunol.* 29:3360-3368, 1999.
Prinz et al., "T cell clones from psoriasis skin lesions can promote keratinocyte proliferation in vitro via secreted products," *Eur. J. Immunol.* 24:593-598, 1994.
Qiao et al., "T cell receptor repertoire and mitotic responses of lamina propria T lymphocytes in inflammatory bowel disease," *Clin. Exp. Immunol.* 97(2):303-308, Aug. 1994.
Ranheim et al., "Activated T Cells Induce Expression of B7/BB1 on Normal or Leukemic B Cells through a CD40-dependent Signal," *J. Exp. Med.* 177:925-935, Apr. 1993.
Ravirajan et al., "Apoptosis in Human Autoimmune Diseases," *Intern. Rev. Immunol.* 18:563-589, 1999.
Rawlings et al., "Spontaneous apoptosis in lymphocytes from patients with Wiskoot-Aldrich syndrome: correlation of accelerated cell death and attenuated bcl-2 expression," *Blood* 94(11):3872-3882, Dec. 1999.
Renz et al., "T cell receptor-Vβ repertoire in allergen-specific sensitization and increased airway responsiveness," *Allergy* 50(suppl. 25):15-19, 1995.
Ria et al., "Molecular Characterization of the T Cell Repertoire Using Immuno-scope Analysis and its Possible Implementation in Clinical Practice," *Current Molecular Medicine* 1:297-304, 2001.
Riddell et al., "T-Cell Therapy of Leukemia," *Cancer Control* 9(2):114-122, Mar./Apr. 2002.
Rodriguez-Palmero et al., "Triggering of T cell proliferation through CD28 induces GATA-3 and promotes T helper type 2 differentiation in vitro and in vivo," *Eur. J. Immunol.* 29(12):3914-3924, Dec. 1999.
Sakaguchi et al., "Immunologic Tolerance Maintained by $CD25^+$ $CD4^+$ Regulatory T Cells: Their Common Role in Controlling Autoimmunity, Tumor Immunity, and Transplantation Tolerance," *Immunological Reviews* 182:18-32, Aug. 2001.
Salomon et al., "B7/CD28 Costimulation is Essential for the Homeostasis of the $CD4^+CD25^+$ Immunoregulatory T Cells that Control Autoimmune Diabetes," *Immunity* 12:431-440, Apr. 2000.
Sasajima et al., "Detection of T cell Apoptosis after Major Operations," *Eur. J. Surg.* 165:1020-1023, 1999.

Schmidt et al., "The Repertoire of $CD4^+$ $CD28^-$ T Cells in Rheumatoid Arthritis," *Molecular Medicine* 2(5):608-618, Sep. 1996.
Schmidt et al., "The Repertoire of $CD4^+$ $CD28^-$ T Cells in Rheumatoid Arthritis," *Molecular Medicine* 2(5): 11076- 1551, Sep. 1996.
Schmidt et al., "T-cell apoptosis in situ in experimental autoimmune encephalomyelitis following methylprenisolone pulse therapy," *Brain* 123(pt. 7):1431-1441, Jul. 2000.
Schneider et al., "Experimental autoimmune myositis in the Lewis rat: lack of spontaneous T-cell apoptosis and therapeutic response to glucocorticosteroid application," *Journal of Neuroimmunology* 107:83-87, 2000.
Shevach et al., "Regulatory T Cells in Autoimmunity," *Annu. Rev. Immunol.* 18:423-449, 2000.
Shibuya et al., "Anti-CD3/Anti-CD28 Bead Stimulation Overcomes CD3 Unresponsiveness in Patients With Head and Neck Squamous Cell Carcinoma," *Archives of Otolaryngol Head Neck Surg.* 126(4):473-479, Apr. 2000.
Shimizu et al., Large-Scale ex Vivo Expansion of Primary T Lymphocytes in Late-Stage AIDS Patients, *AIDS Research and Human Retroviruses* 16(6):611-612, 2000.
Smith et al., "In vitro T cell proliferation from kidney allograft biopsies with unremarkable pathology: new strategies for an old problem," *Transplantation* 73(3):142-145, Jan. 2002.
Snyder et al., "Formation of the Killer Ig-Like Receptor Repertoire on $CD4^+$ $CD28^{null}$ T Cells," *The Journal of Immunology* 168:3839-3846, 2002.
Söderström et al., "Autoimmune T cell repertoire in optic neuritis and multiple sclerosis: T cells recognizing multiple myelin proteins are accumulated in cerebrospinal fluid," *Journal of Neurology, Neurosurgery, and Psychiatry* 57:544-551, 1994.
Stahnke et al., "Activation of apoptosis pathways in peripheral blood lymphocytes by in vivo chemotherapy," *Blood* 98(10):3066-3073, Nov. 15, 2001.
Stephens et al., "Human $CD4^+CD25^+$ Thymocytes and Peripheral T Cells have Hmmune Suppresive Activity in Vitro," *Eur. J. Immunol.* 31:1247-1254, 2001.
Stohl et al., "Polyclonal in Vitro T Cell Proliferation and T Cell-Dependent B Cell Differentiation Supported by Activated Autologous B Cells," *Clinical Immunology and Immunopathology* 72(1):44-52, Jul. 1994.
Strauss et al., "Induction of apoptosis and modulation activation and effector function in T cells by immunosuppressive drugs," *Clin Exp. Immunol.* 128:255-266, 2002.
Takemura et al., "T Cell Activation in Rheumatoid Synovium Is B Cell Dependent," *The Journal of Immunology* 167:4710-4718, 2001.
Tao et al., "Conservation of Epstein-Barr Virus Cytotoxic T-Cell Epitopes in Posttransplant Lymphomas. Implications for Immune Therapy," *American Journal of Pathology* 160(5):1839-1845, May 2002.
Tokushige et al., "Abnormal T Cell Activation and Skewed T Cell Receptor Vβ Repertoire Usage in Japanese Patients with Idiopathic Portal Hypertension," *Clinical Immunology and Immunopathology* 75(3):206-213, 1995.
Trickett et al., "Ex vivo expansion of functional T lymphocytes from HIV-infected individuals," *Journal of Immunological Methods* 262:71-83, 2002.
Vathsala et al., "Inhibition of Apoptosis in Anti-CD3-Treated Peripheral Blood Lymphocytes by Immunosuppressive Drugs," *Transplantation Proceedings* 32:1992-1994, 2000.
Vavassori et al., "Restricted TCR Repertoire and Long-Term Persistence of Donor-Derived Antigen-Experienced $CD4^+$ T Cells in Allogeneic Bone Marrow Transplantation Recipients," *The Journal of Immunology* 157:5739-5747, 1996.
Warrington et al., "CD4+, CD28– T Cells in Rheumatoid Arthritis Patients Combine Features of the Innate and Adaptive Immune Systems," *Arthritis & Rheumatism* 44(1):13-20, Jan. 2001.
Weishaupt et al., "Antigen therapy eliminates T cell inflammation by apoptosis: effective treatment of experimental autoimmune neuritis with recombinant myelin protein P2," *Proc. Natl. Acad. Sci. USA* 94(4):1338-1343, Feb. 1997.
Weishaupt et al., "Glucocorticosteroids modulate antigen-induced T cell apoptosis in experimental autoimmune neuritis and cause T cell proliferation in situ," *Acta Neuropathol.* 102(1):75-82, Jul. 2001.

(56) References Cited

OTHER PUBLICATIONS

Weyand et al., "Functional Properties of CD4+ CD28− T Cells in the Aging Immune System," *Mech. of Ageing and Development* 102(2 &3):131-147, May 1998.
White et al., "The roles of Fas, Fas ligand and Bcl-2 in T cell apoptosis in the central nervous system in experimental autoimmune encephalomyelitis," *Journal of Neuroimmunology* 82:47-55, 1998.
Wong et al., "Analysis of the Peripheral T-Cell Receptor Vβ Repertoire in Newly Diagnosed Patients with Type I Diabetes," *Autoimmunity* 18:77-83, 1994.
Woo et al., "Cutting Edge: Regulatory T Cells from Lung Cancer Patients Directly Inhibit Autologous T Cell Proliferation," *J. Immunol.* 168(9):4272-4276, May 2002.
Wu et al., "TCR Gene Usage in Experimental Autoimmune Myasthenia Gravis Pathogenesis," *The Journal of Immunology* 154:3603-3610, 1995.
Wu et al., "Conserved T-cell receptor β-chain CDR3 sequences in IgA nephrology biopsies," *Kidney International* 55:109-119, 1999.
Wucherpfennig et al., "T Cell Receptor $V_\alpha$-$V_\beta$ Repertoire and Cytokine Gene Expression in Acitve Mulitple Sclerosis Lesions," *Journal of Experimental Medicine* 175:993-1002, Apr. 1992.
Xiao et al., "Mechanisms of recovery from experimental allergic encephalomyelitis induced with myelin basic protein peptide 68-86 in Lewis rats: a role for dendritic cells in inducing apoptosis of CD4$^+$ T cells," *J. Neuroimmunol.* 97(1-2):25-36, 1999.
Yamada et al., "Clonal T-cell proliferation causing pure red cell aplasia in chronic B-cell lymphocytic leukaemia: successful treatment with cyclosporine following in vitro abrogation of erythroid colony-suppressing activity," *British Journal of Haematology* 101:335-337, 1998.
Yang et al., "Apoptosis of infiltrating cells in experimental autoimmune ureoretinitis," *Chinese Medical Journal* 113(7):643-646, 2000.
Yu et al., "Apoptosis of CD4$^+$ T cells occurs in experimental autoimmune anterior uveitis (EAAU)," *Clin. Exp. Immunol.* 118:357-363, 1999.
Zipp et al., "Dual effect of glucocortocoids on apoptosis of human autoreactive and foreign antigen-specific T cells," *J. Neuroimmunol.* 110(1-2):214-222, Oct. 2000.
Zou et al., "Tumor-Bearing Mice Exhibit A Progressive Increase in Tumor Antigen-Presenting Cell Function and a Reciprocal Decrease in Tumor Antigen-Responsive CD4$^+$ T Cell Activity," *The Journal of Immunology* 148(2):648-655, Jan. 15, 1992.
Blyth et al., "Lung Inflammation and Epithelial Changes in a Murine Model of Atopic Asthma," *Am. J. Respir. Cell Mol. Biol.* 14(5):425-438, 1996.
Bonneville et al., "Self-tolerance to transgenic gamma delta T cells by intrathymic inactivation," *Nature* 344:163-165, 1990.
Dent et al., "Self-reactive gamma delta T cells are eliminated in the thymus," *Nature* 343:714-719, 1990.
Eisenberg et al., "Male determined accelerated autoimmune disease in BXSB mice: transfer by bone marrow and spleen cells," *J. Immunol.* 125:1032-1036, 1980.
Hu et al., "Kinetics of interferon-gamma secretion and its regulatory factors in the early phase of acute graft-versus-host disease," *Immunology* 98(3):379-385, 1999.
Makino et al., "Breeding of a Non-Obese, Diabetic Strain of Mice," *Exp. Anim.* 29:1-13, 1980.
Morris et al., "Experimental induction of systemic lupus erythematosus by recognition of foreign Ia," *Clin. Immunol. Immunopathol.* 57:263-273, 1990.
Takahashi et al., "Generalized lymphoproliferative disease in mice, caused by a point mutation in the Fas ligand," *Cell* 76:969-976, 1994.
Takakura et al., "An in vivo model of human skin acute graft-versus-host disease: transplantation of cultured human epidermal cells and dermal fibroblasts with human lymphocytes into SCID mice," *Exp. Hematol.* 27(12):1815-821, 1999.
Tarui et al., "Immunological Manipulation of Diabetes Production in NOD Mice," *Insulitis and Type 1 Diabetes Lessons from the NOD Mouse*, Academic Press, Tokyo, p. 143, 1986.
Theofilopoulos and Dixon, "Murine models of systemic lupus erythematosus," *Adv. Immunol.* 37:269-389, 1985.
Todd et al., "Genetic analysis of autoimmune type 1 diabetes mellitus in mice," *Nature* 351:542-547, 1991.
Trentham et al., "Autoimmunity to Type II Collagen: An Experimental Model of Arthritis," *J. Exp. Med.* 146: 857-868, 1977.
Watanabe et al., "A molecular genetic linkage map of mouse chromosome 19, including the lpr, Ly-44, and Tdt genes," *Biochem Genet.* 29:325-335, 1991.
Kalamasz, Dale et al., "Optimization of Human T-Cell Expansion Ex Vivo Using Magnetic Beads Conjugated with Anti-CD3 and Anti-CD28 Antibodies," *Journal of Immunother*, vol. 27, No. 5, Sep. 2004, 405-418.

* cited by examiner

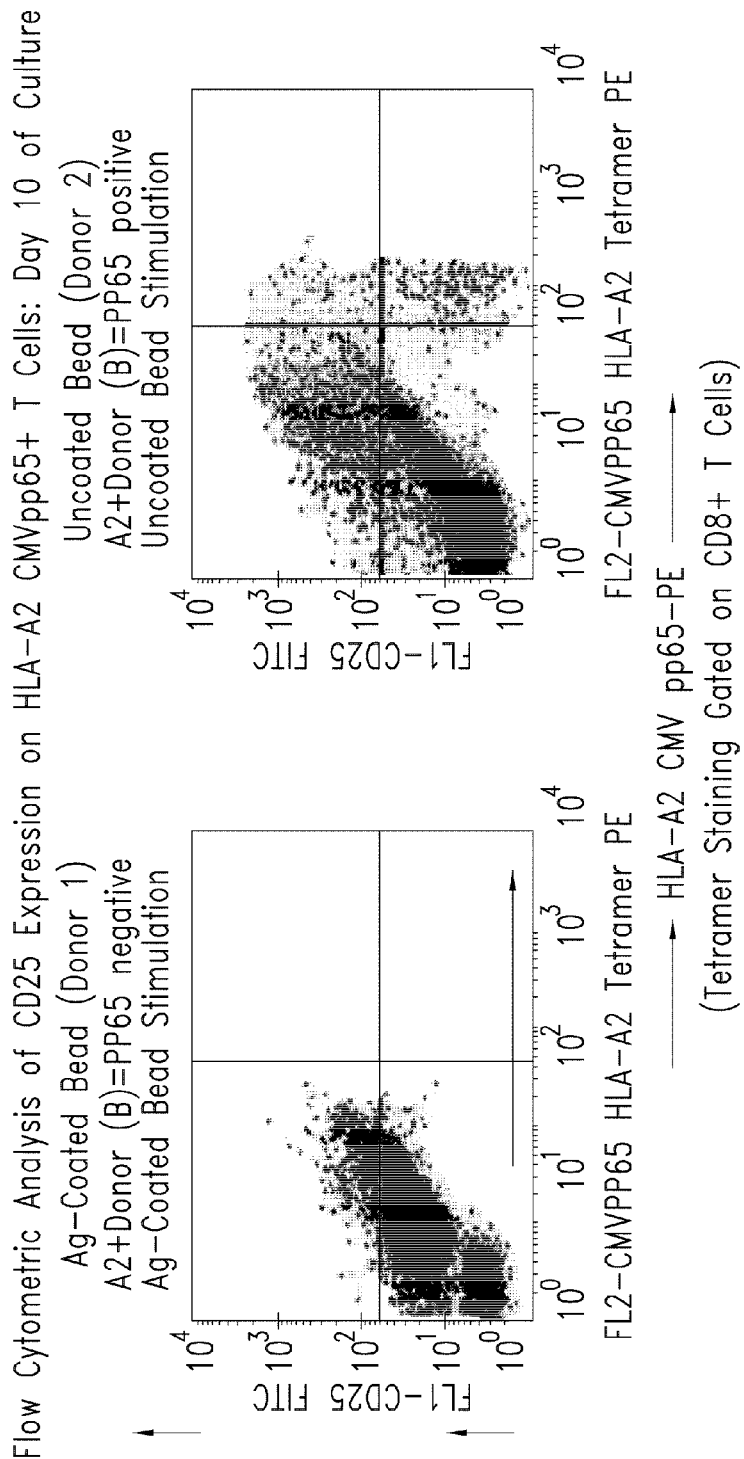

PBMC were activated with CMV antigen (coated onto paramagnetic beads) and by day 10 of culture, many cell are shown to be CD25 (IL-2R) positive, and all of the HLA-A2 CMVpp65+ T cells are expressing high levels of CD25, indicating activation (FIG. 2B). Controls include the same donor cells treated with uncoated (antigen-negative) beads (FIG. 2B), or an HLA-A2+ donor (donor 1) that did not show detectable tetramer+ cells at day 0 and was serologically negative for CMV (FIG. 2A). These data indicate that tetramer approaches can be effectively used to track antigen-specific T cells and their relative state of activation.

Flow Cytometric Analysis of CD25 Expression on HLA-A2 CMVpp65+ T Cells: Day 10 of Culture

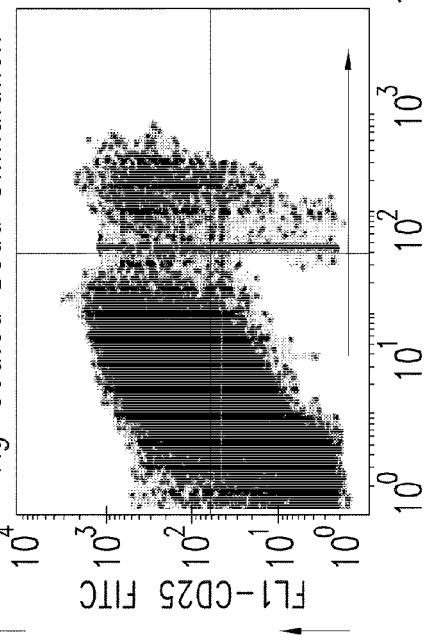

FIG. 2C

PBMC were activated with CMV antigen (coated onto paramagnetic beads) and by day 10 of culture, many cell are shown to be CD25 (IL-2R) positive, and all of the HLA-A2 CMVpp65+ T cells are expressing high levels of CD25, indicating activation (FIG. 2C). Controls include the same donor cells treated with uncoated (antigen-negative) beads (FIG. 2B), or an HLA-A2+ donor (donor 1) that did not show detectable tetramer+ cells at day 0 and was serologically negative for CMV (FIG. 2A). These data indicate that tetramer approaches can be effectively used to track antigen-specific T cells and their relative state of activation.

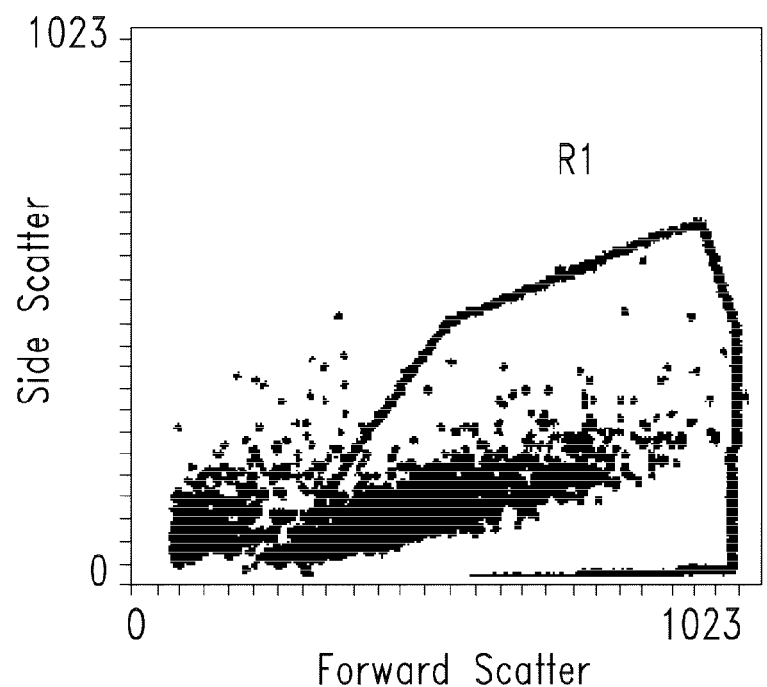
FIG. 3A1
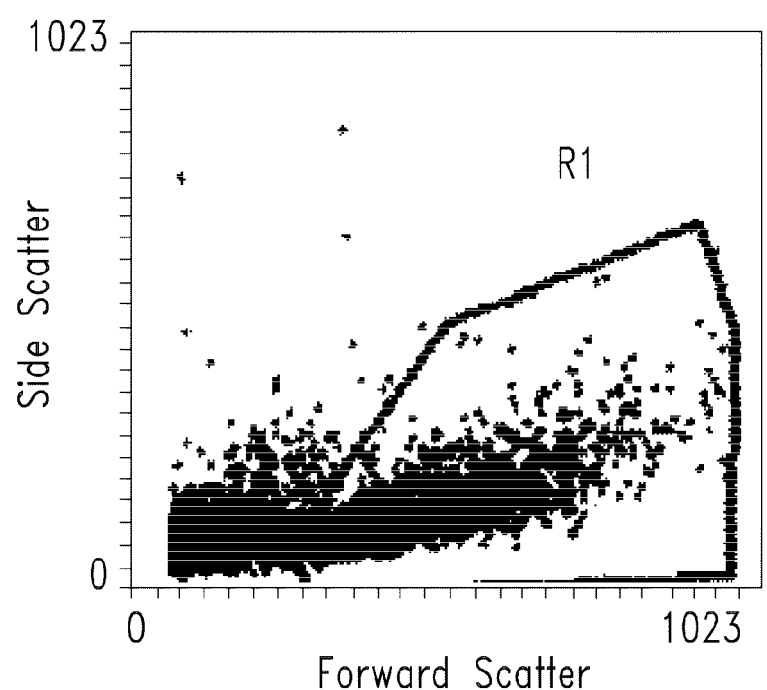
FIG. 3B1

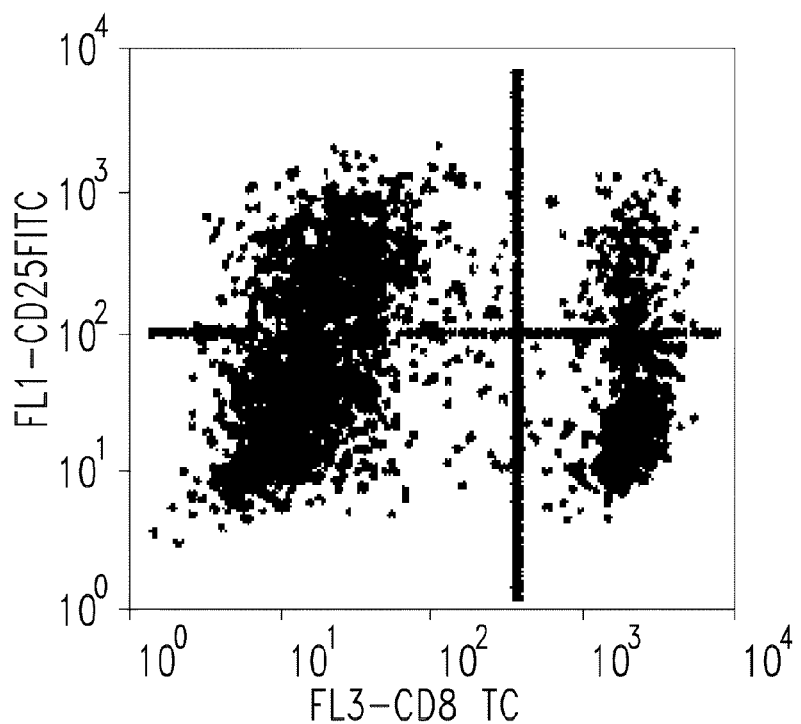
FIG. 3A2
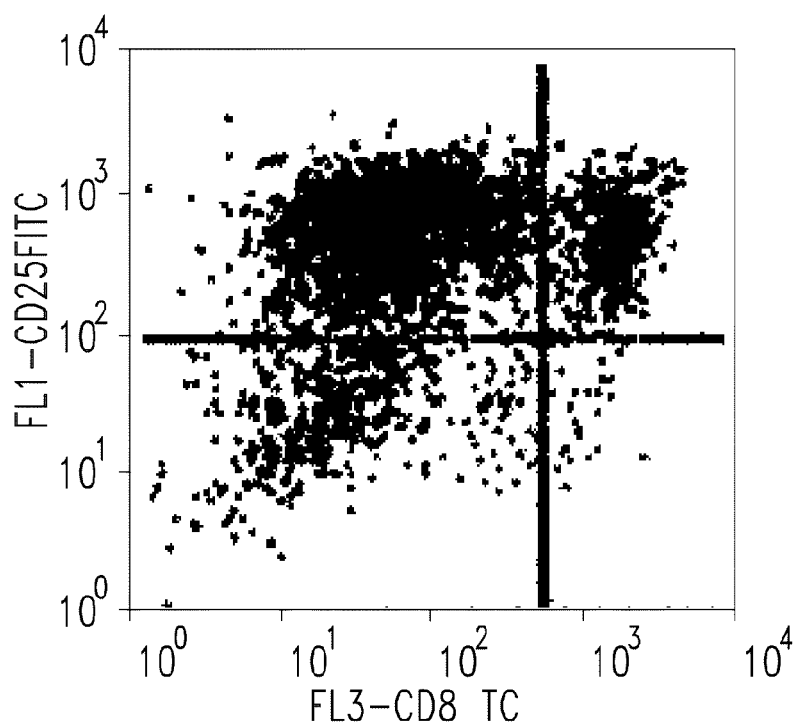
FIG. 3B2

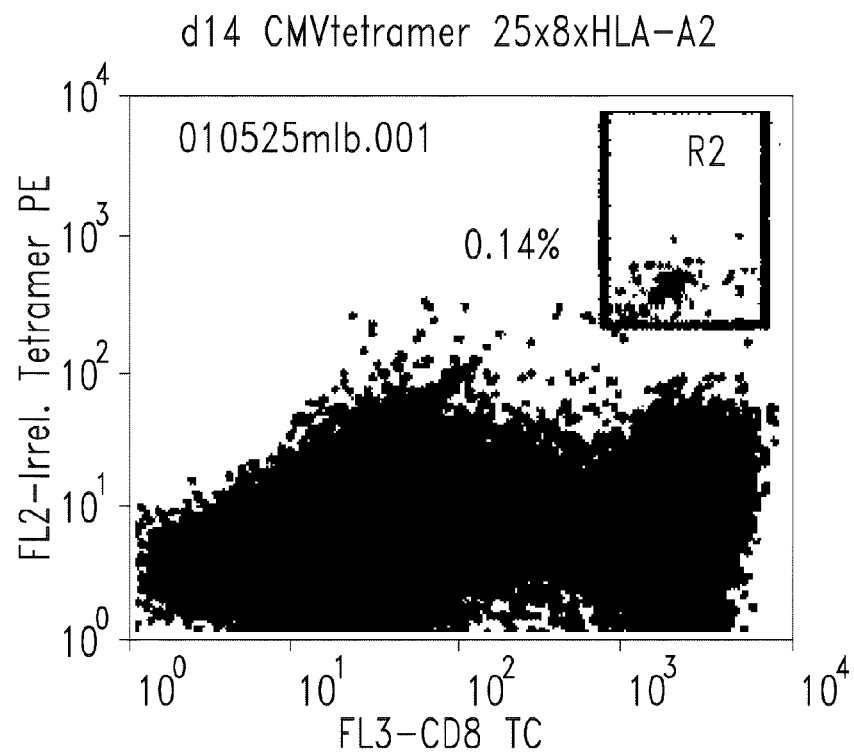
*FIG. 3A3*
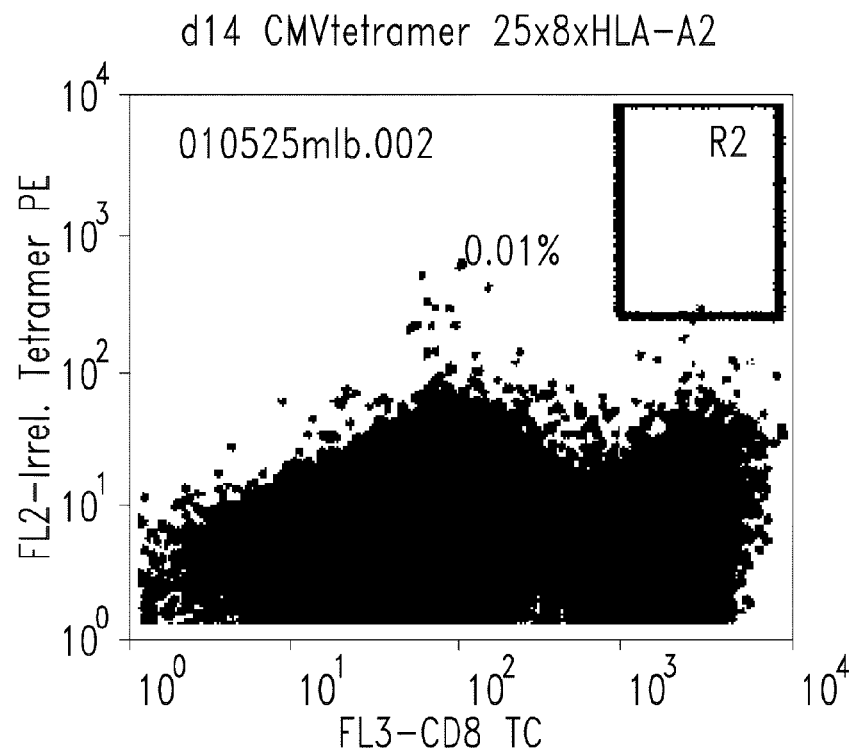
*FIG. 3B3*

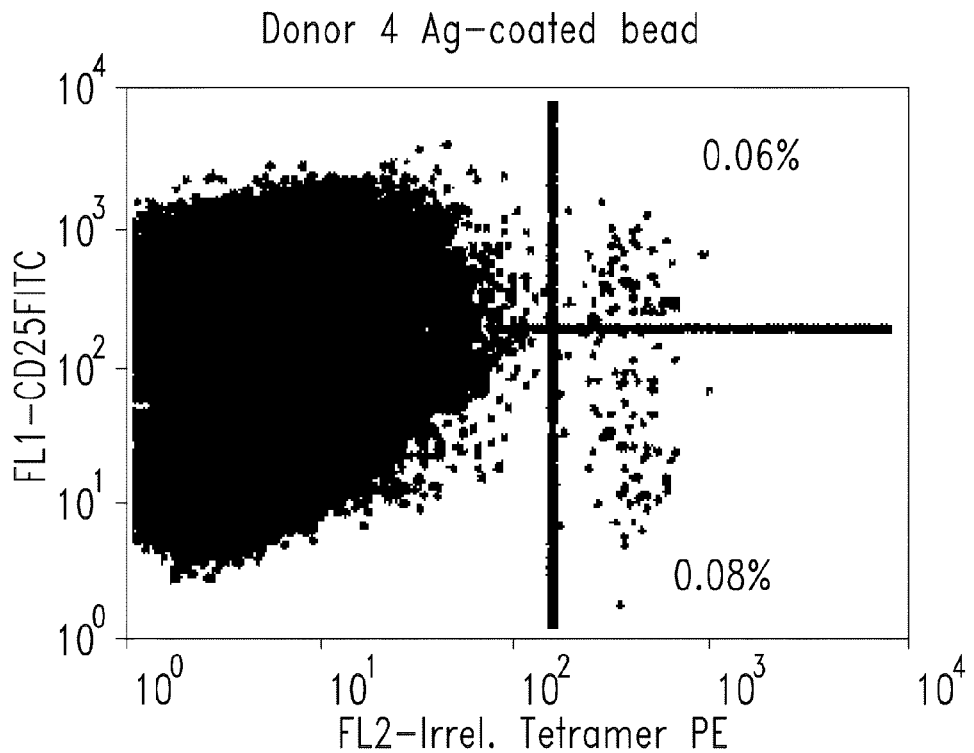
FIG. 3A4
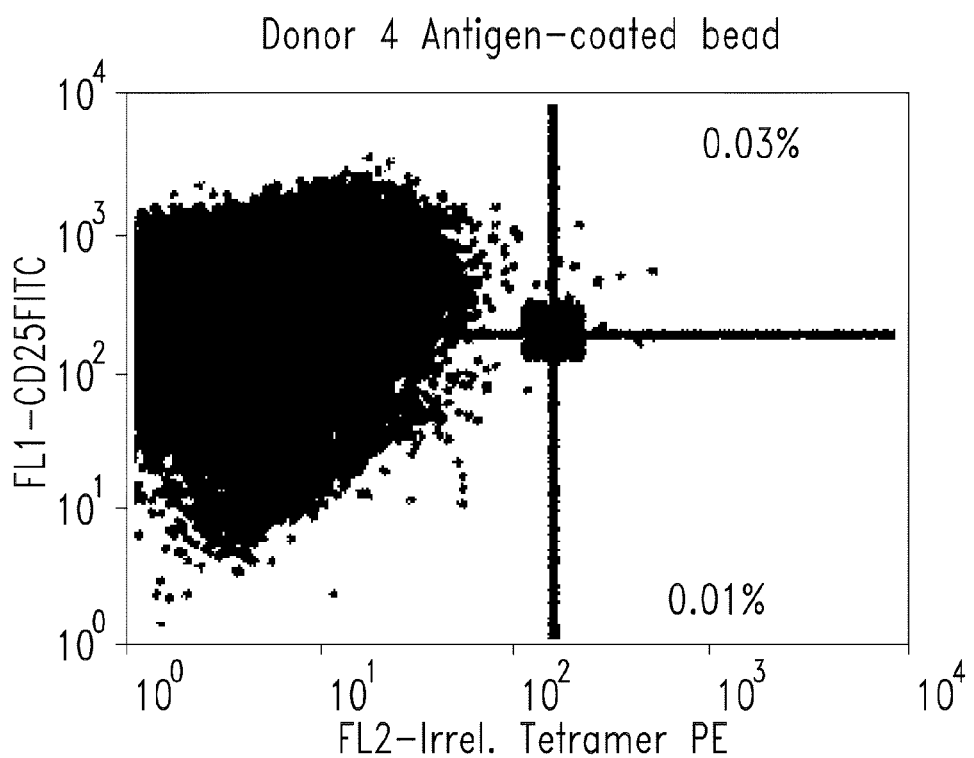
FIG. 3B4

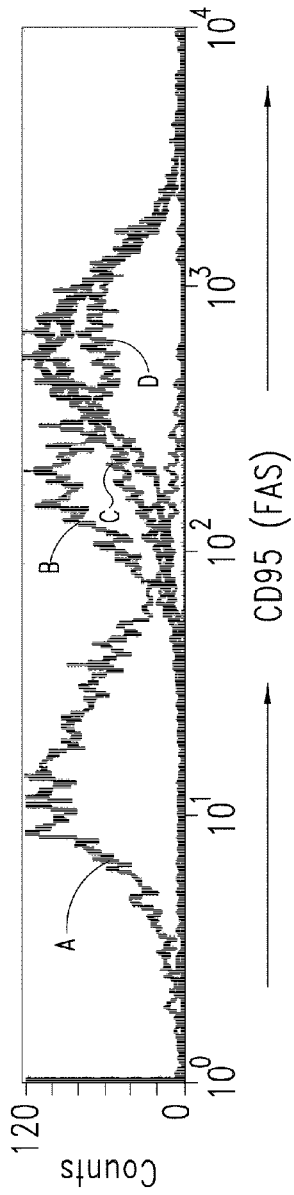
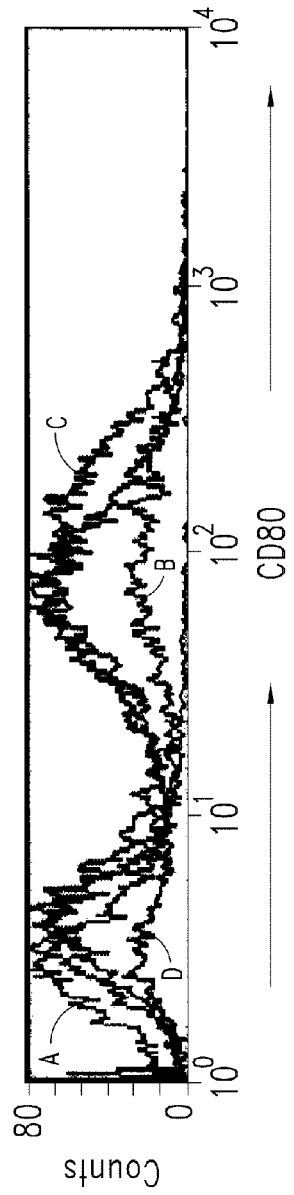
FIG. 4A
FIG. 4B
Effector Molecules Day 12 Xcellerated T Cells Co-cultured 24 hours with autologous leukemic B Cells Results in the Rapid Upregulation of Key Immunological
A= Leukemic Cells
B= Leukemic B Cells + Xcellerated T Cells
T:B ratio=0.3:1
C= Leukemic B Cells + Xcellerated T Cells
T:B ratio=1:1

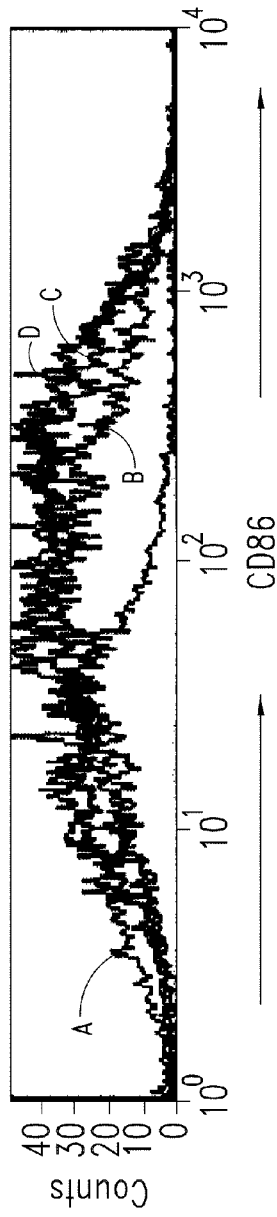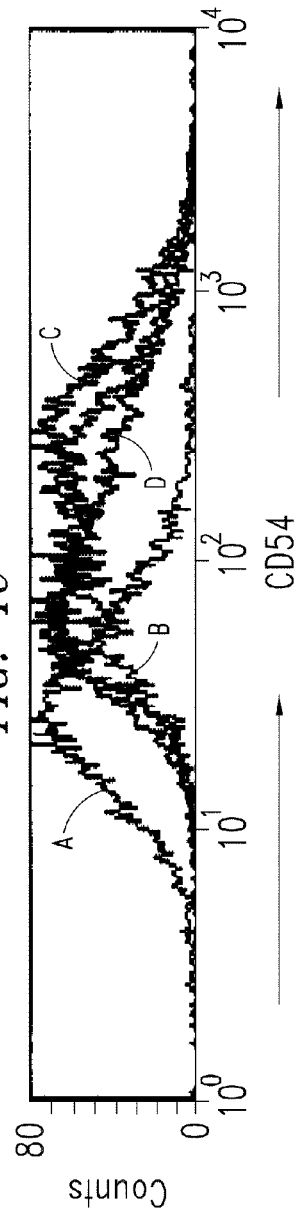
FIG. 4C
FIG. 4D

METHODS FOR ELIMINATING AT LEAST A SUBSTANTIAL PORTION OF A CLONAL ANTIGEN-SPECIFIC MEMORY T CELL SUBPOPULATION

CROSS-REFERENCE TO RELATED APPLICATIONS

This application is a continuation of U.S. patent application Ser. No. 10/900,046, filed Jul. 27, 2004, now abandoned, which application is a continuation-in-part of U.S. patent application Ser. No. 10/729,822, filed Dec. 5, 2003, now abandoned, which application is a continuation-in-part of U.S. patent application Ser. No. 10/603,577, filed Jun. 24, 2003, now abandoned, and which claims the benefit under 35 U.S.C. §119(3) of U.S. Provisional Patent Application No. 60/442,001, filed Jan. 22, 2003, now expired.

BACKGROUND OF THE INVENTION

1. Field of the Invention

The present invention relates generally to methods for stimulating T cells to restore normal immune repertoire. The present disclosure includes methods to eliminate undesired (e.g., autoreactive, alloreactive, pathogenic) subpopulations of T cells from a mixed population of T cells, thereby restoring the normal immune repertoire of said T cells. The present invention also relates to compositions of cells, including stimulated T cells having restored immune repertoire and uses thereof.

2. Description of the Related Art

The ability of T cells to recognize the universe of antigens associated with various cancers or infectious organisms is conferred by its T cell antigen receptor (TCR), which is made up of both an α (alpha) chain and a β (beta) chain or a γ (gamma) and a δ (delta) chain. The proteins which make up these chains are encoded by DNA, which employs a unique mechanism for generating the tremendous diversity of the TCR. This multisubunit immune recognition receptor associates with the CD3 complex and binds to peptides presented by the major histocompatibility complex (MHC) class I and II proteins on the surface of antigen-presenting cells (APCs). Binding of TCR to the antigenic peptide on the APC is the central event in T cell activation, which occurs at an immunological synapse at the point of contact between the T cell and the APC.

To sustain T cell activation, T lymphocytes typically require a second co-stimulatory signal. Co-stimulation is typically necessary for a T helper cell to produce sufficient cytokine levels that induce clonal expansion. Bretscher, *Immunol. Today* 13:74, 1992; June et al., *Immunol. Today* 15:321, 1994. The major co-stimulatory signal occurs when a member of the B7 family ligands (CD80 (B7.1) or CD86 (B7.2)) on an activated antigen-presenting cell (APC) binds to CD28 on a T cell.

Methods of stimulating the expansion of certain subsets of T cells have the potential to generate a variety of T cell compositions useful in immunotherapy. Successful immunotherapy can be aided by increasing the reactivity and quantity of T cells by efficient stimulation. Furthermore, in the settings of autoimmunity or transplantation, successful immunotherapy can be aided by the elimination of unwanted autoreactive or alloreactive cells.

The various techniques available for expanding human T cells have relied primarily on the use of accessory cells and/or exogenous growth factors, such as interleukin-2 (IL-2). IL-2 has been used together with an anti-CD3 antibody to stimulate T cell proliferation, predominantly expanding the $CD8^+$ subpopulation of T cells. Both the APC signals directed towards the TCR/CD3 complex and CD28 on the surface of T cells are thought to be required for optimal T cell activation, expansion, and long-term survival of the T cells upon re-infusion. The requirement for MHC-matched APCs as accessory cells presents a significant problem for long-term culture systems because APCs are relatively short-lived. Therefore, in a long-term culture system, APCs must be continually obtained from a source and replenished. The necessity for a renewable supply of accessory cells is problematic for treatment of immunodeficiencies in which accessory cells are affected. In addition, when treating viral infection, if accessory cells carry the virus, the cells may contaminate the entire T cell population during long-term culture.

In the absence of exogenous growth factors or accessory cells, a co-stimulatory signal may be delivered to a T cell population, for example, by exposing the cells to a CD3 ligand and a CD28 ligand attached to a solid phase surface, such as a bead. See C. June, et al. (U.S. Pat. No. 5,858,358); C. June et al. WO 99/953823. While these methods are capable of achieving therapeutically useful T cell populations, increased robustness and ease of T cell preparation remain less than ideal.

Methods previously available in the art have made use of anti-CD3 and anti CD28 for the expansion of T cells. In addition, the methods currently available in the art have not focused on short-term expansion of T cells or obtaining a more robust population of T cells and the beneficial results thereof. None of these methods has described using such or similar methods to eliminate an undesired clonal or oligoclonal T cell population from a T cell population nor the beneficial results thereof. Moreover, the methods previously available tend to further skew the clonality of the T cell population rather than eliminate undesired reactive clones from a T cell population, and restore a normal immune repertoire. For maximum in vivo effectiveness, theoretically, an ex vivo- or in vivo-generated, activated T cell population should be in a state that can maximally orchestrate an immune response to cancer, infectious disease, or other disease states. In the setting of autoimmunity or transplantation, the activated T cell populations should be in a state to reconstitute a normal T cell repertoire with a reduced presence or entirely without the presence of autoreactive or potentially pathogenic alloreactive T cells. Currently, patients with autoimmune diseases are treated with long-term immunosuppression to inhibit the autoreactive T cells that cause disease. When the immunosuppressive agents are stopped, disease recurs often concomitant with reappearance of disease causing T cells that re-emerge in these patients. The major problem in hematopoietic stem cell transplantation is graft-versus-host disease (GVHD), which is caused by alloreactive T cells present in the infused hematopoietic stem cell preparation. In organ transplantation, graft rejection mediated by alloreactive host T cells is the major problem, usually overcome by long-term immunosuppression of the transplant recipient.

The present invention provides methods to generate an increased number of more highly activated and more pure T cells that have surface receptor and cytokine production characteristics that appear more healthy and natural than other expansion methods and further provides for the diminution or elimination of undesired autoreactive or alloreactive populations of T cells. The present invention provides methods for the use of said populations of T cells in the setting of autoimmune diseases, hematopoietic stem cell, and organ transplantation, as well as other settings where reconstitution of an ablated, abrogated, or otherwise dysfunctional T cell immune system is desired. In addition, the present invention provides compositions of cell populations of any target cell, including T cell populations and parameters for producing the same, as well as providing other related advantages.

Additionally, it is becoming well recognized that the aging immune system is characterized by a progressive decline in the responsiveness to exogenous antigens and tumors in combination with a paradoxical increase in autoimmunity (C. Weyand et al. Mechanisms of Ageing and Development 102: 131-147, 1998; D. Schmidt et al. Molecular Medicine 2:608-618, 1996; G. Liuzzo et al. Circulation 100:2135-2139, 1999). These studies have described that aging is associated with the emergence of a subset of T helper cells that are characterized by the loss of CD28 expression. $CD4^+CD28^-$ T cells are long lived, typically undergo clonal expansion in vivo, and react to auto-antigens in vitro. The loss of CD28 expression is correlated with a lack of CD40 ligand expression rendering these $CD4^+$ T cells incapable of promoting B cell differentiation and immunoglobulin secretion. Aging-related accumulation of $CD4^+$ $CD28^-$ T cells results in an immune compartment that is skewed towards auto-reactive responses and away from the generation of high-affinity B cell responses against exogenous antigens.

BRIEF SUMMARY OF THE INVENTION

One aspect of the present invention provides for a method for eliminating at least a substantial portion of a clonal T cell population from a mixed population of T cells from an individual, comprising, providing a population of cells wherein at least a portion thereof comprises T cells; exposing the population of cells ex vivo to one or more pro-apoptotic compositions wherein said exposure induces apoptosis in at least a portion of the T cells; thereby eliminating at least a substantial portion of said clonal T cells from the mixed population.

The present invention provides a method for eliminating at least a substantial portion of a clonal T cell subpopulation from a mixed population of T cells from an individual, comprising, exposing a population of cells, wherein at least a portion thereof comprises T cells, to one or more pro-apoptotic or growth inhibiting compositions wherein said exposure induces apoptosis or inhibits growth in at least a substantial portion of at least one clonal T cell population present in the mixed population of T cells thereby eliminating at least a substantial portion of said clonal T cell population from the mixed population of T cells. In one embodiment, the method further comprises expanding the mixed population of T cells, by exposing the remaining mixed population of T cells to the pro-apoptotic composition, wherein said exposure induces proliferation in the mixed population of T cells. In one particular embodiment, the pro-apoptotic composition comprises anti-CD3 and anti-CD28 antibodies co-immobilized on a bead. In certain embodiments, the pro-apoptotic composition used to eliminate at least a substantial portion of said clonal T cell population from the mixed population of T cells is the same composition used to expand the remaining mixed population of T cells.

In one embodiment, the method further comprises expanding the remaining population of cells. In another embodiment, the method further comprises expanding the remaining population of cells by exposing the remaining population of cells to a surface wherein the surface has attached thereto one or more agents that ligate a cell surface moiety of at least a portion of the remaining T cells and stimulates said remaining T cells. In a related embodiment, the surface has attached thereto a first agent that ligates a first T cell surface moiety of a T cell, and the same or a second surface has attached thereto a second agent that ligates a second moiety of said T cell, wherein said ligation by the first and second agent induces proliferation of said T cell.

In one embodiment, the agent attached to the surface is an antibody or an antibody fragment. In another embodiment, the first agent is an antibody or a fragment thereof, and the second agent is an antibody or a fragment thereof. In one embodiment the first and the second agents are different antibodies. In one particular embodiment, the first agent is an anti-CD3 antibody, an anti-CD2 antibody, or an antibody fragment of an anti-CD3 or anti-CD2 antibody. In another embodiment, the second agent is an anti-CD28 antibody or antibody fragment thereof. In a further embodiment, the first agent is an anti-CD3 antibody and the second agent is an anti-CD28 antibody.

In another embodiment, the cells are exposed to the surfaces of the present invention for a time sufficient to increase polyclonality. In certain embodiments, this increase in polyclonality comprises a shift from mono to oligoclonality or to polyclonality of the T cell population as measured by a Vβ, Vα, Vγ, or Vδ spectratype profile of at least one Vβ, Vα, Vγ, or Vδ family gene.

Illustrative pro-apoptotic compositions of the present invention include but are not limited to anti-CD3 antibody, anti-CD2 antibody, anti-CD28 antibody, anti-CD20 antibody, target antigen, MHC-peptide tetramers, Fas ligand, anti-Fas antibody, IL-2, IL-4, TRAIL, rolipram, doxorubicin, chlorambucil, fludarabine, cyclophosphamide, azathioprine, methotrexate, cyclosporine, mycophenolate, FK506, inhibitors of bcl-2, topoisomerase inhibitors, interleukin-1β converting enzyme (ICE)-binding agents, *Shigella* IpaB protein, staurosporine, ultraviolet irradiation, gamma irradiation, tumor necrosis factor, target antigens nucleic acid molecules, proteins or peptides, and non-protein or non-polynucleotide compounds. In certain embodiments, one or more of these compositions are used at the same time.

In certain embodiments of the present invention, the pro-apoptotic compositions comprises an autoantigen. Illustrative autoantigens of the present invention include but are not limited to, myelin basic protein (MBP), MBP 84-102, MBP 143-168, pancreatic islet cell antigens, collagen, CLIP-170, thyroid antigens, nucleic acid, acetylcholine receptor, S Antigen, and type II collagen.

The present invention further provides a population of T cells generated according to any of the methods described above.

The present invention provides a method for eliminating at least a substantial portion of a clonal T cell subpopulation from a mixed population of T cells from an individual, comprising, exposing a population of cells, wherein at least a portion thereof comprises T cells, to one or growth inhibiting compositions wherein said exposure inhibits growth in at least a substantial portion of at least one clonal T cell population present in the mixed population of T cells; the method further comprises expanding the mixed population of T cells, by exposing the population of cells that is not growth inhibited, i.e., the remaining mixed population of T cells to a surface having attached thereto one or more agents that bind to a cell surface molecule. In one embodiment said surface comprises anti-CD3 and anti-CD28 antibodies co-immobilized on a bead.

One aspect of the present invention provides for methods for treating autoimmune disease in a patient comprising administering to a patient the populations of T cells of the present invention. In one embodiment the patient has been treated with a chemotherapeutic agent prior to administering the population of T cells. Illustrative chemotherapeutic agents of the present invention include but are not limited to campath, anti-CD3 antibodies, cytoxin, fludarabine, cyclosporine, FK506, mycophenolic acid, steroids, FR901228, and irradiation. In certain embodiments, the patient is treated with a T cell ablative therapy prior to administration of the populations of T cells of the present invention.

One aspect of the present invention is a method for eliminating at least a substantial portion of a clonal T cell population from a population of T cells from an individual, comprising, providing a population of cells wherein at least a portion thereof comprises T cells; exposing the population of cells to one or more agents that sensitize at least a portion of the T cells to further activation or stimulation, exposing the population of cells to a surface wherein the surface has attached thereto one or more agents that ligate a cell surface moiety of at least a portion of the sensitized T cells and stimulates said sensitized T cells, wherein the exposure of said sensitized T cells to said surface is for a time sufficient to induce apoptosis of said sensitized T cells; thereby eliminating said sensitized T cells from the population. In one embodiment, the method further comprises exposing said population of cells to said surface for a time sufficient to stimulate at least a portion of the remaining T cells and wherein said at least a portion of the remaining cells proliferates. In a further embodiment, the method provides that said surface has attached thereto a first agent that ligates a first T cell surface moiety of a T cell; and the same or a second surface has attached thereto a second agent that ligates a second moiety of said T cell, wherein said ligation by the first and second agent induces proliferation of said T cell. In one embodiment, at least one agent is an antibody or an antibody fragment. In another embodiment, the first agent is an antibody or a fragment thereof, and the second agent is an antibody or a fragment thereof. In yet another embodiment, the first and the second agents are different antibodies. In a related embodiment, the first agent is an anti-CD3 antibody, an anti-CD2 antibody, or an antibody fragment of an anti-CD3 or anti-CD2 antibody. In yet another embodiment, the second agent is an anti-CD28 antibody or antibody fragment thereof. In another embodiment, the first agent is an anti-CD3 antibody and the second agent is an anti-CD28 antibody.

In a related embodiment, cells are exposed to said surface for a time sufficient to increase polyclonality. In another embodiment, the increase in polyclonality comprises a shift from mono to oligoclonality or to polyclonality of the T cell population as measured by a Vβ, Vα, Vγ, or Vδ spectratype profile of at least one Vβ, Vα, Vγ, or Vδ family gene.

In certain embodiments, the patient requires a hematopoietic stem cell transplant. In a related embodiment, the composition that sensitizes recipient PBMCs that have been treated such that they are unable to continue dividing and the population of cells comprises donor T cells. The present invention also provides for populations of T cells generated according to the above methods. The present invention also provides methods for reducing the risk of, or the severity of, an adverse GVHD effect in a patient who is undergoing a hematopoietic stem cell transplant, comprising administering to said patient the population of T cells according to the methods described herein.

In certain embodiments, the patients to receive the cells of the present invention require an organ transplant. In a related embodiment the composition that sensitizes comprises irradiated donor cells and the population of cells comprises recipient T cells. The present invention also provides for a population of cells generated according to this method. In one embodiment, these cells are administered to a patient receiving an organ transplant to reduce the risk of organ rejection. In a related embodiment, the organ transplant patient is treated with a T cell ablative therapy prior to administration of the population of T cells.

In one aspect of the present invention the composition that sensitizes comprises an autoantigen. Illustrative autoantigens of the present invention include but are not limited to myelin basic protein (MBP), MBP 84-102, MBP 143-168, pancreatic islet cell antigens, S Antigen, and type II collagen. In one embodiment of the present invention, a patient with an autoimmune disease is treated by administration of a population of T cells generated according to this method. In a related embodiment, the patient is treated with a T cell ablative therapy prior to administering the population of T cells.

The present invention also provides a method for eliminating a clonal B cell population from a population of B cells from an individual, comprising, providing a population of cells wherein at least a portion thereof comprises B cells; exposing the population of cells to one or more pro-apoptotic compositions wherein said exposure induces apoptosis in at least a portion of the B cells; thereby eliminating said portion of B cells from the population. In one embodiment, the method further comprises exposing the remaining population of cells to a surface wherein the surface has attached thereto one or more agents that ligate a cell surface moiety of at least a portion of the remaining B cells and stimulates said remaining B cells. In certain embodiments, the pro-apoptotic composition comprises an autoantigen.

The present invention also provides for compositions of B-cells generated according to the above methods.

In one embodiment of the present invention, a patient with an autoimmune disease is treated with a composition comprising the populations of B-cells generated using the methods of the present invention. In a related embodiment, the patient is treated with a B cell ablative therapy prior to administering the population of B cells.

One aspect of the present invention provides methods for generating a substantially pure population of T cells from a population of T cells from an individual, comprising providing a population of cells wherein at least a portion thereof comprises T cells: exposing the population of T cells ex vivo to a composition that preferentially selects and/or stimulates surface $CD3^+$ and $CD28^+$ molecules, thereby generating a substantially pure population of $CD3^+/CD28^+$ T cells. In a related embodiment the population of pure T cells generated is a substantially pure population of $CD4^+/CD3^+/CD28^+$ T cells. In a related embodiment the population of pure T cells is a substantially pure population of $CD8^+/CD3^+/CD28^+$ T cells.

In one aspect of the invention the purity of the $CD3^+/CD28^+$ T cells is at least 90% pure. In further embodiments, the purity of the $CD3^+/CD28^+$ T cells is 91%, 92%, 93%, 94%, 95%, 96%, 97%, or 98% pure. In another embodiment the purity of the $CD3^+/CD28^+$ T cells is at least 99% pure. In a related embodiment the purity of the $CD3^+/CD28^+$ T cells is at least 99.9% pure. Therefore, one aspect of the present invention is a population of $CD3^+/CD28^+$ T cells comprising less than 10% of CD28− cells. In certain embodiments, the population of $CD3^+/CD28^+$ T cells comprises less than 9%, 8%, 7%, 6%, 5%, 4%, 3%, 2%, 1%, 0.5% or 0.1% contaminating $CD28^-$ T cells.

In one embodiment the $CD3^+$ surface molecule is stimulated using anti-CD3 antibodies and the $CD28^+$ surface molecule is stimulated using anti-CD28 antibodies.

Therefore, the present invention also provides methods for the generation of a substantially pure population of $CD3^+ CD28^+$ T cells, including $CD4^+CD3^+CD28^+$ T cells, and $CD8^+CD3^+CD28^+$ T cells. These T cell populations could then be used in the treatment of people suffering from autoimmune diseases such as, rheumatoid arthritis, multiple sclerosis, insulin dependent diabetes, Addison's disease, celiac disease, chronic fatigue syndrome, inflammatory bowel disease, ulcerative colitis, Crohn's disease, Fibromyalgia, systemic lupus erythematosus, psoriasis, Sjogren's syndrome, hyperthyroidism/Graves disease, hypothyroidism/Hashimoto's disease, Insulin-dependent diabetes (type 1), Myasthenia Gravis, endometriosis, scleroderma, pernicious anemia, Goodpasture syndrome, Wegener's disease, glomerulonephritis, aplastic anemia, paroxysmal nocturnal hemoglobinuria, myelodysplastic syndrome, idiopathic thrombocytopenic purpura, autoimmune hemolytic anemia, Evan's syndrome, Factor VIII inhibitor syndrome, systemic vasculitis, dermatomyositis, polymyositis, pemphigus vulgaris (PV), paraneoplastic pemphigus (PNP), and rheumatic fever.

The present invention further provides a method for activating and expanding a population of T cells by cell surface moiety ligation, comprising providing a population of cells wherein at least a portion thereof comprises T cells, contacting the population of cells with a surface, wherein the surface has attached thereto one or more agents that ligate a cell surface moiety of at least a portion of the T cells and stimulates said T cells, wherein said surface is present at a ratio of said surface to said cells such that at least a substantial portion of at least one population of antigen-specific T cells is deleted after about 8 days of culture. In one embodiment of the invention, the ratio is from about 50:1 to about 5:1. In certain embodiments, the ratio is from about 100:1 to about 2:1. In one embodiment the ratio is at least about 45:1. In certain embodiments, the ratio is at least about 40:1, 35:1, 30:1, 25:1, 20:1, 15:1, 14:1, 13:1, 12:1, 11:1, 10:1, 9:1, 8:1, 7:1, 6:1, 5:1, 4:1, 3:1, or 2:1. In one particular embodiment the ratio is about 5:1.

The present invention provides a method for eliminating at least a substantial portion of a clonal T cell subpopulation from a mixed population of T cells from an individual, comprising, exposing a population of cells, wherein at least a portion thereof comprises T cells, to one or more pro-apoptotic compositions wherein said exposure induces apoptosis in at least a substantial portion of at least one clonal T cell population present in the mixed population of T cells thereby eliminating at least a substantial portion of said clonal T cell population from the mixed population of T cells.

The present invention further provides methods for improved transplant efficacy by administration of XCELLERATED™ T cells following high-dose chemotherapy and autologous stem cell transplantation.

The present invention also provides a method for treating a patient afflicted with an autoimmune disease comprising contacting a population of cells from the patient, wherein at least a portion thereof comprises T cells, with a surface, wherein said surface has attached thereto one or more agents that ligate a cell surface moiety of at least a portion of the T cells and stimulates said T cells, wherein said surface is present at a ratio of said surface to said cells such that at least a substantial portion of at least one population of antigen-specific T cells is deleted after about 8 days of culture; and administering to the patient an effective amount of T cells from (a) such that in vivo homeostatic proliferation is inhibited; thereby treating autoimmune disease. In certain embodiments, the ratio is from about 10:1 to about 5:1.

The present invention further provides a method for treating a patient afflicted with an autoimmune disease comprising contacting a population of cells from the patient, wherein at least a portion thereof comprises T cells, with a surface, wherein said surface has attached thereto one or more agents that ligate a cell surface moiety of at least a portion of the T cells and stimulates said T cells; administering to the patient the T cells of (a) at a dose such that homeostatic proliferation of endogenous T cells is inhibited; thereby treating autoimmune disease.

The present invention also provides a method for treating a patient infected with HIV comprising contacting a population of cells from the patient, wherein at least a portion thereof comprises T cells, with a surface, wherein said surface has attached thereto one or more agents that ligate a cell surface moiety of at least a portion of the T cells and stimulates said T cells, wherein said surface is present at a ratio of said surface to said cells such that at least a substantial portion of HIV-infected T cells is deleted after about 8 days of culture; and administering to the patient an effective amount of T cells from (a) such that in vivo homeostatic proliferation is inhibited; thereby treating the patient infected with HIV.

BRIEF DESCRIPTION OF THE SEVERAL VIEWS OF THE DRAWINGS

FIG. 2 is a dot plot showing an increase in CD25 expression in CMV-activated HLA-A2CMVpp65 antigen-specific T cells.

FIG. 3 is a dot plot showing the upregulation of CD25 on restimulated cells, and the deletion of prestimulated tetramer-positive cells (i.e., CMVpp65-Ag-specific) by the secondary strong stimulation provided by the 3×28 beads. At day 14 post-primary stimulation, cultures were either left unstimulated (Panels A1-A4) or were restimulated using the XCELLERATE™ process with 3×28 beads for 16 hours (Panels B1-B4). CD25 is upregulated on restimulated cells (Panel B2), but tetramer-positive (i.e., CMVpp65-Ag-specific) prestimulated cells were deleted by the secondary strong stimulation provided by the 3×28 beads (Panel B3).

FIG. 4 is a histogram showing the increase in expression of key effector molecules, including CD95, on leukemic B-cells co-cultured with XCELLERATED T Cells™.

DETAILED DESCRIPTION OF THE INVENTION

Figures 1A, 1B:
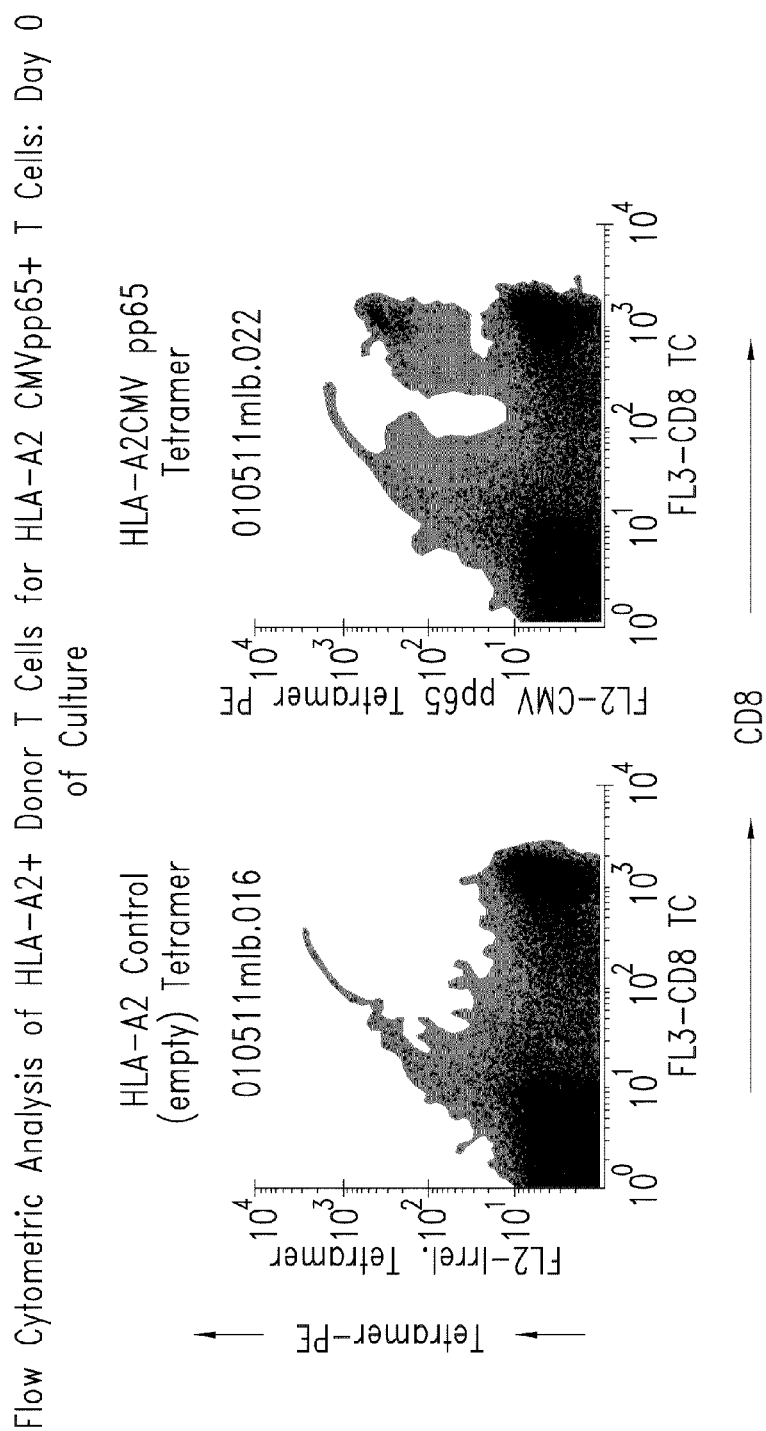
FIG. 1 is a dot plot showing the presence of CD3+CD8+ HLA-A2CMVpp65 antigen specific T cells in an HLA-A2-positive donor.

Prior to setting forth the invention, it may be helpful to an understanding thereof to set forth definitions of certain terms that will be used hereinafter.

The term "biocompatible", as used herein, refers to the property of being predominantly non-toxic to living cells.

The term "stimulation", as used herein, refers to a primary response induced by ligation of a cell surface moiety. For example, in the context of receptors, such stimulation entails the ligation of a receptor and a subsequent signal transduction event. With respect to stimulation of a T cell, such stimulation refers to the ligation of a T cell surface moiety that in one embodiment subsequently induces a signal transduction event, such as binding the TCR/CD3 complex. Further, the stimulation event may activate a cell and up- or down-regulate expression of cell surface molecules such as receptors or adhesion molecules, or up- or down-regulate secretion of a molecule, such as downregulation of Tumor Growth Factor beta (TGF-$\beta$). Thus, ligation of cell surface moieties, even in the absence of a direct signal transduction event, may result in the reorganization of cytoskeletal structures, or in the coalescing of cell surface moieties, each of which could serve to enhance, modify, or alter subsequent cell responses.

The term "activation", as used herein, refers to the state of a cell following sufficient cell surface moiety ligation to induce a measurable morphological, phenotypic, and/or functional change. Within the context of T cells, such activation may be the state of a T cell that has been sufficiently stimulated to induce cellular proliferation. Activation of a T cell may also induce cytokine production and/or secretion, and up- or down-regulation of expression of cell surface molecules such as receptors or adhesion molecules, or up- or down-regulation of secretion of certain molecules, and performance of regulatory or cytolytic effector functions. Within the context of other cells, this term infers either up- or down-regulation of a particular physico-chemical process.

The term "target cell", as used herein, refers to any cell that is intended to be stimulated by cell surface moiety ligation.

An "antibody", as used herein, includes both polyclonal and monoclonal antibodies (mAb); primatized (e.g., humanized); murine; mouse-human; mouse-primate; and chimeric; and may be an intact molecule, a fragment thereof (such as scFv, Fv, Fd, Fab, Fab' and F(ab)'$_2$ fragments), or multimers or aggregates of intact molecules and/or fragments; and may occur in nature or be produced, e.g., by immunization, synthesis or genetic engineering; an "antibody fragment," as used herein, refers to fragments, derived from or related to an antibody, which bind antigen and which in some embodiments may be derivatized to exhibit structural features that facilitate clearance and uptake, e.g., by the incorporation of galactose residues. This includes, e.g., F(ab), F(ab)'$_2$, scFv, light chain variable region ($V_L$), heavy chain variable region ($V_H$), and combinations thereof.

The term "protein", as used herein, includes proteins, glycoproteins and other cell-derived modified proteins, polypeptides and peptides; and may be an intact molecule, a fragment thereof, or multimers or aggregates of intact molecules and/or fragments; and may occur in nature or be produced, e.g., by synthesis (including chemical and/or enzymatic) or genetic engineering.

The term "agent", "ligand", or "agent that binds a cell surface moiety", as used herein, refers to a molecule that binds to a defined population of cells. The agent may bind any cell surface moiety, such as a receptor, an antigenic determinant, or other binding site present on the target cell population. The agent may be a protein, peptide, antibody and antibody fragments thereof, fusion proteins, synthetic molecule, an organic molecule (e.g., a small molecule), or the like. Within the specification and in the context of T cell stimulation, antibodies are used as a prototypical example of such an agent.

The term "cell surface moiety" as used herein may refer to a cell surface receptor, an antigenic determinant, or any other binding site present on a target cell population.

The terms "agent that binds a cell surface moiety" and "cell surface moiety", as used herein, should be viewed as a complementary/anti-complementary set of molecules that demonstrate specific binding, generally of relatively high affinity.

A "co-stimulatory signal", as used herein, refers to a signal, which in combination with a primary signal, such as TCR/CD3 ligation, leads to T cell proliferation and/or activation.

"Separation", as used herein, includes any means of substantially purifying one component from another (e.g., by filtration, affinity, buoyant density, or magnetic attraction).

A "surface", as used herein, refers to any surface capable of having an agent attached thereto and includes, without limitation, metals, glass, plastics, co-polymers, colloids, lipids, cell surfaces, and the like. Essentially any surface that is capable of retaining an agent bound or attached thereto.

"Monoclonality", as used herein, in the context of a population of T cells, refers to a population of T cells that has a single specificity as defined by spectratype analysis (a measure of the TCR V$\beta$, V$\alpha$, V$\gamma$, or V$\delta$ chain hypervariable region repertoire). A population of T cells is considered monoclonal (or mono-specific) when the V$\beta$, V$\alpha$, V$\gamma$, and/or V$\delta$ spectratype profile for a given TCR V$\beta$, V$\alpha$, V$\gamma$, and/or V$\delta$ family has a single predominant peak. Spectratype analysis distinguishes rearranged variable genes of a particular size, not sequence. Thus, it is understood that a single peak could represent a population of T cells expressing any one of a limited number of rearranged TCR variable genes (V$\beta$, V$\alpha$, V$\gamma$, or V$\delta$) comprising any one of the 4 potential nucleotides (adenine (a), guanine (g), cytosine (c), or thymine (t)) or a combination of the 4 nucleotides at the junctional region. In certain embodiments of the present invention, it may be desirable to clone and sequence a particular band to determine the sequence(s) of the rearranged variable gene(s) present in the band representing a particular length.

"Oligoclonality", as used herein, in the context of a population of T cells, refers to a population of T cells that has multiple, but narrow antigen specificity. This can be defined by spectratype analysis (a measure of the TCR V$\beta$, V$\alpha$, V$\gamma$, or V$\delta$) chain hypervariable region repertoire). A population of T cells is considered oligoclonal when the V$\beta$ spectratype profile for a given TCR V$\beta$, V$\alpha$, V$\gamma$, or V$\delta$ family has between about 2 and about 4 predominant peaks. This can also be defined by generation and characterization of antigen-specific clones to an antigen of interest.

"Polyclonality", as used herein, in the context of a population of T cells, refers to a population of T cells that has multiple and broad antigen specificity. This can be by spectratype analysis (a measure of the TCR V$\beta$, V$\alpha$, V$\gamma$, or V$\delta$ chain hypervariable region repertoire). A population of T cells is considered polyclonal when the V$\beta$ spectratype profile for a given TCR V$\beta$, V$\alpha$, V$\gamma$, or V$\delta$ family has multiple peaks, typically 5 or more predominant peaks and in most cases with Gaussian distribution. Polyclonality can also be defined by generation and characterization of antigen-specific clones to an antigen of interest.

"Restoring or increasing the polyclonality", as used herein refers to a shift from a monoclonal profile to an oligoclonal profile or to a polyclonal profile, or from an oligoclonal profile to a polyclonal profile, in expressed TCR Vβ, Vα, Vγ, and/or Vδ genes in a population of T cells, as measured by spectratype analysis or by similar analysis such as flow cytometry or sequence analysis. The shift from a monoclonal Vβ, Vα, Vγ, and/or Vδ expression profile in a population of T cells to an oligoclonal profile or to a polyclonal profile is generally seen in at least one TCR Vβ, Vα, Vγ, and/or Vδ family. In one embodiment of the present invention, this shift is observed in 2, 3, 4, or 5 Vβ families. In certain embodiments of the present invention, a shift is observed in 6, 7, 8, 9, or 10 Vβ families. In a further embodiment of the present invention, a shift is observed in from 11, 12, 13, or 14 Vβ families. In a further embodiment of the present invention, a shift is observed in from 15 to 20 Vβ families. In a further embodiment of the present invention, a shift is observed in 20 to 24 Vβ families. In another embodiment, a shift is seen in all Vβ families. The functional significance of restoring or increasing the polyclonality of a population of T cells is that the immune potential, or the ability to respond to a full breadth of antigens, of the population of T cells is restored or increased. In certain aspects of the present invention, some T cells within a population may not have their TCRs engaged by the methods set forth herein (e.g., T cells with downregulated TCR expression). However, by being in close proximity to T cells activated by the methods described herein, and the factors secreted by them, these T cells may in turn upregulate their TCR expression thereby resulting in a further increase in the polyclonality of the population of T cells. Restoration or increase in polyclonality can also be measured by determining the breadth of response to a particular antigen of interest, for example by measuring the number of different epitopes recognized by antigen-specific cells. This can be carried out using standard techniques for generating and cloning antigen-specific T cells in vitro.

The term "clonal T cell population" as used herein, refers to a T cell population that has a given range of specificities against a given target antigen. This can be measured by any number of assays known in the art, for example by generating and measuring the breadth of specificities (i.e., number of different specificities) of antigen-specific clones in a given population. A clonal T cell population can also be defined by having either monoclonal or oligoclonal specificity as defined by spectratype analysis (a measure of the TCR Vβ, Vα, Vγ, or Vδ chain hypervariable region repertoire).

The term "animal" or "mammal" as used herein, encompasses all mammals, including humans. Preferably, the animal of the present invention is a human subject.

The term "exposing" as used herein, refers to bringing into the state or condition of immediate proximity or direct contact.

The term "proliferation" as used herein, means to grow or multiply by producing new cells.

"Immune response or responsiveness" as used herein, refers to activation of cells of the immune system, including but not limited to, T cells, such that a particular effector function(s) of a particular cell is induced. Effector functions may include, but are not limited to, proliferation, secretion of cytokines, secretion of antibodies, expression of regulatory and/or adhesion molecules, and the ability to induce cytolysis.

"Stimulating an immune response" as used herein, refers to any stimulation such that activation and induction of effector functions of cells of the immune system are achieved.

"Immune response dysfunction" as used herein, refers to the inappropriate activation and/or proliferation, or lack thereof, of cells of the immune system, and/or the inappropriate secretion, or lack thereof, of cytokines, and/or the inappropriate or inadequate induction of other effector functions of cells of the immune system, such as expression of regulatory, adhesion, and/or homing receptors, and the induction of cytolysis.

"Particles" or "surface" as used herein, may include a colloidal particle, a microsphere, nanoparticle, a bead, or the like. A surface may be any surface capable of having a ligand bound thereto or integrated into, including cell surfaces (for example K562 cells), and that is biocompatible, that is, substantially non-toxic to the target cells to be stimulated. In the various embodiments, commercially available surfaces, such as beads or other particles, are useful (e.g., Miltenyi Particles, Miltenyi Biotec, Germany; Sepharose beads, Pharmacia Fine Chemicals, Sweden; DYNABEADS™, Dynal Inc., New York; PURABEADS™, Prometic Biosciences, magnetic beads from Immunicon, Huntingdon Valley, Pa., microspheres from Bangs Laboratories, Inc., Fishers, Ind.).

"Paramagnetic particles" as used herein, refer to particles, as defined above, that localize in response to a magnetic field.

A "pro-apoptotic composition" "apoptotic compositions" or "inducer of apoptosis", as used herein refers to any composition or stimulus that increases the apoptotic activity of a cell either when administered alone or in conjunction with other pro-apoptotic compositions. The pro-apoptotic compositions used in the methods of the present invention preferably induce apoptosis in activated T cells, NKT, NK or B-cells. In certain embodiments, a pro-apoptotic composition of the present invention will induce apoptosis without further activation/stimulation. Illustrative examples of such compositions or stimuli include, but are not limited to, deprivation of a growth factor, oxidizing conditions, heat stress, serum starvation, phorbol myristate acetate (PMA) and ionomycin, superantigens (e.g., SEA, SEB, and the like) various antibodies, such as anti-CD2, anti-CD3, anti-CD28, anti-CD20, anti-Fas antibody, or any combination thereof, MHC-peptide tetramers or dimers, Fas ligand, IL-2, IL-4, TRAIL, rolipram, doxorubicin, chlorambucil, fludarabine, corticosteroids, glucocorticoids, cyclosporine, cyclophosphamide, FK506, azathioprine, methotrexate, mycophenolate, annexin, caspases, inhibitors of bcl-2, topoisomerase inhibitors, interleukin-1β converting enzyme (ICE)-binding agents, *Shigella* IpaB protein, staurosporine, ultraviolet irradiation, gamma irradiation, radiation, tumor necrosis factor, various histone deacetylase inhibitors, and others well known in the art. In certain embodiments, the pro-apoptotic compositions comprises a surface, such as a magnetic bead, having attached thereto one or more agents that binds a cell surface moiety. In this regard, the agent can be any agent as described herein. In one embodiment, the surface has attached thereto at least anti-CD3 antibodies. In another embodiment, the surface has attached thereto anti-CD3 and anti-CD28 antibodies. In addition, a stimulator of apoptosis can be a polypeptide that is capable of increasing or inducing the apoptotic activity of a cell. Such polypeptides include those that directly regulate the apoptotic pathway such as Bax, Bad, Bcl-xS, Bak, Bik, and active caspases as well as those that indirectly regulate the pathway. In certain embodiments, the pro-apoptotic composition comprises activated T cells, such as XCELLERATED T Cells™ (such as those described in U.S. patent application Ser. No. 10/133,236), in particular for inducing apoptosis in populations of B-cells. Other illustrative pro-apoptotic compositions include, but are not limited to, irradiated cells (e.g., donor or recipient (allogeneic) cells), target antigens (e.g., defined autoimmune target antigens for example, in multiple sclerosis, the target antigen identified as myelin basic protein (MBP) MBP 84-102, or MBP 143-168; pancreatic islet cell antigens; in uveitis, the S Antigen; or in rheumatoid arthritis, type II or other types of collagen; in Grave's disease, thyroid receptor; in Myasthena gravis, acetylcholine receptor), cytoplasmic linker protein-170 (CLIP-170), nucleic acid molecules, proteins or peptides, and non-protein or non-polynucleotide compounds.

A "composition that sensitizes cells to further activation or stimulation" or "sensitizing composition" as used herein is any composition which sensitizes cells to subsequent activation/stimulation. Upon subsequent activation/stimulation, sensitized cells undergo apoptosis. Sensitizing compositions of the present invention also sensitize cells to the effects of pro-apoptotic compositions. Illustrative compositions that sensitize cells to further activation, stimulation, or the effects of pro-apoptotic compositions include cells that have been treated such that they are unable to continue dividing, for example by irradiation, (e.g., donor or recipient (allogeneic) cells), superantigens (e.g., SEA, SEB, and the like), target antigens (e.g., defined autoimmune target antigens for example, in multiple sclerosis, the target antigen identified as myelin basic protein (MBP) MBP 84-102, or MBP 143-168; pancreatic islet cell antigens; in uveitis, the S Antigen; or in rheumatoid arthritis, type II or other types of collagen; in Grave's disease, thyroid receptor; in Myasthena gravis, acetylcholine receptor, nucleic acid molecules, proteins or peptides, and non-protein or non-polynucleotide compounds), protein, glycoprotein, peptides, antibody/antigen complexes, cell lysate, non-soluble cell debris, apoptotic bodies, necrotic cells, whole cells from a cell line that have been treated such that they are unable to continue dividing, natural or synthetic complex carbohydrates, lipoproteins, transformed cells or cell line, transfected cells or cell line, or transduced cells or cell line, or any combination thereof.

Apoptosis, for purposes of the present invention, is defined as programmed cell death. Apoptosis is a programmed cell death which is a widespread phenomenon that plays a crucial role in the myriad of physiological and pathological processes. Apoptosis occurs in embryogenesis, metamorphosis, endocrine-dependent tissue atrophy, normal tissue turnover, and death of immune thymocytes (induced through their antigen-receptor complex or by glucocorticoids) (Itoh et al., Cell 66:233, 1991). During maturation of T cells in the thymus, T cells that recognize self-antigens are destroyed through the apoptotic process, whereas others are positively selected. The possibility that some T cells recognizing certain self epitopes (e.g., inefficiently processed and presented antigenic determinants of a given self protein) escape this elimination process and subsequently play a role in autoimmune diseases has been suggested (Gammon et al., Immunology Today 12:193, 1991). Necrosis is an accidental cell death which is the cell's response to a variety of harmful conditions and toxic substances. Apoptosis, morphologically distinct from necrosis, is a spontaneous form of cell death that occurs in many different tissues under various conditions. Apoptosis occurs in two stages. The cell undergoes nuclear and cytoplasmic condensation, and may eventually break into a number of membrane-bound fragments containing structurally intact apoptotic bodies, which are phagocytosed by neighboring cells and rapidly degraded. Alternatively, cells entering the apoptotic pathway may be phagocytosed prior to degeneration into membrane bound bodies. Apoptosis is observed in many different tissues, healthy and neoplastic, adult and embryonic. Death occurs spontaneously, or is induced by physiological or noxious agents. Apoptosis is a basic physiological process that plays a major role in the regulation of cell populations.

Methods for measuring apoptosis are well known in the art. Apoptosis can be determined by methods such as, for example, DNA ladder, electron or light microscopy, flow cytometry, and different commercially available kits for the determination of apoptosis.

As used herein, a "growth inhibiting composition" is any substance that inhibits growth in cells, or otherwise renders cells dysfunctional and unable to divide either when administered alone or in conjunction with other compositions of the present invention. The growth-inhibiting compositions used in the methods of the present invention preferably inhibit growth in activated T cells, NKT, NK or B-cells. Illustrative examples of such compositions or stimuli include, but are not limited to, but are not limited to, deprivation of a growth factor, oxidizing conditions, heat stress, serum starvation, phorbol myristate acetate (PMA) and ionomycin, superantigens (e.g., SEA, SEB, and the like) various antibodies, such as anti-CD2, anti-CD3, anti-CD28, anti-CD20, anti-Fas antibody, or any combination thereof, MHC-peptide tetramers or dimers, Fas ligand, IL-2, IL-4, TRAIL, rolipram, doxorubicin, chlorambucil, fludarabine, corticosteroids, glucocorticoids, cyclosporine, cyclophosphamide, FK506, azathioprine, methotrexate, mycophenolate, annexin, caspases, inhibitors of bcl-2, topoisomerase inhibitors, interleukin-1β converting enzyme (ICE)-binding agents, *Shigella* IpaB protein, staurosporine, ultraviolet irradiation, gamma irradiation, radiation, tumor necrosis factor, various histone deacetylase inhibitors, and others well known in the art. In certain embodiments, the growth inhibiting compositions comprises a surface, such as a magnetic bead, having attached thereto one or more agents that binds a cell surface moiety. In this regard, the agent can be any agent as described herein. In one embodiment, the surface has attached thereto at least anti-CD3 antibodies. In another embodiment, the surface has attached thereto anti-CD3 and anti-CD28 antibodies. In addition, a growth inhibiting composition can comprise a polypeptide that is capable of inhibiting growth of a cell. Such polypeptides include those peptides such as Bax, Bad, Bcl-xS, Bak, Bik, and active caspases. Other illustrative growth inhibiting compositions include, but are not limited to, irradiated cells (e.g., donor or recipient (allogeneic) cells), target antigens (e.g., defined autoimmune target antigens for example, in multiple sclerosis, the target antigen identified as myelin basic protein (MBP) MBP 84-102, or MBP 143-168; pancreatic islet cell antigens; in uveitis, the S Antigen; or in rheumatoid arthritis, type II or other types of collagen; in Grave's disease, thyroid receptor; in Myasthena gravis, acetylcholine receptor), cytoplasmic linker protein-170 (CLIP-170), nucleic acid molecules, proteins or peptides, and non-protein or non-polynucleotide compounds.

As used herein, a "substantially pure" population of $CD3^+$/$CD28^+$ T cells is a population of cells that is comprised of at least about 90% $CD3^+$/$CD28^+$ T cells. In certain aspects of the invention a "substantially pure" population of CD3+/CD28+ T cells is a population of cells that is comprised of at least about 91%, 92%, 93%, 94%, 95%, 96%, 97%, or 98% $CD3^+$/$CD28^+$ T cells, preferably at least about 99%, and even more preferably about 99.9% or more.

Sources of Mixed Population of Cells

In one embodiment, cells to be exposed to the pro-apoptotic or growth inhibiting compositions and/or sensitizing compositions are from the circulating blood of an individual and are obtained from one or more units of blood or from an apheresis or leukapheresis. The apheresis product typically contains lymphocytes, including T cells, monocytes, granulocytes, B cells, other nucleated white blood cells, red blood cells, and platelets. Prior to exposure to a sensitizing composition and subsequent activation and/or stimulation, a source of T cells is obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, thymus, tissue biopsy, tumor, lymph node tissue, gut associated lymphoid tissue, mucosa associated lymphoid tissue, spleen tissue, or any other lymphoid tissue, and tumors. T cells can be obtained from T cell lines and from autologous or allogeneic sources. T cells may also be obtained from a xenogeneic source, for example, from mouse, rat, non-human primate, and pig. In certain embodiments of the present invention, T cells can be obtained from a unit of blood collected from a subject using any number of techniques known to the skilled artisan, such as ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. As those of ordinary skill in the art would readily appreciate a washing step may be accomplished by methods known to those in the art, such as by using a semi-automated "flow-through" centrifuge (for example, the Cobe 2991 cell processor, Baxter) according to the manufacturer's instructions. After washing, the cells may be resuspended in a variety of biocompatible buffers, such as, for example, calcium (Ca)-free, magnesium (Mg)-free PBS. Alternatively, the undesirable components of the apheresis sample may be removed and the cells directly resuspended in culture media.

In another embodiment, T cells are isolated from peripheral blood lymphocytes by lysing or removing the red blood cells and depleting the monocytes, for example, by centrifugation through a PERCOLL™ gradient. A specific subpopulation of T cells, such as $CD28^+$, $CD4^+$, $CD8^+$, $CD45RA^+$, and $CD45RO^+$ T cells, can be further isolated by positive or negative selection techniques. For example, in one preferred embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. For example, $CD3^+$, $CD28^+$ T cells can be positively selected using CD3/CD28 conjugated magnetic beads (e.g., DYNABEADS® M-450 CD3/CD28 T cell Expander). In one aspect of the present invention, enrichment of a T cell population by negative selection can be accomplished with a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8.

An additional aspect of the present invention provides a T cell population or composition that has been depleted or enriched for populations of cells expressing a variety of markers, such as CD62L, CD45RA or CD45RO, cytokines (e.g., IL-2, IFN-γ, IL-4, IL-10), cytokine receptors (e.g., CD25), perforin, adhesion molecules (e.g., VLA-1, VLA-2, VLA-4, LPAM-1, LFA-1), and/or homing molecules (e.g., L-Selectin), prior to sensitization, stimulation and expansion. In one embodiment, cells expressing any of these markers are depleted or positively selected by antibodies or other ligands/binding agents directed to the marker. One of ordinary skill in the art would readily be able to identify a variety of particular methodologies for depleting or positively selecting for a sample of cells expressing a desired marker.

Monocyte populations (i.e., $CD14^+$ cells) may be depleted from blood preparations prior to ex vivo expansion by a variety of methodologies, including anti-CD14 coated beads or columns, or utilization of the phagocytotic activity of these cells to facilitate removal or through adherence to plastic. Accordingly, in one embodiment, the invention uses paramagnetic particles of a size sufficient to be engulfed by phagocytotic monocytes. In certain embodiments, the paramagnetic particles are commercially available beads, for example, those produced by Dynal AS under the trade name DYNABEADS™. Exemplary DYNABEADS™ in this regard are M-280, M-450, and M-500. In one aspect, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be expanded. In certain embodiments the irrelevant beads include beads coated with sheep anti-mouse antibodies, goat anti-mouse antibodies, and human serum albumin.

In brief such depletion of monocytes is performed by pre-incubating PBMC that have been isolated from whole blood using Ficoll, or apheresed peripheral blood with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Preincubation can also be done at temperatures as low as 3-4 degrees C. Such separation can be performed using standard methods available in the art. For example, any magnetic separation methodology may be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD 14 positive cells, before and after said depletion.

T cells for exposure to pro-apoptotic and/or sensitizing compositions and subsequent stimulation may also be frozen after the washing step, which does not require the monocyte-removal step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing a final concentration of 10% DMSO and 4% human serum albumin, or other suitable cell freezing media, the cells then are frozen to −80° C. at a rate of 1° per minute and stored in the vapor phase of a liquid nitrogen storage tank.

Elimination of Undesired Subpopulations of Cells from a Mixed Population of Cells Direct Exposure to Pro-Apoptotic Compositions The present invention provides for methods to eliminate at least a portion of undesired clonal populations of cells, typically T cells, B cells, NKT, or NK cells, from a population of immune cells. The present invention further provides for compositions comprising populations of cells that no longer contain undesired cells, or have a significantly reduced number of undesired cells, and uses thereof.

Undesired populations of cells can be eliminated or reduced by a statistically significant amount directly through the exposure of said cells to a pro-apoptotic composition. Exposure to the pro-apoptotic composition can take place in vivo or in vitro. Without being bound by theory, the previously activated cells are thought to be more sensitive to apoptotic compositions than naïve or unactivated cells. Therefore, exposure to apoptotic compositions either in vivo or in vitro, using doses and conditions that induce apoptosis, will selectively kill highly activated cells such as unwanted autoreactive cells in a patient. In preferred embodiments of the present invention, the autoreactive cells to be eliminated comprise T cells, NKT, NK, or B cells.

Thus, the present invention provides methods for the elimination of at least a substantial portion of any unwanted subpopulation of clonal cells (such as T, B, NKT, or NK cells) from a mixed population of immune cells. For the purposes of the present invention, a substantial portion means at least 70% of the unwanted subpopulation of cells. In certain embodiments, a substantial portion means 75%, 80%, 85%, 90%, 95%, 96%, 97%, 98%, 99% and higher of the unwanted subpopulation of cells. Elimination of cells can be measured using any number of techniques known in the art, including but not limited to flow cytometric analysis using a variety of antibodies and/or peptide-MHC tetramers and functional assays such as proliferation and chromium release assays.

Pro-apoptotic compositions or inducers of apoptosis refers to any composition or stimulus that increases the apoptotic activity of a cell either when administered alone or in conjunction with (in combination with, before or after) other pro-apoptotic compositions. The pro-apoptotic compositions used in the methods of the present invention preferably induce apoptosis in activated T cells, NKT cells, NK cells, and B cells. The amount and conditions under which the pro-apoptotic compositions induce desired apoptosis may vary and can be determined by the skilled artisan using routine optimization. In certain embodiments, a pro-apoptotic composition of the present invention will induce apoptosis without further activation/stimulation. Illustrative examples of such agents or stimuli include, but are not limited to, deprivation of a growth factor, oxidizing conditions, heat stress, freeze-thaw stress, serum starvation, various antibodies, such as anti-CD2, anti-CD3, anti-CD28, anti-CD20, or anti-Fas antibody; MHC-peptide tetramers; Fas ligand, TRAIL, FR901228 (as described in U.S. Pat. No. 6,403,555), FK506, annexin, caspases, cytokines such as IL-2 or IL-4, cyclophosphamide, chemotherapeutic agents, UV, steroids, corticosteroids, glucocorticoids, rolipram, doxorubicin, chlorambucil, fludarabine, inhibitors of bcl-2, topoisomerase inhibitors, interleukin-1β converting enzyme (ICE)-binding agents, *Shigella* IpaB protein, staurosporine, ultraviolet irradiation, gamma irradiation, radiation, tumor necrosis factor, histone deacetylase inhibitors, and others well known in the art. In certain embodiments, the pro-apoptotic composition comprises a surface, such as a magnetic bead, having attached thereto one or more agents that binds a cell surface moiety. In this regard, the agent can be any agent as described herein. In one embodiment, the surface has attached thereto at least anti-CD3 antibodies. In another embodiment, the surface has attached thereto anti-CD3 and anti-CD28 antibodies. In addition, a stimulator of apoptosis can be a polypeptide that is capable of increasing or inducing the apoptotic activity of a cell. Such polypeptides include those that directly regulate the apoptotic pathway such as Bax, Bad, Bcl-xL, Bak, Bik, and active caspases as well as those that indirectly regulate the pathway. Other illustrative pro-apoptotic compositions include, but are not limited to, irradiated cells (e.g., donor or recipient (allo) cells), target antigens (e.g., defined autoimmune target antigens such as myelin basic protein (MBP), pancreatic islet cell antigens, cytoplasmic linker protein-170 (CLIP-170), Sjogren's syndrome antigen A (SS-A/Ro), Sjogren's syndrome antigen B (SS-B/La), Sjogren's lupus antigen (SL), scleroderma antigen 70 (Scl-70)) nucleic acid molecules, proteins or peptides, and non-protein or non-polynucleotide compounds.

In one aspect of the present invention, one or more pro-apoptotic compositions is administered to an individual in vivo in conjunction with a pharmaceutically acceptable excipient. Any combination of pro-apoptotic compositions may be administered, such as anti-CD3 antibodies, in conjunction with a cytokine such as IL-2 or IL-4, administration of which is described in patent application number WO9428926. As the skilled artisan will readily recognize, tests on any pro-apoptotic composition used in the methods of the present invention would need to be routinely carried out over a range of doses to determine: 1) the pharmacokinetic behavior of these substances; and 2) safety and identification of any untoward effects 3) optimal doses for effective induction of apoptosis in cells to be eliminated. This would constitute a Phase I clinical trial. Thus, the particular pro-apoptotic compositions employed in the methods described herein would require individual routine optimization. The pro-apoptotic compositions of the present invention can be administered topically, parenterally, or by inhalation. The term "parenteral" includes subcutaneous injections, intravenous, intramuscular, intracisternal injection, or infusion techniques. These compositions will typically contain an effective amount of the pro-apoptotic composition, alone or in combination with an effective amount of any other active material. Such dosages and desired drug concentrations contained in the compositions may vary depending upon many factors, including the intended use, mammal's body weight and age, and route of administration. Preliminary doses can be determined according to animal tests, and the scaling of dosages for human administration can be performed according to art-accepted practices.

In one aspect of the present invention, the population of cells is exposed to one or more pro-apoptotic compositions in vitro. As the skilled artisan will readily recognize, tests on any pro-apoptotic composition used in the methods of the present invention would need to be routinely carried out over a range of doses to determine: 1) the behavior of these substances; and 2) safety and identification of any untoward effects 3) optimal doses for effective induction of apoptosis in cells to be eliminated. Thus, the particular pro-apoptotic compositions employed in the methods described herein would require individual routine optimization. In one particular embodiment, the population of remaining cells that has been cleared of unwanted reactive subpopulations of cells can then be administered to the patient without further stimulation/activation or expansion.

In one embodiment of the present invention, cells are exposed to pro-apoptotic compositions multiple times either alone or in combination with other pro-apoptotic compositions. In certain aspects of the present invention, it may be preferable to activate/stimulate and in some cases also expand a mixed population of cells as described below in the sections entitled "Stimulation/Activation of Cell Populations" and "Expansion of Cell Populations" prior to exposure to one or more pro-apoptotic compositions. In one preferred embodiment, the cells remaining in the population following exposure to a pro-apoptotic compositions of the present invention, are activated/stimulated and expanded in vitro as described below in the sections entitled "Stimulation/Activation of Cell Populations" and "Expansion of Cell Populations". In certain embodiments, the pro-apoptotic composition and the composition used to activate/stimulate and expand are the same composition. In one particular embodiment, a surface having attached thereto an agent, as described herein, is used as a pro-apoptotic composition and further, used to active/stimulate and expand a mixed population. In this regard, certain clonal cells in the population are induced to undergo apoptosis while others are stimulated/activated and proliferate in response to the composition. In this context, an illustrative composition that can be used both to induce apoptosis in a subpopulation of T cells and to stimulate/activate and expand a mixed population of T cells comprises anti-CD3 and anti-CD28 antibodies co-immobilized on beads (3×28 beads).

In another embodiment of the present invention, the cells remaining following exposure to one or more pro-apoptotic compositions, are further stimulated/activated and expanded in vivo. In vivo stimulation and expansion of the cells of the present invention can be carried out using any number of cytokines, such as IL-2 and IL-4 or other agents described herein that simulate cells.

In a further embodiment of the present invention, the cells remaining following exposure to one or more pro-apoptotic compositions, are further stimulated/activated and expanded in vitro using the surfaces and agents bound thereto as described below in the sections entitled "Stimulation/Activation of Cell Populations" and "Expansion of T cell Populations". The stimulation and activation of the remaining cells that have not undergone apoptosis using the surfaces of the present invention, can increase polyclonality of said remaining population of T cells as measured by the breadth of the response of the population to a given antigen. Restoration or increase in polyclonality can be measured by determining the breadth of response to a particular antigen of interest, for example by measuring the number of different epitopes recognized by antigen-specific cells. This can be carried out using standard techniques for generating and cloning antigen-specific T cells in vitro.

The stimulation and activation using the surfaces of the present invention of the remaining cells that have not undergone apoptosis, restores polyclonality to said remaining population of T cells with respect to expressed TCR genes as indicated by spectratype analysis. Polyclonality of the T cell compositions of the present invention are as described in U.S. Patent Application No. 60/375,733. Spectratype analysis is a method for measuring TCR Vβ, Vα, Vγ, or Vδ gene usage by a pool of T cells and levels of nucleotide insertion during the recombination process in T cell development (as described in U.S. Pat. No. 5,837,447). Spectratype analysis can be used to measure the breadth or narrowness of the T cell immune response potential. Additionally, spectratype analysis can be used to determine if specific undesired clonal populations of T cells have been removed from a mixed population of T cells.

The ability of V, D, and J gene segments to combine together randomly introduces a large element of combinatorial diversity into the TCR repertoire. The precise point at which V, D, and J segments join can vary, giving rise to local amino acid diversity at the junction. The exact nucleotide position of joining can differ by as much as 10 residues resulting in deletion of nucleotides from the ends of the V, D, and J gene segments, thereby producing codon changes at the junctions of these segments. Diversity is further increased during the rearrangement process when additional nucleotides not encoded by either gene segment are added at the junction between the joined gene segments. (The variability created by this process is called "N-region diversity.") (Janeway, Travers, Walport. Immunobiology. Fourth Ed., 98 and 150. Elsevier Science Ltd/Garland Publishing. 1999).

The level of diversity for the T cell repertoire can be measured, in part, by evaluating which TCR Vβ, Vβ, Vγ, or Vδ chains are being employed by individual T cells within a pool of circulating T cells, and by the number of random nucleotides inserted next to the Vβ gene at the V-D-J or V-J gene junctions. In general, when the circulating T cell pool contains T cells expressing the full range of TCR Vβ, Vα, Vγ, or Vδ chains and when those individual V region chains are derived from gene recombination events which utilize the broadest array of inserted nucleotides, the T cell arm of the immune system will have its greatest potential for recognizing the universe of potential antigens. When the range of TCR V region chains expressed by the circulating pool of T cells is limited or reduced, and when expressed TCRs utilize chains encoded by recombined genes with limited nucleotide insertions, the breadth of the immune response potential is correspondingly reduced. The consequences of this are a reduced ability to respond to the wide variety of antigens leading to increased risks of infection and cancer.

Methods for determining apoptosis are known in the art and are described, for example, in *Current Protocols in Immunology*, John Wiley & Sons, New York, N.Y., or in U.S. Pat. No. 6,312,684. Illustrative assays to measure apoptosis comprise DNA ladder, electron or light microscopy, flow cytometry, and different commercially available kits for the determination of apoptosis. In certain embodiments, cells are observed for morphological changes, such as chromatin condensation, cell shrinkage, increased granularity and other indicia of apoptosis known to those of skill in the art. Chromatin condensation can be detected by standard methods, such as light microscopy of stained cell preparations. Cell shrinkage and granularity can be readily detected by measuring the light scattering properties of the cells (Kerr, et al. supra., and Wyllie, et al., supra). Observation of single or double stranded fragmentation of DNA into oligonucleosomal ladders often is another indication that apoptosis has been induced (Arend, et al., *Am. J. Pathol,* 136:593, 1990; Wyllie, et al., *J. Pathol,* 142:67, 1984). Sometimes, however, apoptotic cells do not exhibit double stranded internucleosomal DNA fragmentation (Collins, et al., *Int. J. Rad. Biol.,* 62:45 1992; Cohen, et al., *Biochem. J.,* 286:331 1992); instead, single DNA strand breaks will be observed. Single-strand breaks can readily be detected using a method of in situ nick end-labeling of the DNA. This method is described by Wyllie, et al. (*Br. J. Cancer,* 67:20, 1993).

In one embodiment, the cells of the present invention are exposed to a growth inhibiting composition as described herein. In certain embodiments, the growth inhibiting compositions of the present invention inhibit growth in at least a substantial portion of at least one clonal population of T cells such that when a mixed population of cells is activated/stimulated and expanded as described herein, the growth inhibited cells do not expand and are eventually out-competed by the mixed population of cells. The end result of this being the effective elimination of the growth inhibited cells from the mixed population of cells.

Exposure to Compositions that Sensitize Cells to Further Stimulation/Activation

Alternatively, at least a substantial portion of an undesired population of cells can be eliminated by first sensitizing the cells to further stimulation/activation and then further simulating or activating them by exposure to a surface of the present invention. This additional stimulation/activation induces apoptosis in the sensitized cells, leading to their elimination from the population. The sensitizing compositions of the present invention also sensitize cells to the effects of pro-apoptotic compositions described above. Thus, the present invention provides for methods to eliminate at least a substantial portion of an undesired clonal population of cells, typically T cells or B cells, from a population of immune cells by exposure to one or more compositions that sensitize the undesired populations of cells to further stimulation/activation or to the effects of a pro-apoptotic composition. The present invention further provides for compositions comprising populations of cells that no longer contain undesired cells, and uses thereof.

In one embodiment, exposure to a composition that sensitizes to further activation or stimulation occurs naturally in vivo, such as in the setting of autoimmune diseases. In this regard, autoimmune cells are exposed to autoantigen in vivo and are thus sensitized. Upon further stimulation/activation, such as by using the methods of the present invention using a surface as described herein (e.g., a surface having attached thereto one or more agents that ligate a cell surface moiety, such as anti-CD3 and anti-CD28 antibodies), these autoimmune cells are induced to undergo apoptosis.

In one aspect of the present invention, a population of immune cells is exposed to a composition or compositions that sensitize to further activation or stimulation, at least a portion of cells, e.g., previously highly activated T cells or B cells. In a preferred embodiment, the sensitized cells comprise undesired autoreactive T or B cells (e.g., in the setting of multiple sclerosis, such sensitized cells would comprise MBP-specific T cells that are sensitized in vivo as a results of the aberrant immune regulation associated with this disease). In a further embodiment, the sensitized cells comprise alloreactive cells present in donor hematopoietic stem cell. In yet a further embodiment, the sensitized cells comprise alloreactive cells from a potential organ transplant recipient.

In one embodiment of the present invention, the sensitizing composition comprises irradiated cells. In a particular embodiment, the irradiated cells are from a hematopoietic stem cell transplant recipient and the cells to be sensitized are from the hematopoietic stem cell transplant donor. In another embodiment, the sensitizing composition comprises irradiated cells from an organ donor and the cells to be sensitized are cells from the organ recipient. In certain embodiments, the cells to be sensitized are cells from an organ recipient post-transplant. Cells are typically irradiated with gamma rays in the range of about 3000 to 3600 rads, more preferably at about 3300 rads. Other irradiated cells that may be useful in the present invention, such as lymphoblastoid or tumor cell lines are typically irradiated with gamma rays in the range of about 6000 to 10,000 rads, more preferably at about 8000 rads. Cells may also be treated by other means such as with chemical agents (e.g., etiposide, mitomycin, and the like).

Sensitizing compositions of the present invention include any composition or combination of compositions that sensitizes immune cells, such as T, NKT, NK, or B cells, to subsequent stimulation such that subsequent stimulation or activation induces apoptosis. Sensitizing compositions of the present invention also include any composition or combination of compositions that sensitizes immune cells, such as T or B cells, to subsequent exposure to a pro-apoptotic composition. Sensitizing compositions of the present invention include but are not limited to antibodies such as anti-CD2, anti-CD3, anti-FAS; MHC-peptide dimers or tetramers, cytokines such as IL-2, TRAIL, compounds such as rolipram, doxorubicin, chlorambucil and fludarabine. Sensitizing compositions also include FAS-ligand and the natural ligands for CD2 and CD3. Sensitizing compositions also include inhibitors of bcl-2, such as those described in U.S. Pat. No. 6,277,844, topoisomerase inhibitors, such as etoposide, CPT-11 and topotecan, and others, such as described in U.S. Pat. No. 5,834,012. Other illustrative sensitizing compositions include interleukin-1β converting enzyme (ICE)-binding agents that induce apoptosis, such as *Shigella* IpaB protein described in U.S. Pat. No. 5,972,899, or compounds described in U.S. Pat. Nos. 6,350,741, 6,294,546 and 6,329,365.

Illustrative sensitizing compositions of the present invention also comprise autoantigens. Autoantigens may be defined autoimmune target antigens e.g., defined autoimmune target antigens for example, in multiple sclerosis, the target antigen identified as myelin basic protein (MBP) MBP 84-102, or MBP 143-168; pancreatic islet cell antigens; in uveitis, the S Antigen; or in rheumatoid arthritis, type II or other types of collagen; in SLE, cytoplasmic linker protein-170 (CLIP-170); Sjogren's syndrome antigen A (SS-A/Ro), Sjogren's syndrome antigen B (SS-B/La), Sjogren's lupus antigen (SL); scleroderma antigen 70 (Scl-70); in Grave's disease, thyroid receptor; in Myasthena gravis, acetylcholine receptor, nucleic acid molecules, proteins or peptides, and non-protein or non-polynucleotide compounds. Autoantigens of the present invention also comprise peptide mixtures eluted from MHC molecules known to be associated with autoimmunity, for example, HLA-DQ and -DR molecules that confer susceptibility to several common autoimmune diseases, such as type 1 diabetes, rheumatoid arthritis and multiple sclerosis, or HLA-B27 molecules known to confer susceptibility to reactive arthritis and ankylosing spondylitis. Autoantigens of the present invention may also be synthesized peptides predicted to bind to MHC molecules associated with autoimmune diseases. It should be noted that sensitization may occur naturally as a process of autoimmune disease. As such, the "pre sensitized" autoreactive (autoantigen-specific) T cells exist in patients and can be eliminated or otherwise substantially reduced directly through the XCEL-LERATE™ process as described herein.

The present invention further provides sensitizing compositions for selectively eliminating at least a substantial portion of a population of T cells expressing a specific Vβ, Vα, Vγ, or Vδ gene. For example, antibodies specific for a particular Vβ, Vα, Vγ, or Vδ gene can be used to specifically sensitize the T cells according to the methods of the present invention. Alternatively, T cells expressing a particular Vβ, Vα, Vγ, or Vδ gene of interest can be negatively selected, thereby eliminating at least a substantial portion of them from a population.

In further embodiments of the present invention, one or more sensitizing compositions are used simultaneously and for times sufficient to induce the desired sensitization.

As described above with pro-apoptotic compositions, the present invention provides for methods wherein compositions that sensitize cells to further stimulation/activation or the effects of pro-apoptotic compositions, are administered in vivo or in vitro, or a combination of the two. As with any medicinal substance, or biologic, tests on any agents that sensitize cells to further stimulation/activation to be administered in vivo, such as numerous pro-apoptotic compounds, antibodies, peptides and proteins used for immunization would need to be routinely carried out over a range of doses to determine: 1) the pharmacokinetic behavior of these substances; 2) their immunogenicity; and 3) safety and identification of any untoward effects. This would constitute a Phase I clinical trial. Thus, the particular agents that sensitize cells to further stimulation/activation employed in the methods of the present invention (for example, in multiple sclerosis, the target antigen identified as MBP 84-102, or MBP 143-168; in uveitis, the S Antigen; or in rheumatoid arthritis, type II collagen) would require individual routine optimization. The sensitizing compositions of the present invention can be administered topically, parenterally, or by inhalation. The term "parenteral" includes subcutaneous injections, intravenous, intramuscular, intracisternal injection, or infusion techniques. These compositions will typically contain an effective amount of the sensitizing composition, alone or in combination with an effective amount of any other active material. Such dosages and desired drug concentrations contained in the compositions may vary depending upon many factors, including the intended use, mammal's body weight and age, and route of administration. Preliminary doses can be determined according to animal tests, and the scaling of dosages for human administration can be performed according to art-accepted practices.

Ample evidence from the development of vaccines suggests that either synthetic peptides or recombinant DNA-derived proteins are effective in eliciting an immune response in humans. These studies also provide guidance as to the range of doses effective for immunization (Zajoc, B. A., D. J. West, W. J. McAleer and E. M. Scolnick, Overview of clinical studies with Hepatitis B vaccine made by recombinant DNA, *J. Infect.* 13:(Suppl A)39-45 (1986).Yamamoto, S., T. Kuroki, K. Kurai and S. Iino, Comparison of results for phase I studies with recombinant and plasma-derived hepatitis B vaccines, and controlled study comparing intramuscular and subcutaneous injections of recombinant hepatitis B vaccine, *J. Infect.* 13:(Suppl A)53-60 (1986). Francis, D. P. et al., The prevention of Hepatitis B with vaccine, *Ann. Int. Med.* 97:362-366 (1982). Putney et al., Features of HIV envelope and development of a subunit vaccine, AIDS Vaccine Research and Clinical Trials, S. Putney and B. Bolognesi, eds. (New York: Dekker) pp. 3-62 (1990). Steven, V. C. and W. R. Jones, Vaccines to prevent pregnancy, New Generation Vaccines, G. C. Woodrow and M. M. Levine, eds. (New York: Dekker) pp. 879-900 (1990). Herrington et al., Safety and immunogenicity in man of a synthetic peptide malaria vaccine against *Plasmodium Falciparium* sporozoites, *Nature,* 328:257-259 (1987)).

In one embodiment of the present invention, immunization (i.e., in vivo sensitization) with an agent that sensitizes cells to further stimulation/activation or exposure to a pro-apoptotic composition, is then followed by a waiting period during which the agent activates the subset of cells bearing reactive receptors, such as T cells bearing reactive TCRs or B cells expressing specific antibody receptors, causing them to express cytokine receptors, such as the IL-2 receptor. For example, this process will induce IL-2 receptors only on T cells that have been antigenically-stimulated. Based on studies of both human and mouse T cells in vitro, between about 12 to about 24 hours after antigen exposure are required to express significant numbers of IL-2 receptors, and as long as about 72 hours are required to express optimal numbers of IL-2 receptors on the majority of T cells. Thus, the waiting period can be as short as about 12 hours or as long as about 72 hours, and in the case of various disease states, due to retarded immune responsiveness, this period may be as long as 120 hours, becoming increasingly optimal toward the upper end of this range.

In one embodiment of the present invention, IL-2, or other appropriate cytokines, such as IL-4, are administered to the patient to induce apoptosis in the activated cells as described above. Administration of IL-2 to humans has been well-studied in cancer patients, and various doses have been evaluated (Loize, M. T., L. W. Frana, S. O, Sharrow, R. J. Robb and S. A. Rosenberg, In vivo administration of purified human interleukin 2. I. Half-life and immunologic effects of the Jurkat cell line-derived interleukin 2. *J. Immunol.* 134:157-166 (1985). Lotze, J. T., Y. L. Malory, S. E. Ettinghausen, A. A. Rayner, S. O, Sharrow, C. A. Y. Seipp, M. C. Custer and S. A. Rosenberg, In vivo administration of purified human interleukin 2. II. Half-life, immunologic effects, and expansion of peripheral lymphoid cells in vivo with recombinant IL 2. *J. Immunol.* 135:2865-2875 (1985). Donahue, J. H. and S. A. Rosenberg, The fate of interleukin-2 after in vivo administration, *J. Immunol.* 130:2203-2208 (1983). Belldegrun, A., M. M. Muul and S. A. Rosenberg, Interleukin 2 expanded tumor-infiltrating lymphocytes in human renal cell cancer: isolation, characterization, and antitumor activity, *Cancer Research* 48:206-214 (1988). Rosenberg, S. A., M. T. Lotze, L. M. Muul, S. Leitman, A. E. Chang, S. E. Ettinghausen, Y. L. Malory, J. M. Skibber, E. Shiloni, J. T. Vetto, C. A. Seipp, C. Simpson and C. M. Reichert, Observations on the systemic administration of autologous lymphokine-activated killer cells and recombinant interleukin-2 to patients with metastatic cancer, *New Eng. J. Med.* 313:1485-1492 (1985).). Data indicate that IL-2 should be given I.V., either as frequent bolus doses or as a continuous infusion. Doses that have been previously established range between about 300 to about 3000 units/kg/hour continuous infusion, or from 104 to 106 units/kg I.V. bolus.

In one aspect of the present invention, the population of cells is exposed to one or more sensitizing compositions in vitro. As the skilled artisan will readily recognize, tests on any sensitizing composition used in the methods of the present invention would need to be routinely carried out over a range of doses to determine: 1) the pharmacokinetic behavior of these substances; and 2) safety and identification of any untoward effects 3) optimal doses for effective induction of apoptosis in cells to be eliminated. Thus, the particular sensitizing compositions employed in the methods described herein would require individual routine optimization.

In one embodiment of the present invention, cells are collected from an individual previously treated in vivo with an agent that sensitizes cells to further stimulation/activation. Cells are then further stimulated/activated to induce apoptosis and then expanded in vitro as described below.

Stimulation of Sensitized Cells to Induce Apoptosis of Cells to be Eliminated from a Mixed Population of Cells In one aspect of the present invention, a population of immune cells comprising sensitized cells as described above is further activated or stimulated to induce apoptosis as described below in the section entitled "Stimulation/Activation of Cell Populations", thereby eliminating the sensitized cells, such as autoreactive or alloreactive T- or B-cells, from the mixed population of cells. At the same time, the desired cells that remain, e.g., those cells that are not sensitized to undergo apoptosis, are activated and stimulated to expand, thereby resulting in a population of activated cells from which at least a substantial portion of unwanted subpopulations of T (or B cells) have been eliminated. As mentioned previously, stimulation/activation as described herein may be carried out on cells remaining following exposure of a mixed population of cells directly to pro-apoptotic compositions. Furthermore, the subsequent stimulation and activation provided by the present invention restores polyclonality to the population of T cells with respect to expressed TCR genes as indicated by spectratype analysis.

In one embodiment of the present invention, sensitized cells are stimulated/activated as described below multiple times with or without additional sensitizing composition, as many times as is necessary to eliminate at least a substantial portion of the undesired cells. For example in the setting of an autoimmune disease, the present invention provides for methods to stimulate cells a second or more times in the presence of antigen (i.e., sensitizing composition) after the initial round of stimulation/activation. Likewise, in the setting of hematopoietic stem cell transplantation, the present invention provides for methods to stimulate cells from the hematopoietic stem cell donor a second or more times, or as many times as necessary to eliminate at least a substantial portion of the undesired cells, in the presence of irradiated cells from a hematopoietic stem cell transplant recipient. In the setting of organ transplantation, the present invention provides for methods to stimulate cells from the organ recipient a second or more times, or as many times as is necessary to eliminate at least a substantial portion of undesired cells, if necessary in the presence of irradiated cells from the organ donor. In one embodiment, the methods of the present invention are carried out on cells from a patient (e.g., host cells) post-transplant in order to eliminate undesired cells. In certain embodiments, it may not be necessary to eliminate all of the undesired cells, for example in the setting of hematopoietic stem cell transplantation for certain types of cancer, graft versus leukemic cell effect may be desired.

In certain aspects of the present invention, it may be preferable to stimulate/activate and in some cases expand a mixed population of cells as described below in the sections entitled "Stimulation/Activation of Cell Populations" and "Expansion of Cell Populations" prior to exposure to one or more agents that sensitize cells to further stimulation/activation and subsequent stimulation.

In further aspects of the present invention, the cells are sensitized and then exposed to a pro-apoptotic composition, thereby eliminating at least a substantial portion of cells that have become sensitized to the effects of the pro-apoptotic composition. The cells remaining in the population can then be further stimulated/activated and expanded as described below.

In one embodiment, the cells of the present invention are exposed to a growth inhibiting composition as described herein. In certain embodiments, the growth inhibiting compositions of the present invention inhibit growth in at least a substantial portion of at least one clonal population of T cells such that when a mixed population of cells is activated/stimulated and expanded as described herein, the growth inhibited cells do not expand and are eventually out-competed by the mixed population of cells. The end result of this being the effective elimination of the growth inhibited cells from the mixed population of cells.

Generation of a Substantially Pure CD3$^+$CD28$^+$ T Cell Population

The present invention provides methods for the generation of a substantially pure population of CD3$^+$CD28$^+$ T cells from a population of immune cells. For the purposes of the present invention, a population of substantially pure CD3$^+$CD28$^+$ T cells contains less than 10% CD3$^+$CD28$^-$ T cells. In certain embodiments, a population of substantially pure CD3$^+$CD28$^+$ T cells contains less than 9%, 8%, 7%, 6%, 5%, 4%, 3%, 2%, 1%, 0.5%, or 0.1% CD3$^+$CD28$^-$ T cells A pure population of CD3$^+$CD28$^+$ T cells can be generated by magnetic concentration, selection, and stimulating the mixed population of T cells with a composition capable of stimulating both CD3 and CD28 molecules on the surface of a T cell. Selection and stimulation of both the CD3 and CD28 molecules on the surface of a cell results in the activation and proliferation of this subset of cells. Conversely, under conditions described herein, exposure of a CD3$^+$CD28$^-$ T cell to a composition capable of selecting and stimulating both CD3 and CD28 surface molecules would be insufficient to induce both activation and expansion of this population of T cells. Further, shortening incubation time with CD3/CD28 beads as described herein, favors selection of CD3$^+$CD28$^+$ cells at the expense of CD3$^+$CD28$^-$ cells (e.g., a 15 minute selection at 1 r.p.m. at room temperature, followed by magnetic concentration leaves many or most CD3$^+$CD28$^-$ cells behind.) Thus, in one embodiment, a short incubation with a surface as described herein followed by a short magnetic selection is used to preferentially select or enrich for CD28$^+$ T cells while leaving CD28$^-$ cells behind. Further the temperature of incubation, the rate of mixing during the incubation, and the exposure to the magnetic field, can all be varied to preferentially select for CD28$^+$ cells. In certain embodiments, antibodies other than anti-CD28 or in conjunction with anti-CD28 can be used, for example anti-NKG2D antibody.

Triggering of the TCR by either a specific antigen or by a molecule capable of stimulating the CD3 surface molecule, for example an anti-CD3 antibody, is considered insufficient to induce expansion and lymphokine secretion unless supplemented by co-stimulatory signals, i.e., the specific stimulation of the CD28 molecule. In fact, in the absence of co-stimulation, these T cells may acquire a state of non-responsiveness or anergy.

Thus, the methods of the present invention, e.g., the stimulation and selection of a mixed population of T cells using a composition capable of triggering CD3 and simulating CD28, would result in the generation of a substantially pure population of CD3$^+$CD28$^+$ T cells In certain embodiments, it may be desirable to use the CD28$^-$ population of T cells. Without being bound by theory, this population may contain T cells, such as tumor-specific, or virus-specific T cells of interest that could be enriched and used for therapy as described herein, either as is or following further culture/expansion.

In one embodiment of the present invention, this population of substantially pure CD3$^+$CD28$^+$ T cells can be used to treat acute or chronic GVHD. In other embodiments, a population of substantially pure CD3$^+$CD28$^+$ T cells can be used to treat autoimmune diseases, such as rheumatoid arthritis, multiple sclerosis, insulin dependent diabetes, Addison's disease, celiac disease, chronic fatigue syndrome, colitis, Crohn's disease, fibromyalgia, lupus, psoriasis, Sjogren's syndrome, hyperthyroidism/Graves disease, hypothyroidism/Hashimoto's disease, insulin-dependent diabetes (type 1), Myasthenia Gravis, endometriosis, scleroderma, pernicious anemia, Goodpasture syndrome, Wegener's disease and rheumatic fever. In a further embodiment, the cells of the present invention can be used to treat autoimmunity associated with large granular lymphocyte leukemia (LGL). A mixed population of immune cells could be removed from a donor and these cells stimulated with a composition capable of stimulating CD3 and CD28 molecules. While not wanting to be bound by theory, it is postulated that this stimulation results in the specific activation and expansion of CD3$^+$CD28$^+$ T cells, and result in the anergy of T cells that lack the expression of the co-stimulatory molecule, CD28. Once the pure population of CD3$^+$CD28$^+$ T cells has been generated, these cells can then be infused for the treatment of an autoimmune disease, LGL, or GVHD.

Stimulation/Activation of Cell Populations

The stimulated and activated T cells of the present invention are generated by cell surface moiety ligation that induces activation. In certain embodiments, the stimulated and activated T cells are generated by activating a population of T cells solely via engagement of the TCR, for example using anti-TCR antibodies, anti-CD3 antibodies, or natural ligands for the TCR. In certain embodiments, the stimulated and activated T cells are generated by activating a population of T cells and stimulating an accessory molecule on the surface of the T cells with a ligand which binds the accessory molecule, as described for example, in U.S. patent application Ser. Nos. 08/253,694, 08/435,816, 08/592,711, 09/183,055, 09/350,202, 09/252,150, 10/133,236, 10/187,467, 10/350,305, published PCT application WO03024989, and U.S. Pat. Nos. 6,352,694, 5,858,358 and 5,883,223. In the context of sensitized cells described above, activating said sensitized population of T cells and stimulating an accessory molecule on the surface of said sensitized T cells with a ligand which binds the accessory molecule induces apoptosis and subsequent elimination of the cells.

Generally, T cell activation of cells may be accomplished by cell surface moiety ligation, such as stimulating the T cell receptor (TCR)/CD3 complex or the CD2 surface protein. A number of anti-human CD3 monoclonal antibodies are commercially available, exemplary are, clone BC3 (XR-CD3; Fred Hutchinson Cancer Research Center, Seattle, Wash.), OKT3, prepared from hybridoma cells obtained from the American Type Culture Collection, and monoclonal antibody G19-4. Similarly, stimulatory forms of anti-CD2 antibodies are known and available. Stimulation through CD2 with anti-CD2 antibodies is typically accomplished using a combination of at least two different anti-CD2 antibodies. Stimulatory combinations of anti-CD2 antibodies that have been described include the following: the T11.3 antibody in combination with the T11.1 or T11.2 antibody (Meuer et al., *Cell* 36:897-906, 1984), and the 9.6 antibody (which recognizes the same epitope as T11.1) in combination with the 9-1 antibody (Yang et al., *J. Immunol.* 137:1097-1100, 1986). Other antibodies that bind to the same epitopes as any of the above described antibodies can also be used. Additional antibodies, or combinations of antibodies, can be prepared and identified by standard techniques. Stimulation may also be achieved through contact with superantigens (e.g., *Staphylococcus* enterotoxin A (SEA), *Staphylococcus* enterotoxin B (SEB), Toxic Shock Syndrome Toxin 1 (TSST-1)), endotoxin, or through a variety of mitogens, including but not limited to, phytohemagglutinin (PHA), phorbol myristate acetate (PMA) and ionomycin, lipopolysaccharide (LPS), T cell mitogen, and IL-2.

To further activate a population of T cells, a co-stimulatory or accessory molecule on the surface of the T cells, such as CD28, is stimulated with a ligand that binds the accessory molecule. Accordingly, one of ordinary skill in the art will recognize that any agent, including an anti-CD28 antibody or fragment thereof capable of cross-linking the CD28 molecule, or a natural ligand for CD28 can be used to stimulate T cells. Exemplary anti-CD28 antibodies or fragments thereof useful in the context of the present invention include monoclonal antibody 9.3 (IgG2$_a$) (Bristol-Myers Squibb, Princeton, N. J.), monoclonal antibody KOLT-2 (IgG1), 15E8 (IgG1), 248.23.2 (IgM), clone B-T3 (XR-CD28; Diaclone, Besançon, France) and EX5.3D10 (IgG2$_a$) (ATCC HB11373). Exemplary natural ligands include the B7 family of proteins, such as B7-1 (CD80) and B7-2 (CD86) (Freedman et al., *J. Immunol.* 137:3260-3267, 1987; Freeman et al., *J. Immunol.* 143:2714-2722, 1989; Freeman et al., *J. Exp. Med.* 174:625-631, 1991; Freeman et al., *Science* 262:909-911, 1993; Azuma et al., *Nature* 366:76-79, 1993; Freeman et al., *J. Exp. Med.* 178:2185-2192, 1993).

Other illustrative accessory molecules on the surface of the T cells that can be stimulated with a ligand that binds the accessory molecule in the present invention include, but are not limited to, NKG2D, CD54, LFA-1, ICOS, and CD40.

In addition, binding homologues of a natural ligand, whether native or synthesized by chemical or recombinant techniques, can also be used in accordance with the present invention. Other agents may include natural and synthetic ligands. Agents may include, but are not limited to, other antibodies or fragments thereof, growth factor, cytokine, chemokine, soluble receptor, steroid, hormone, mitogen, such as PHA, or other superantigens.

As described earlier, the subsequent stimulation and activation of the remaining cells that have not undergone apoptosis or have not been sensitized to undergo apoptosis, restores polyclonality to said remaining population of T cells with respect to expressed TCR genes as indicated by spectratype analysis.

Expansion of Cell Populations

Generally, the present invention provides for expansion of the population of cells that remains following exposure of the population to a pro-apoptotic compositions or a sensitizing composition and any subsequent induction of apoptosis in undesired subpopulations of cells, preferably autoreactive or undesired alloreactive T cells. In one embodiment of the invention, the remaining T cells may be stimulated by a single agent. In another embodiment, remaining T cells are stimulated with two or more agents, one that induces a primary signal and additional agents that induce one or more co-stimulatory signals. Ligands useful for stimulating a single signal or stimulating a primary signal and an accessory molecule that stimulates a second signal may be used in soluble form, attached to the surface of a cell, or immobilized on a surface as described herein. A ligand or agent that is attached to a surface serves as a "surrogate" antigen presenting cell (APC). In a preferred embodiment both primary and secondary agents are co-immobilized on a surface. In one embodiment, the molecule providing the primary activation signal, such as a CD3 ligand, and the co-stimulatory molecule, such as a CD28 ligand, are coupled to the same surface, for example, a particle. Further, as noted earlier, one, two, or more stimulatory molecules may be used on the same or differing surfaces.

The cell population may be stimulated as described herein, such as by contact with an anti-CD3 antibody or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of CD4$^+$ cells can be contacted with an anti-CD3 antibody and an anti-CD28 antibody, under conditions appropriate for stimulating proliferation of the T cells. Alternatively, a population of cells can be contacted with PMA and ionomycin. Similarly, to stimulate proliferation of CD8' T cells, an anti-CD3 antibody and the anti-CD28 antibody B-T3, XR-CD28

(Diaclone, Besançon, France) can be used as can other methods commonly known in the art (Berg et al., *Transplant Proc.* 30(8):3975-3977, 1998; Haanen et al., *J. Exp. Med.* 190(9): 1319-1328, 1999; Garland et al., *J. Immunol. Meth.* 227(1-2):53-63, 1999).

The primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc or Sc receptors or an antibody or other binding agent which will bind to the agents. In a preferred embodiment, the two agents are immobilized on a spherical or semispherical surface, the prototypic examples being beads or cells, either on the same bead, i.e., "cis," or to separate beads, i.e., "trans." By way of example, the agent providing the primary activation signal is an anti-CD3 antibody and the agent providing the co-stimulatory signal is an anti-CD28 antibody; and both agents are co-immobilized to the same bead in equivalent molecular amounts. In one embodiment, a 1:1 ratio of each antibody bound to the beads for T cell expansion and T cell growth is used. In certain aspects of the present invention, a ratio of anti CD3:anti-CD28 antibodies (CD3:CD28) bound to the beads is used such that an increase in T cell expansion is observed as compared to the expansion observed using a ratio of 1:1. In one particular embodiment an increase of from about 0.5 to about 3 fold is observed as compared to the expansion observed using a ratio of 1:1. In one embodiment, the ratio of anti-CD3:anti-CD28 (CD3:CD28) antibody bound to the beads ranges from about 100:1 to 1:100 and all integer values there between. In certain embodiments, the ratio of CD3:CD28 is at least about 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 9:1, 8:1, 7:1, 6:1, 5:1, 4:1, 3:1, 2:1, or 1:1. In one aspect of the present invention, more anti-CD28 antibody is bound to the particles than anti-CD3 antibody, i.e., the ratio of CD3:CD28 is less than one. In certain embodiments of the invention, the ratio of anti-CD28 antibody to anti CD3 antibody bound to the beads is greater than 2:1. In one particular embodiment, a 1:200 CD3:CD28 ratio of antibody bound to beads is used. In one particular embodiment, a 1:150 CD3:CD28 ratio of antibody bound to beads is used. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:45 CD3:CD28 ratio of antibody bound to beads is used. In another embodiment, a 1:40 CD3:CD28 ratio of antibody bound to beads is used. In another embodiment, a 1:35 CD3:CD28 ratio of antibody bound to beads is used. In another embodiment, a 1:30 CD3:CD28 ratio of antibody bound to beads is used. In another embodiment, a 1:25 CD3:CD28 ratio of antibody bound to beads is used. In another embodiment, a 1:20 CD3:CD28 ratio of antibody bound to beads is used. In another embodiment, a 1:15 CD3:CD28 ratio of antibody bound to beads is used. In one preferred embodiment, a 1:10 CD3:CD28 ratio of antibody bound to beads is used. In another embodiment, a 1:5 CD3:CD28 ratio of antibody bound to beads is used. In another embodiment, a 1:4 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particle to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:50 to 50:1 and any integer values in between. In another embodiment, the ratio of cells to particles ranges from 1:9 to 9:1 and any integer values in between, can also be used to stimulate T cells. The ratio of anti-CD3- and anti-CD28-coupled particles to T cells that result in T cell stimulation can vary as noted above, however certain preferred values include at least 1:150, 1:125, 1:100, 1:75, 1:50, 1:40, 1:30, 1:20, 1:10, 1:9, 1:8, 1:7, 1:6, 1:5, 1:4, 1:3, 1:2.5, 1:2, 1:1, 2:1, 3:1, 4:1, 5:1, 6:1, 7:1, 8:1, 9:1, 10:1, and 15:1, with one preferred ratio being at least 1:1 particles per T cell. In one particular embodiment, the preferred ratio of particles to cells is 1:5 or 1:10. In one embodiment, a ratio of particles to cells of 1:1 or less is used.

In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In another embodiment, the ratio of particles to cells is at least about 1:2.5 on the first day and additional particles are added to the cells on day 5 at about 1:10, 1:25, 1:50 or 1:100, on day 7 at 1:10, 1:25, 1:50, or 1:100 and on day 9 at 1:10, 1:25, 1:50, or 1:100. In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

One aspect of the present invention stems from the surprising finding that using different bead:cell ratios can lead to different outcomes with respect to expansion of antigen-specific T cells. In particular, bead:cell ratios can be varied to selectively expand or delete antigen-specific (memory) T cells. In one embodiment, the particular bead:cell ratio used selectively deletes antigen-specific T cells. Specifically, high bead:cell ratios, such as about 5:1, 10:1, 15:1, 20:1, 25:1, 30:1, 35:1, 40:1, 45:1, 50:1, and higher, induce deletion of antigen-specific T cells. Without being bound by theory, it is thought that the antigen-specific T cells are sensitized to further stimulation. Thus, the key appears to be the strength of the T cell activation signal: selective expansion of memory T cells (antigen-specific T cells) occurs with "weak" signals while selective deletion of memory T cells occurs with "strong" signals. The quantity of the CD3/TCR (and CD28) receptors that bound by ligands determines the signal strength. Thus, stimulation with high bead:cell ratios provides a high concentration of stimulating antibody (i.e., "strong" signal), leading to over-stimulation of antigen-specific T cells, causing them to die, either by apoptosis or other mechanisms. Thus, in this regard, the bead compositions described herein are functioning as a pro-apoptotic composition. Further, in this regard, as the skilled artisan would appreciate, in certain embodiments, the same composition used as a pro-apoptotic composition (e.g., a surface having attached thereto an agent that stimulates a cell surface moiety, such as the bead compositions described herein) is used to expand the remaining mixed population of cells for use in any variety of immunotherapeutic settings as described herein. Using lower bead:cell ratios provides a stimulation signal to antigen-specific T cells that does not over-stimulate, but rather induces rapid proliferation of these cells. In a further embodiment, the particular bead:cell ratio used selectively expands antigen-specific T cells. The skilled artisan would readily appreciate that any ratio can be used as long as the desired expansion or deletion occurs. Therefore, the compositions and methods described herein can be used to expand specific populations of T cells, or to delete specific populations of T cells, for use in any variety of immunotherapeutic settings described herein.

Using certain methodologies it may be advantageous to maintain long-term stimulation of a population of T cells following the initial activation and stimulation, by separating the T cells from the stimulus after a period of about 7 to about 14 days. The rate of T cell proliferation is monitored periodically (e.g., daily) by, for example, examining the size or measuring the volume of the T cells, such as with a Coulter Counter. In this regard, a resting T cell has a mean diameter of about 6.8 microns, and upon initial activation and stimulation, in the presence of the stimulating ligand, the T cell mean diameter will increase to over 12 microns by day 4 and begin to decrease by about day 6. When the mean T cell diameter decreases to approximately 8 microns, the T cells may be reactivated and re-stimulated to induce further proliferation of the T cells. Alternatively, the rate of T cell proliferation and time for T cell re-stimulation can be monitored by assaying for the presence of cell surface molecules, such as, CD154, CD54, CD25, CD137, CD134, which are induced on activated T cells.

For inducing long-term stimulation of a population of $CD4^+$ and/or $CD8^+$ T cells, it may be necessary to reactivate and re-stimulate the T cells with a stimulatory agent such as an anti-CD3 antibody and an anti-CD28 antibody (e.g., B-T3, XR-CD28 (Diaclone, Besançon, France)) several times to produce a population of $CD4^+$ or $CD8^+$ cells increased in number from about 10 to about 1.000-fold the original T cell population. For example, in one embodiment of the present invention, T cells are stimulated as described for 2-3 times. In further embodiments, T cells are stimulated as described for 4 or 5 times. Using the present methodology, it is possible to achieve T cell numbers from about 100 to about 100,000-fold that have increased polyclonality as compared to prior to stimulation. Moreover, T cells expanded by the method of the present invention secrete substantial levels of cytokines (e.g., IL-2, IFN-γ, IL-4, GM-CSF and TNF-α) into the culture supernatants. For example, as compared to stimulation with IL-2, $CD4^+$ T cells expanded by use of anti-CD3 and anti-CD28 co-stimulation secrete high levels of GM-CSF and TNF-α into the culture medium. These cytokines can be purified from the culture supernatants or the supernatants can be used directly for maintaining cells in culture. Similarly, the T cells expanded by the method of the present invention together with the culture supernatant and cytokines can be administered to support the growth of cells in vivo.

In one embodiment, T cell stimulation is performed, for example with anti-CD3 and anti-CD28 antibodies co-immobilized on beads (3×28 beads), for a period of time sufficient for the cells to return to a quiescent state (low or no proliferation) (approximately 8-14 days after initial stimulation). The stimulation signal is then removed from the cells and the cells are washed and infused back into the patient. The cells at the end of the stimulation phase are rendered "super-inducible" by the methods of the present invention, as demonstrated by their ability to respond to antigens and the ability of these cells to demonstrate a memory-like phenotype, as is evidence by the examples. Accordingly, upon re-stimulation either exogenously or by an antigen in vivo after infusion, the activated T cells demonstrate a robust response characterized by unique phenotypic properties, such as sustained CD154 expression, increased cytokine production, etc.

In further embodiments of the present invention, the cells, such as T cells are combined with agent-coated or conjugated beads, the beads and the cells are subsequently separated, and then the cells are cultured. In an alternative embodiment, prior to culture, the agent-coated or conjugated beads and cells are not separated but are cultured together. In a further embodiment, the beads and cells are first concentrated by application of a force, resulting in cell surface moiety ligation, thereby inducing cell stimulation and/or polarization of the activation signal.

By way of example, when T cells are the target cell population, the cell surface moieties may be ligated by allowing paramagnetic beads to which anti-CD3 and anti-CD28 antibodies are attached (3×28 beads) to contact the T cells prepared. In one embodiment the cells (for example, 104 to 109 T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and particles, interactions between particles and cells is minimized. This selects for cells that express high amounts of desired antigens to be bound to the particles. For example, CD4+ T cells express higher levels of CD28 and are more efficiently captured and stimulated than CD8+ T cells in dilute concentrations. In one embodiment, the concentration of cells used is about $5 \times 10^6$/ml. In other embodiments, the concentration used can be from about $1 \times 10^5$/ml to about $1 \times 10^6$/ml, and any integer value in between.

The buffer that the cells are suspended in may be any that is appropriate for the particular cell type. When utilizing certain cell types the buffer may contain other components, e.g., 1-5% serum, necessary to maintain cell integrity during the process. In another embodiment, the cells and beads may be combined in cell culture media. The cells and beads may be mixed, for example, by rotation, agitation or any means for mixing, for a period of time ranging from one minute to several hours. The container of beads and cells is then concentrated by a force, such as placing in a magnetic field. Media and unbound cells are removed and the cells attached to the beads or other surface are washed, for example, by pumping via a peristaltic pump, and then resuspended in media appropriate for cell culture.

In one embodiment of the present invention, the mixture may be cultured for 30 minutes to several hours (about 3 hours) to about 14 days or any hourly or minute integer value in between. In another embodiment, the mixture may be cultured for 21 days. In one embodiment of the invention the beads and the T cells are cultured together for about eight days. In another embodiment, the beads and T cells are cultured together for 2-3 days. As described above, several cycles of stimulation may also be desired such that culture time of T cells can be 60 days or more. Conditions appropriate for T cell culture include an appropriate media (e.g., Minimal Essential Media or RPMI Media 1640 or, X-vivo 15, (BioWhittaker)) that may contain factors necessary for proliferation and viability, including serum (e.g., fetal bovine or human serum) or interleukin-2 (IL-2). insulin, or any other additives for the growth of cells known to the skilled artisan. Media can include RPMI 1640, AIM-V, DMEM, MEM, $\alpha$-MEM, F-12, X-Vivo 15, and X-Vivo 20, with added amino acids and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

In one embodiment of the present invention, bead:cell ratios can be tailored to obtain a desired T cell phenotype. In one particular embodiment, bead:cell ratios can be varied to selectively expand or delete antigen-specific (memory) T cells. In one embodiment, the particular bead:cell ratio used selectively deletes antigen-specific T cells. In a further embodiment, the particular bead:cell ratio used selectively expands antigen-specific T cells. The skilled artisan would readily appreciate that any ratio can be used as long as the desired expansion or deletion of antigen-specific T cells occurs. Therefore, the compositions and methods described herein can be used to expand specific populations of T cells, or to delete specific populations of T cells, for use in any variety of immunotherapeutic settings described herein.

In another embodiment, the time of exposure to stimulatory agents such as anti-CD3/anti-CD28 (i.e., 3×28)-coated beads may be modified or tailored in such a way to obtain a desired T cell phenotype. Alternatively, a desired population of T cells can be selected using any number of selection techniques, prior to stimulation. One may desire a greater population of helper T cells ($T_H$), typically CD4+ as opposed to CD8+ cytotoxic or regulatory T cells, because an expansion of $T_H$ cells could improve or restore overall immune responsiveness. While many specific immune responses are mediated by CD8+ antigen-specific T cells, which can directly lyse or kill target cells, most immune responses require the help of CD4+ T cells, which express important immune-regulatory molecules, such as GM-CSF, CD40L, and IL-2, for example. Where CD4-mediated help is preferred, a method, such as that described herein, which preserves or enhances the CD4:CD8 ratio could be of significant benefit. Increased numbers of CD4+ T cells can increase the amount of cell-expressed CD40L introduced into patients, potentially improving target cell visibility (improved APC function). Similar effects can be seen by increasing the number of infused cells expressing GM-CSF, or IL-2, all of which are expressed predominantly by CD4+ T cells. Likewise, it may be desirable in certain applications to utilize a population of regulatory T cells (e.g., Autoimmun Rev. 2002 August; 1(4):190-7; Curr Opin Immunol. 2002 December; 14(6):771-8) which can be generated and expanded using the methods described herein. Alternatively, in situations where CD4-help is needed less and increased numbers of CD8+ T cells are desirous, the XCELLERATE™ approaches described herein can also be utilized, by for example, pre-selecting for CD8+ cells prior to stimulation and/or culture. Such situations may exist where increased levels of IFN-γ or increased cytolysis of a target cell is preferred. One may also modify time and type of exposure to stimulatory agents to expand T cells with a desired TCR repertoire, e.g., expressing desired Vβ family genes.

To effectuate isolation of different T cell populations, exposure times to the particles may be varied. For example, in one preferred embodiment, T cells are isolated by incubation with 3×28 beads, such as DYNABEADS® M-450, for a time period sufficient for positive selection of the desired T cells. In one embodiment, the time period is about 30 minutes. In a further embodiment, the time period is at least 1, 2, 3, 4, 5, or 6 hours. In yet another preferred embodiment, the time period is 10 to 24 hours or more. In one preferred embodiment, the incubation time period is 24 hours. For isolation of T cells from cancer patients, use of longer incubation times, such as 24 hours, can increase cell yield.

In certain embodiments, stimulation and/or expansion times may be 10 weeks or less, 8 weeks or less, four weeks or less, 2 weeks or less, 10 days or less, or 8 days or less (four weeks or less includes all time ranges from 4 weeks down to 1 day (24 hours) or any value between these numbers). In some embodiments in may be desirable to clone T cells using, for example, limiting dilution or cell sorting, wherein longer stimulation time may be necessary. In some embodiments, stimulation and expansion may be carried out for 6 days or less, 4 days or less, 2 days or less, and in other embodiments for as little as 24 or less hours, and preferably 4-6 hours or less (these ranges include any integer values in between). When stimulation of T cells is carried out for shorter periods of time, the population of T cells may not increase in number as dramatically, but the population will provide more robust and healthy activated T cells that can continue to proliferate in vivo and more closely resemble the natural effector T cell pool. As the availability of T cell help is often the limiting factor in antibody responses to protein antigens, the ability to selectively expand or selectively infuse a CD4+ rich population of T cells into a subject is extremely beneficial. Further benefits of such enriched populations are readily apparent in that activated helper T cells that recognize antigens presented by B lymphocytes deliver two types of stimuli, physical contact and cytokine production, that result in the proliferation and differentiation of B cells.

In the various embodiments, one of ordinary skill in the art understands removal of the stimulation signal from the cells is dependent upon the type of surface used. For example, if paramagnetic beads are used, then magnetic separation is the feasible option. Separation techniques are described in detail by paramagnetic bead manufacturers' instructions (for example, DYNAL Inc., Oslo, Norway). Furthermore, filtration may be used if the surface is a bead large enough to be separated from the cells. In addition, a variety of transfusion filters are commercially available, including 20 micron and 80 micron transfusion filters (Baxter). Accordingly, so long as the beads are larger than the mesh size of the filter, such filtration is highly efficient. In a related embodiment, the beads may pass through the filter, but cells may remain, thus allowing separation. In one particular embodiment, the biocompatible surface used degrades (i.e., is biodegradable) in culture during the exposure period.

Although the antibodies used in the methods described herein can be readily obtained from public sources, such as the American Type Culture Collection (ATCC), antibodies to T cell accessory molecules and the CD3 complex can be produced by standard techniques. Methodologies for generating antibodies for use in the methods of the invention are well-known in the art and are discussed in further detail herein.

Ligand Immobilization on a Surface

As indicated above, the methods of the present invention preferably use ligands bound to a surface. The surface may be any surface capable of having a ligand bound thereto or integrated into and that is biocompatible, that is, substantially non-toxic to the target cells to be stimulated. The biocompatible surface may be biodegradable or non-biodegradable. The surface may be natural or synthetic, and a synthetic surface may be a polymer. The surface may comprise collagen, purified proteins, purified peptides, polysaccharides, glycosaminoglycans, extracellular matrix compositions, liposomes, or cell surfaces. A polysaccharide may include for example, cellulose, agarose, dextran, chitosan, hyaluronic acid, or alginate. Other polymers may include polyesters, polyethers, polyanhydrides, polyalkylcyanoacryllates, polyacrylamides, polyorthoesters, polyphosphazenes, polyvinylacetates, block copolymers, polypropylene, polytetrafluoroethylene (PTFE), or polyurethanes. The polymer may be lactic acid or a copolymer. A copolymer may comprise lactic acid and glycolic acid (PLGA). Non-biodegradable surfaces may include polymers, such as poly(dimethylsiloxane) and poly(ethylene-vinyl acetate). Biocompatible surfaces include for example, glass (e.g., bioglass), collagen, chitin, metal, hydroxyapatite, aluminate, bioceramic materials, hyaluronic acid polymers, alginate, acrylic ester polymers, lactic acid polymer, glycolic acid polymer, lactic acid/glycolic acid polymer, purified proteins, purified peptides, or extracellular matrix compositions. Other polymers comprising a surface may include glass, silica, silicon, hydroxyapatite, hydrogels, collagen, acrolein, polyacrylamide, polypropylene, polystyrene, nylon, or any number of plastics or synthetic organic polymers, or the like. The surface may comprise a biological structure, such as a liposome or cell surface, such as red blood cells (RBCs). The surface may be in the form of a lipid, a plate, bag, pellet, fiber, mesh, or particle. A particle may include, a colloidal particle, a microsphere, nanoparticle, a bead, or the like. In the various embodiments, commercially available surfaces, such as beads or other particles, are useful (e.g., Miltenyi Particles, Miltenyi Biotec, Germany; Sepharose beads, Pharmacia Fine Chemicals, Sweden; DYNABEADS™, Dynal Inc., New York; PURABEADS™, Prometic Biosciences).

When beads are used, the bead may be of any size that effectuates target cell stimulation. In one embodiment, beads are preferably from about 5 nanometers to about 500 μm in size. Accordingly, the choice of bead size depends on the particular use the bead will serve. For example, if the bead is used for monocyte depletion, a small size is chosen to facilitate monocyte ingestion (e.g., 1.0 μm and 4.5 μm in diameter or any size that may be engulfed, such as nanometer sizes); however, when separation of beads by filtration is desired, bead sizes of no less than 50 μm are typically used. Further, when using paramagnetic beads, the beads typically range in size from about 2.8 μm to about 500 μm and more preferably from about 2.8 μm to about 50 μm. Lastly, one may choose to use super-paramagnetic nanoparticles which can be as small as about $10^{-5}$ nm. Accordingly, as is readily apparent from the discussion above, virtually any particle size may be utilized.

An agent may be attached, incorporated into, coupled to, or integrated into a surface by a variety of methods known and available in the art. The agent may be a natural ligand, a protein ligand, or a synthetic ligand. The attachment may be covalent or noncovalent, electrostatic, or hydrophobic and may be accomplished by a variety of attachment means, including for example, chemical, mechanical, enzymatic, electrostatic, or other means whereby a ligand is capable of stimulating the cells. The attachment of the agent may be direct or indirect (e.g., tethered). For example, the antibody to a ligand first may be attached to a surface (direct attachment), or avidin or streptavidin, or a second antibody that binds the first, may be attached to the surface for binding to a biotinylated ligand (indirect attachment). With respect to cell surfaces, the attachment may be via genetic expression of the agent using any number of technologies known in the art, such as transfection or transduction, etc of an expression vector comprising the coding region of the agent of interest. The antibody to the ligand may be attached to the surface via an anti-idiotype antibody. Another example includes using protein A or protein G, or other non-specific antibody binding molecules, attached to surfaces to bind an antibody. Alternatively, the ligand may be attached to the surface by chemical means, such as cross-linking to the surface, using commercially available cross-linking reagents (Pierce, Rockford, Ill.) or other means. In certain embodiments, the ligands are covalently bound to the surface. Further, in one embodiment, commercially available tosyl-activated DYNABEADS™ or DYNABEADS™ with epoxy-surface reactive groups are incubated with the polypeptide ligand of interest according to the manufacturer's instructions. Briefly, such conditions typically involve incubation in a phosphate buffer from pH 4 to pH 9.5 at temperatures ranging from 4 to 37 degrees C.

In one aspect, the agent, such as certain ligands may be of singular origin or multiple origins and may be antibodies or fragments thereof while in another aspect, when utilizing T cells, the co-stimulatory ligand is a B7 molecule (e.g., B7-1, B7-2). These ligands are coupled to the surface by any of the different attachment means discussed above. The B7 molecule to be coupled to the surface may be isolated from a cell expressing the co-stimulatory molecule, or obtained using standard recombinant DNA technology and expression systems that allow for production and isolation of the co-stimulatory molecule(s) as described herein. Fragments, mutants, or variants of a B7 molecule that retain the capability to trigger a co-stimulatory signal in T cells when coupled to the surface of a cell can also be used. Furthermore, one of ordinary skill in the art will recognize that any ligand useful in the activation and induction of proliferation of a subset of T cells may also be immobilized on beads or culture vessel surfaces or any surface. In addition, while covalent binding of the ligand to the surface is one preferred methodology, adsorption or capture by a secondary monoclonal antibody may also be used. The amount of a particular ligand attached to a surface may be readily determined by flow cytometric analysis if the surface is that of beads or determined by enzyme-linked immunosorbant assay (ELISA) if the surface is a tissue culture dish, mesh, fibers, bags, for example.

In a particular embodiment, the stimulatory form of a B7 molecule or an anti-CD28 antibody or fragment thereof is attached to the same solid phase surface as the agent that stimulates the TCR/CD3 complex, such as an anti-CD3 antibody. In addition to anti-CD3 antibodies, other antibodies that bind to receptors that mimic antigen signals may be used. For example, the beads or other surfaces may be coated with combinations of anti-CD2 antibodies and a B7 molecule and in particular anti-CD3 antibodies and anti-CD28 antibodies.

When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In a preferred embodiment, the two agents are immobilized on beads, either on the same bead, i.e., "cis," or to separate beads, i.e., "trans." By way of example, the agent providing the primary activation signal is an anti-CD3 antibody and the agent providing the co-stimulatory signal is an anti-CD28 antibody; and both agents are co-immobilized to the same bead in equivalent molecular amounts. In one embodiment, a 1:1 ratio of each antibody bound to the beads for CD4+ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 0.5 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:200 CD3:CD28 ratio of antibody bound to beads is used. In one particular embodiment, a 1:150 CD3:CD28 ratio of antibody bound to beads is used. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:45 CD3:CD28 ratio of antibody bound to beads is used. In another embodiment, a 1:40 CD3:CD28 ratio of antibody bound to beads is used. In another embodiment, a 1:35 CD3:CD28 ratio of antibody bound to beads is used. In another embodiment, a 1:30 CD3:CD28 ratio of antibody bound to beads is used. In another embodiment, a 1:25 CD3:CD28 ratio of antibody bound to beads is used. In another embodiment, a 1:20 CD3:CD28 ratio of antibody bound to beads is used. In another embodiment, a 1:15 CD3:CD28 ratio of antibody bound to beads is used. In one preferred embodiment, a 1:10 CD3:CD28 ratio of antibody bound to beads is used. In another embodiment, a 1:5 CD3:CD28 ratio of antibody bound to beads is used. In another embodiment, a 1:4 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Surface-Associated Agents

Agents contemplated by the present invention include protein ligands, natural ligands, and synthetic ligands. Agents that can bind to cell surface moieties, and under certain conditions, cause ligation and aggregation that leads to signaling include, but are not limited to, lectins (for example, phyotohaemagluttinin (PHA), lentil lectins, concanavalin A), antibodies, antibody fragments, peptides, polypeptides, glycopeptides, receptors, B cell receptor and T cell receptor ligands, MHC-peptide dimers or tetramers, extracellular matrix components, steroids, hormones (for example, growth hormone, corticosteroids, prostaglandins, tetra-iodo thyronine), bacterial moieties (such as lipopolysaccharides), mitogens, superantigens and their derivatives, growth factors, cytokines, adhesion molecules (such as, L-selectin, LFA-3, CD54, LFA-1), chemokines, and small molecules. The agents may be isolated from natural sources such as cells, blood products, and tissues, or isolated from cells propagated in vitro, prepared recombinantly, by chemical synthesis, or by other methods known to those with skill in the art.

In one aspect of the present invention, when it is desirous to stimulate T cells, useful agents include ligands that are capable of binding the CD3/TCR complex, CD2, and/or CD28 and initiating activation or proliferation, respectively. Accordingly, the term ligand includes those proteins that are the "natural" ligand for the cell surface protein, such as a B7 molecule for CD28, as well as artificial ligands such as antibodies directed to the cell surface protein. Such antibodies and fragments thereof may be produced in accordance with conventional techniques, such as hybridoma methods and recombinant DNA and protein expression techniques. Useful antibodies and fragments may be derived from any species, including humans, or may be formed as chimeric proteins, which employ sequences from more than one species.

Methods well known in the art may be used to generate antibodies, polyclonal antisera, or monoclonal antibodies that are specific for a ligand. Antibodies also may be produced as genetically engineered immunoglobulins (Ig) or Ig fragments designed to have desirable properties. For example, by way of illustration and not limitation, antibodies may include a recombinant IgG that is a chimeric fusion protein having at least one variable (V) region domain from a first mammalian species and at least one constant region domain from a second distinct mammalian species. Most commonly, a chimeric antibody has murine variable region sequences and human constant region sequences. Such a murine/human chimeric immunoglobulin may be "humanized" by grafting the complementarity determining regions (CDRs), which confer binding specificity for an antigen, derived from a murine antibody into human-derived V region framework regions and human-derived constant regions. Antibodies containing CDRs of different specificities can also be combined to generate multi-specific (bi or tri-specific, etc.) antibodies. Fragments of these molecules may be generated by proteolytic digestion, or optionally, by proteolytic digestion followed by mild reduction of disulfide bonds and alkylation, or by recombinant genetic engineering techniques.

Antibodies are defined to be "immunospecific" if they specifically bind the antigen with an affinity constant, $K_a$, of greater than or equal to about $10^4$ $M^{-1}$, preferably of greater than or equal to about $10^5$ $M^{-1}$, more preferably of greater than or equal to about $10^6$ $M^{-1}$, and still more preferably of greater than or equal to about $10^7$ $M^{-1}$. Affinities of binding partners or antibodies can be readily determined using conventional techniques, for example, those described by Scatchard et al. (*Ann. N.Y. Acad. Sci. USA* 51:660, 1949) or by surface plasmon resonance (BIAcore, Biosensor, Piscataway, N.J.) See, e.g., Wolff et al., *Cancer Res.*, 53:2560-2565, 1993).

Antibodies may generally be prepared by any of a variety of techniques known to those having ordinary skill in the art (See, e.g., Harlow et al., *Antibodies: A Laboratory Manual*, 1988, Cold Spring Harbor Laboratory). In one such technique, an animal is immunized with the ligand as antigen to generate polyclonal antisera. Suitable animals include rabbits, sheep, goats, pigs, cattle, and may include smaller mammalian species, such as, mice, rats, and hamsters. Antibodies of the present invention may also be generated as described in U.S. Pat. Nos. 6,150,584, 6,130,364, 6,114,598, 5,833,985, 6,071,517, 5,756,096, 5,736,137, and 5,837,243.

An immunogen may be comprised of cells expressing the ligand, purified or partially purified ligand polypeptides or variants or fragments thereof, or ligand peptides. Ligand peptides may be generated by proteolytic cleavage or may be chemically synthesized. Peptides for immunization may be selected by analyzing the primary, secondary, or tertiary structure of the ligand according to methods know to those skilled in the art in order to determine amino acid sequences more likely to generate an antigenic response in a host animal (See, e.g., Novotny, *Mol. Immunol.* 28:201-207, 1991; Berzoksky, *Science* 229:932-40, 1985).

Preparation of the immunogen may include covalent coupling of the ligand polypeptide or variant or fragment thereof, or peptide to another immunogenic protein, such as, keyhole limpet hemocyanin or bovine serum albumin. In addition, the peptide, polypeptide, or cells may be emulsified in an adjuvant (See Harlow et al., *Antibodies: A Laboratory Manual*, 1988 Cold Spring Harbor Laboratory). In general, after the first injection, animals receive one or more booster immunizations according to a preferable schedule for the animal species. The immune response may be monitored by periodically bleeding the animal, separating the sera, and analyzing the sera in an immunoassay, such as an Ouchterlony assay, to assess the specific antibody titer. Once an antibody titer is established, the animals may be bled periodically to accumulate the polyclonal antisera. Polyclonal antibodies that bind specifically to the ligand polypeptide or peptide may then be purified from such antisera, for example, by affinity chromatography using protein A or using the ligand polypeptide or peptide coupled to a suitable solid support.

Monoclonal antibodies that specifically bind ligand polypeptides or fragments or variants thereof may be prepared, for example, using the technique of Kohler and Milstein (*Nature*, 256:495-497, 1975; *Eur. J. Immunol.* 6:511-519, 1976) and improvements thereto. Hybridomas, which are immortal eukaryotic cell lines, may be generated that produce antibodies having the desired specificity to a ligand polypeptide or variant or fragment thereof. An animal—for example, a rat, hamster, or preferably mouse—is immunized with the ligand immunogen prepared as described above. Lymphoid cells, most commonly, spleen cells, obtained from an immunized animal may be immortalized by fusion with a drug-sensitized myeloma cell fusion partner, preferably one that is syngeneic with the immunized animal. The spleen cells and myeloma cells may be combined for a few minutes with a membrane fusion-promoting agent, such as polyethylene glycol or a nonionic detergent, and then plated at low density on a selective medium that supports the growth of hybridoma cells, but not myeloma cells. A preferred selection media is HAT (hypoxanthine, aminopterin, thymidine). After a sufficient time, usually about 1 to 2 weeks, colonies of cells are observed. Single colonies are isolated, and antibodies produced by the cells may be tested for binding activity to the ligand polypeptide or variant or fragment thereof. Hybridomas producing antibody with high affinity and specificity for the ligand antigen are preferred. Hybridomas that produce monoclonal antibodies that specifically bind to a ligand polypeptide or variant or fragment thereof are contemplated by the present invention.

Monoclonal antibodies may be isolated from the supernatants of hybridoma cultures. An alternative method for production of a murine monoclonal antibody is to inject the hybridoma cells into the peritoneal cavity of a syngeneic mouse. The mouse produces ascites fluid containing the monoclonal antibody. Contaminants may be removed from the antibody by conventional techniques, such as chromatography, gel filtration, precipitation, or extraction.

Human monoclonal antibodies may be generated by any number of techniques. Methods include but are not limited to, Epstein Barr Virus (EBV) transformation of human peripheral blood cells (see, U.S. Pat. No. 4,464,456), in vitro immunization of human B cells (see, e.g., Boerner et al., *J. Immunol.* 147:86-95, 1991), fusion of spleen cells from immunized transgenic mice carrying human immunoglobulin genes and fusion of spleen cells from immunized transgenic mice carrying immunoglobulin genes inserted by yeast artificial chromosome (YAC) (see, e.g., U.S. Pat. No. 5,877,397; Bruggemann et al., *Curr. Opin. Biotechnol.* 8:455-58, 1997; Jakobovits et al., *Ann. N.Y. Acad. Sci.* 764:525-35, 1995), or isolation from human immunoglobulin V region phage libraries.

Chimeric antibodies and humanized antibodies for use in the present invention may be generated. A chimeric antibody has at least one constant region domain derived from a first mammalian species and at least one variable region domain derived from a second distinct mammalian species (See, e.g., Morrison et al., *Proc. Natl. Acad. Sci. USA,* 81:6851-55, 1984). Most commonly, a chimeric antibody may be constructed by cloning the polynucleotide sequences that encode at least one variable region domain derived from a non-human monoclonal antibody, such as the variable region derived from a murine, rat, or hamster monoclonal antibody, into a vector containing sequences that encode at least one human constant region. (See, e.g., Shin et al., *Methods Enzymol.* 178:459-76, 1989; Walls et al., *Nucleic Acids Res.* 21:2921-29, 1993). The human constant region chosen may depend upon the effector functions desired for the particular antibody. Another method known in the art for generating chimeric antibodies is homologous recombination (U.S. Pat. No. 5,482,856). Preferably, the vectors will be transfected into eukaryotic cells for stable expression of the chimeric antibody.

A non-human/human chimeric antibody may be further genetically engineered to create a "humanized" antibody. Such an antibody has a plurality of CDRs derived from an immunoglobulin of a non-human mammalian species, at least one human variable framework region, and at least one human immunoglobulin constant region. Humanization may yield an antibody that has decreased binding affinity when compared with the non-human monoclonal antibody or the chimeric antibody. Those having skill in the art, therefore, use one or more strategies to design humanized antibodies.

Within certain embodiments, the use of antigen-binding fragments of antibodies may be preferred. Such fragments include Fab fragments or F(ab')$_2$ fragments, which may be prepared by proteolytic digestion with papain or pepsin, respectively. The antigen binding fragments may be separated from the Fc fragments by affinity chromatography, for example, using immobilized protein A or immobilized ligand polypeptide or a variant or a fragment thereof. An alternative method to generate Fab fragments includes mild reduction of F(ab')$_2$ fragments followed by alkylation (See, e.g., Weir, *Handbook of Experimental Immunology*, 1986, Blackwell Scientific, Boston).

Non-human, human, or humanized heavy chain and light chain variable regions of any of the above described Ig molecules may be constructed as single chain Fv (sFv) fragments (single chain antibodies). See, e.g., Bird et al., *Science* 242: 423-426, 1988; Huston et al., *Proc. Natl. Acad. Sci. USA* 85:5879-5883, 1988. Multi-functional fusion proteins may be generated by linking polynucleotide sequences encoding an sFv in-frame with polynucleotide sequences encoding various effector proteins. These methods are known in the art, and are disclosed, for example, in EP-B1-0318554, U.S. Pat. No. 5,132,405,U.S. Pat. No. 5,091,513, and U.S. Pat. No. 5,476,786.

An additional method for selecting antibodies that specifically bind to a ligand polypeptide or variant or fragment thereof is by phage display (See, e.g., Winter et al., *Annul. Rev. Immunol.* 12:433-55, 1994; Burton et al., *Adv. Immunol.* 57:191-280, 1994). Human or murine immunoglobulin variable region gene combinatorial libraries may be created in phage vectors that can be screened to select Ig fragments (Fab, Fv, sFv, or multimers thereof) that bind specifically to a ligand polypeptide or variant or fragment thereof (See, e.g., U.S. Pat. No. 5,223,409; Huse et al., *Science* 246:1275-81, 1989; Kang et al., *Proc. Natl. Acad. Sci. USA* 88:4363-66, 1991; Hoogenboom et al., *J. Molec. Biol.* 227:381-388, 1992; Schlebusch et al., *Hybridoma* 16:47-52, 1997 and references cited therein).

Methods of Use

Monoclonal and oligoclonal T cell populations are associated with most autoimmune diseases and are often correlated with disease activity. Further, broad T cell repertoire is restored when patients achieve disease remission. The present invention relates generally to methods for stimulating T cells, and more particularly, to methods to eliminate undesired (e.g., autoreactive, alloreactive, pathogenic) subpopulations of T cells from a mixed population of T cells, thereby restoring the normal immune repertoire of the T cells. Thus, the present invention provides compositions of cells, including stimulated T cells having restored immune repertoire and uses thereof.

Generally, the compositions and methodologies described herein can be used to eliminate at least a portion of undesired clonal populations of cells, typically T cells, B cells, NKT, or NK cells, from a population of immune cells. The present invention further provides for compositions comprising populations of cells that no longer contain undesired cells, or have a significantly reduced number of undesired cells, and uses thereof. The compositions and methods of the present invention are also used to selectively expand a population of cells that have been deleted for undesired clonal populations for use in the treatment of immune defects associated with hematopoietic stem cell transplantation (including allotransplantation and autotransplantation from sources that include blood, cord blood, and bone marrow), organ transplantation (e.g., acute or chronic GVHD), and autoimmune diseases, including autoimmune disease caused by cancers such as large granular lymphocyte (LGL) leukemia, chronic lymphocytic leukemia (CLL) or by common variable immunodeficiency. As a result, a population of cells, in the case of T cells, that express TCRs that are polyclonal with respect to antigen reactivity, but essentially homogeneous with respect to either CD4$^+$ or CD8$^+$, can be produced that have been cleared of any undesired subpopulations of cells, such as autoreactive cells or alloreactive cells. With respect to B cells, a populations of cells can be produced that has been cleared of any undesired subpopulations of B cells producing autoreactive antibodies. In addition, the method allows for the expansion of the resulting population of T- or B-cells in numbers sufficient to reconstitute an individual's total CD4$^+$ or CD8$^+$ T cell population or B cell population (the population of lymphocytes in an individual is approximately 5×10$^{11}$ cells). The resulting cell population can also be genetically transduced using a variety of techniques known to the skilled artisan and used for immunotherapy.

In one embodiment, the T or B cell compositions of the present invention may be used in the context of hematopoietic stem cell transplantation. The major problem in hematopoietic stem cell transplantation is graft-versus-host disease (GVHD), which is caused by alloreactive T cells present in the infused hematopoietic stem cell preparation. Thus, the present invention may be used to remove alloreative T cells and to expand the remaining T cell population for infusion into the patient. The cell compositions of the present invention can be used alone or in conjunction with other therapies.

In one embodiment, the T or B cell compositions of the present invention may be used in the context of any autoimmune disease. Illustrative autoimmune diseases include, but are not limited to, systemic lupus erythematosus (SLE), multiple sclerosis (MS), rheumatoid arthritis, progressive systemic sclerosis, Sjogren's syndrome, multiple sclerosis, polymyositis, dermatomyositis, uveitis, arthritis, psoriatic arthritis, reactive arthritis, Type I insulin-dependent diabetes, Hashimoto's thyroiditis, Grave's thyroiditis, myasthenia gravis, autoimmune myocarditis, vasculitis, aplastic anemia, autoimmune hemolytic anemia, myelodysplastic syndrome, Evan's syndrome, stiff person syndrome, atopic dermatitis, psoriasis, Behchet's syndrome, Crohn's disease, biliary cirrhosis, inflammatory bowel disease, ulcerative colitis, Goodpasture's syndrome, Wegener's granulomatosis, paroxysmal nocturnal hemaglobinuria, myelodysplastic syndrome, allergic disorders such as hay fever, extrinsic asthma, or insect bite and sting allergies, and food and drug allergies.

Further uses of the T and B cell compositions of the present invention may include the treatment and/or prophylaxis of: inflammatory and hyperproliferative skin diseases and cutaneous manifestations of immunologically mediated illnesses, such as, seborrhoeis dermatitis, angioedemas, erythemas, acne, and Alopecia greata; various eye diseases (autoimmune and otherwise); allergic reactions, such as pollen allergies, reversible obstructive airway disease, which includes condition such as asthma (for example, bronchial asthma, allergic asthma, intrinsic asthma, extrinsic asthma and dust asthma), particularly chronic or inveterate asthma (for example, late asthma and airway hyper-responsiveness), bronchitis, allergic rhinitis, and the like; inflammation of mucous and blood vessels.

As noted above, the T and B cell compositions of the present invention may be used in the treatment of immune defects associated with organ transplantation, e.g., host versus graft disease. Treatment of immune defects associated with any organ transplantation is contemplated herein. For example, the methods and cells of the present invention can be used in the treatment of immune defects associated with kidney, heart, lung, and liver transplantation.

In certain embodiments of the present invention, the cells of the present invention are administered to a patient following treatment with an agent such as chemotherapy, radiation, immunosuppressive agents, such as cyclosporine, azathioprine, methotrexate, mycophenolate, and FK506, antibodies, or other immunoablative agents such as CAMPATH, anti-CD3 antibodies, cyclophosphamide, fludarabine, cyclosporine, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin). (Liu et al., *Cell* 66:807-815, 1991; Henderson et al., *Immun.* 73:316-321, 1991; Bierer et al., *Curr. Opin. Immun.* 5:763-773, 1993; Isoniemi (supra)).

In a further embodiment, the cells are administered to a patient whose immune system has been rendered essentially to a naive state through treatment with one or more agents as described herein, followed by an organ transplant in conjunction with an immunosuppressive regimen. Immunosuppressive regimens useful in this context include but are not limited to, anti-CD3 antibodies, anti-CD25 antibodies, ATG, thymoglobulin, campath, fludarabine, cyclophosphamide, FK506, mycophenolate, cyclosporine, CTLA-4 IG, anti-CD40 antibody, destruxin, radiation therapy, and the like. In this regard, many immunosuppressive regimens have been shown to be effective in animal transplant models (e.g., mouse models) but have not been successful in the clinic. Without being bound by theory, one of the major reasons for this discrepancy is thought to be the presence of antigen-specific memory T cells that cross react with donor alloantigens in the transplanted organ. Lymphoablation in vivo followed by infusion of activated T cells grown under conditions that favor deletion of antigen-specific memory T cells as described herein while preserving naïve T cells may provide conditions similar to the pathogen-free mice that accept organs under a variety of immunosuppressive regimens. This would enable wider and more successful use of immunosuppressive drugs. Additionally, infusion of the T cells as described herein in this setting would lead to a decrease in the use and amount of toxic immunosuppresive drugs, including the number of drugs administered and the length of time that patients are on these drugs. This in turn would lead to increased efficacy (fewer organ rejections) and decreased toxicity. Further, this would also allow the use of organ transplantation in settings such as severe mismatching and could allow successful transplants in xenogeneic settings.

In a further embodiment, the cell compositions of the present invention are administered to a patient with autoimmune disease following T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered to a patient with autoimmune disease following B-cell ablative therapy such as agents that react with CD20, e.g., Rituxan. The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

In a further aspect of the present invention, at least a substantial portion of autoreactive cells from a patient are eliminated in vitro using the methods of the present invention then further stimulated and expanded and administered to the patient. In a related embodiment, at least a substantial portion of autoreactive cells from a patient are eliminated in vitro using the methods of the present invention then administered to the patient and expanded in vivo. It is envisioned as one aspect that the compositions of the present invention can be used in conjunction with other therapies available in the art for treatment of autoimmune disease.

In one embodiment, T cells can be stimulated and expanded as described herein to induce or enhance responsiveness in an individual who is immunocompromised as a result of treatment associated with hematopoietic stem cell transplantation. The present invention provides methods for reducing the risk of, or the severity of, an adverse GVHD effect in a patient who is undergoing a hematopoietic stem cell transplant, comprising administering to the patient a population of T cells of the present invention. In one particular embodiment, at least a substantial portion of alloreactive cells present in the donor hematopoietic stem cells are eliminated by the methods of the present invention. In a further embodiment, the T cell compositions of the present invention are administered to a patient undergoing a hematopoietic stem cell transplantation following treatment with chemotherapy agents. In a further embodiment, at least a substantial portion of alloreactive cells from the donor marrow are eliminated in vitro using the methods of the present invention then further stimulated and expanded and then administered to the patient. In a further embodiment, at least a substantial portion of alloreactive cells from the donor marrow are eliminated in vitro using the methods of the present invention then administered to the patient and expanded in vivo. It is envisioned as one aspect that the compositions of the present invention can be used in conjunction with other therapies available in the art for use in hematopoietic stem cell transplantation, such as administration of G-CSF, IL-2, IL-11, IL-7, IL-12, and anti-viral treatments.

In one embodiment, T cells can be stimulated and expanded as described herein to induce or enhance responsiveness in an individual who is immunocompromised as a result of treatment associated with organ transplantation, including but not limited to, kidney, heart, lung, and liver transplantation. In one particular embodiment, at least a substantial portion of alloreactive cells present in the recipient are eliminated by the methods of the present invention. Thus, the present invention provides methods for reducing the risk of, or the severity of, organ rejection. In a further embodiment, the T cell compositions of the present invention are administered to a patient undergoing an organ transplant following treatment with chemotherapy agents. In a further embodiment, at least a substantial portion of alloreactive cells from the transplant recipient are eliminated in vitro using the methods of the present invention then further stimulated and expanded and then administered to the patient. It is envisioned as one aspect that the compositions of the present invention can be used in conjunction with other therapies available known in the art for use in organ transplantation.

Figure 9:
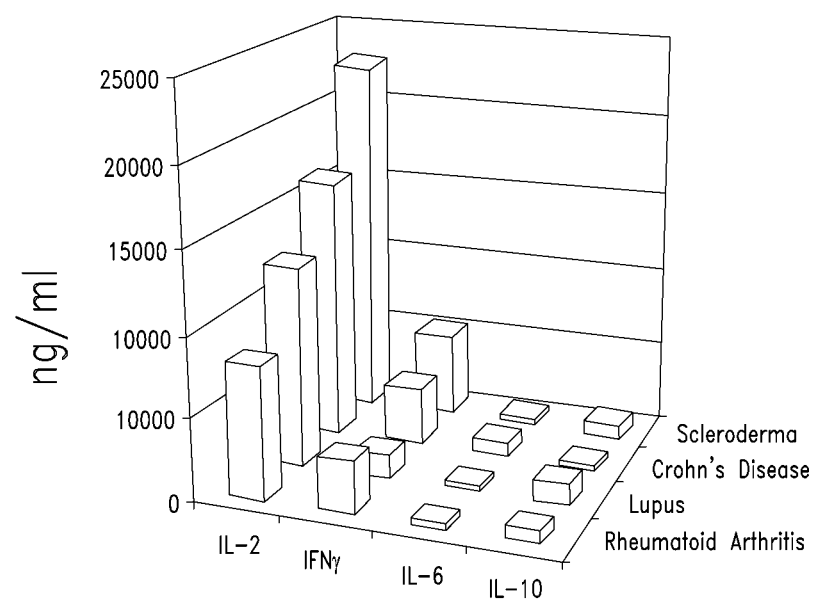
FIG. 9 is a bar graph showing the Th1 phenotype of XCELLERATED™ T cells from patients with scleroderma, Crohn's Disease, lupus, and rheumatoid arthritis.

Another embodiment of the invention, provides a method for selectively expanding a population of $T_{H1}$ cells from a population of CD4$^+$ T cells. In this method, CD4$^+$ T cells are co-stimulated with an anti-CD28 antibody, such as the monoclonal antibody 9.3, inducing secretion of $T_{H1}$-specific cytokines, including IFN-γ, resulting in enrichment of $T_{H1}$ cells over $T_{H2}$ cells. As described further herein, XCELLERATE™ T cells from patients with autoimmune disease demonstrate a $T_{H1}$-type phenotype (see FIG. 9). Accordingly, the XCELLERATE™ process can be used to expand T cells of a desired phenotype, including TH1-type phenotype.

The present invention further provides a method for selectively expanding a population of $T_{H2}$ cells from a population of CD4+ T cells. In this method, CD4+ T cells are co-stimulated with an anti-CD28 antibody, such as the monoclonal antibody B-T3, XR-CD28, inducing secretion of $T_{H2}$-specific cytokines, resulting in enrichment of $T_{H2}$ cells over $T_{H1}$ cells (see for example, Fowler, et al. Blood 1994 Nov. 15; 84(10): 3540-9; Cohen, et al., Ciba Found Symp 1994; 187:179-93).

The present invention further provides methods for using the instant cell compositions in conjunction with regulatory T cells. Without being bound by theory, regulatory T cells may provide help in suppressing aberrant immune responses or otherwise regulating immune cells of the present invention. Regulatory T cells can be generated and expanded using the methods as described herein. The regulatory T cells can be antigen-specific and/or polyclonal. Regulatory T cells can also be generated using art-recognized techniques as described for example, in Woo, et al., J Immunol. 2002 May 1; 168(9):4272-6; Shevach, E. M., Annu. Rev. Immunol. 2000, 18:423; Stephens, et al., Eur. J. Immunol. 2001, 31:1247; Salomon, et al, Immunity 2000, 12:431; and Sakaguchi, et al., Immunol. Rev. 2001, 182:18.

The present invention further provides a method for selectively expanding a population of T cells expressing a specific Vβ, Vα, Vγ, or Vδ gene. For example, in this method, T cells expressing a particular Vβ, Vα, Vγ, or Vδ gene are positively or negatively selected and then further expanded/stimulated according to the methods of the present invention. Alternatively, stimulated and expanded T cells expressing a particular Vβ, Vα, Vγ, or Vδ gene of interest can be positively or negatively selected and further stimulated and expanded.

One aspect of the present invention is to administer activated and expanded T cells that proliferate and grow rapidly in vivo. Without being bound by theory, the infused T cells may suppress in vivo homeostatic T cell proliferation and prevent unwanted T cells from proliferating in vivo, for example cancer cells, autoreactive T cells, alloreactive T cells, HIV infected T cells, and the like (see King, et al., 2004, Cell 117:265-277). Accordingly, the compositions described herein comprising T cells that have been cultured so as to delete at least a substantial portion of unwanted cells can be infused into a patient. In one embodiment, the cells are infused at a dose such that the cells then prevent homeostatic proliferation and therefore, prevent unwanted cells from regenerating in vivo. The frequency of administration of the cells of the present invention will be determined by such factors as the condition of the patient, and the type and severity of the patient's disease, although appropriate dosages may be determined by clinical trials. The precise amount of the compositions comprising cells of the present invention to be administered can be determined by a physician with consideration of individual differences in age, weight, disease severity and condition of the patient and any other factors relevant to treatment of the patient.

In another example, blood is drawn into a stand-alone disposable device directly from the patient that contains a sensitizing composition and or two or more immobilized antibodies (e.g., anti-CD3 and anti-CD28) or other components to stimulate receptors required for T cell activation prior to the cells being administered to the subject (e.g., immobilized on plastic surfaces or upon separable microparticles). In one embodiment, the disposable device may comprise a container (e.g., a plastic bag, or flask) with appropriate tubing connections suitable for combining/docking with syringes and sterile docking devices. This device will contain a solid surface for immobilization of T cell activation components (e.g., anti-CD3 and anti-CD28 antibodies); these may be the surfaces of the container itself or an insert and will typically be a flat surface, an etched flat surface, an irregular surface, a porous pad, fiber, clinically acceptable/safe ferro-fluid, beads, etc.). Additionally when using the stand-alone device, the subject can remain connected to the device, or the device can be separable from the patient. Further, the device may be utilized at room temperature or incubated at physiologic temperature using a portable incubator.

As devices and methods for collecting and processing blood and blood products are well known, one of skill in the art would readily recognize that given the teachings provided herein, that a variety of devices that fulfill the needs set forth above may be readily designed or existing devices modified. Accordingly, as such devices and methods are not limited by the specific embodiments set forth herein, but would include any device or methodology capable of maintaining sterility and which maintains blood in a fluid form in which complement activation is reduced and wherein components necessary for T cell activation (e.g., anti-CD3 and anti-CD28 antibodies or ligands thereto) may be immobilized or separated from the blood or blood product prior to administration to the subject. Further, as those of ordinary skill in the art can readily appreciate a variety of blood products can be utilized in conjunction with the devices and methods described herein. For example, the methods and devices could be used to provide rapid activation of T cells from cryopreserved whole blood, peripheral blood mononuclear cells, other cyropreserved blood-derived cells, or cryopreserved T cell lines upon thaw and prior to subject administration. In another example, the methods and devices can be used to boost the activity of a previously ex vivo expanded T cell product or T cell line prior to administration to the subject, thus providing a highly activated T cell product. Lastly, as will be readily appreciated the methods and devices above may be utilized for autologous or allogeneic cell therapy simultaneously with the subject and donor.

The methods of the present invention may also be utilized with vaccines to enhance reactivity of the antigen and enhance in vivo effect. In one embodiment, the compositions of the present invention are administered to a patient in conjunction with a composition that enhances T cells in vivo, for example, IL-2, IL-4, IL-7, IL-10, IL-12, and IL-15. Further, given that T cells expanded by the present invention have a relatively long half-life in the body, these cells could act as perfect vehicles for gene therapy, by carrying a desired nucleic acid sequence of interest and potentially homing to sites of cancer, disease, or infection. Accordingly, the cells expanded by the present invention may be delivered to a patient in combination with a vaccine, one or more cytokines, one or more therapeutic antibodies, etc. Virtually any therapy that would benefit by a more robust T cell population is within the context of the methods of use described herein.

A variety of in vitro and animal models exist for testing and validating the cell compositions of the present invention and their applicability to a particular immune system related disease or indication. Accordingly, one of ordinary skill in the art could easily choose the appropriate model from those currently existing in the art. Such models include the use of NOD mice, where IDDM results from a spontaneous T cell dependent autoimmune destruction of insulin-producing pancreatic β cells that intensifies with age (Bottazzo et al., *J. Engl. J. Med.*, 113:353, 1985; Miyazaki et al., *Clin. Exp. Immunol.*, 60:622, 1985). In NOD mice, a model of human IDDM, therapeutic strategies that target T cells have been successful in preventing IDDM (Makino et al., *Exp. Anim.*, 29:1, 1980). These include neonatal thymectomy, administration of cyclosporine, and infusion of anti-pan T cell, anti-CD4, or anti-CD25 (IL-2R) monoclonal antibodies (mAbs) (Tarui et al., Insulitis and Type I Diabetes Lessons from the NOD Mouse, Academic Press, Tokyo, p. 143, 1986). Other models include, for example, those typically utilized for autoimmune and inflammatory disease, such as multiple sclerosis (EAE model), rheumatoid arthritis, graft-versus-host disease (transplantation models for studying graft rejection using skin graft, heart transplant, islet of Langerhans transplants, large and small intestine transplants, and the like), asthma models, systemic lupus erythematosus (systemic autoimmunity—lpr or NZBx NZWF$_1$ models), and the like. (see, for example, Takakura et al., *Exp. Hematol.* 27(12):1815-821, 1999; Hu et al., *Immunology* 98(3):379-385, 1999; Blyth et al., *Am. J. Respir. Cell Mol. Biol.* 14(5):425-438, 1996; Theofilopoulos and Dixon, *Adv. Immunol.* 37:269-389, 1985; Eisenberg et al., *J. Immunol.* 125:1032-1036, 1980; Bonneville et al., *Nature* 344:163-165, 1990; Dent et al., *Nature* 343:714-719, 1990; Todd et al., *Nature* 351:542-547, 1991; Watanabe et al., *Biochem Genet.* 29:325-335, 1991; Morris et al., *Clin. Immunol. Immunopathol.* 57:263-273, 1990; Takahashi et al., *Cell* 76:969-976, 1994; Current Protocols in Immunology, Richard Coico (Ed.), John Wiley & Sons, Inc., Chapter 15, 1998).

Collagen-induced arthritis (CIA) is a T cell dependent animal model of rheumatoid arthritis (RA) (D. E. Trentham et al., "Autoimmunity to Type II Collagen: An Experimental Model of Arthritis," J. Exp. Med. 146: 857-868 (1977)). Within two weeks after immunization with type II collagen (CII) in IFA, susceptible rats develop polyarthritis with histologic changes of pannus formation and bone/cartilage erosion. In addition, humoral and cellular responses to CII occur in CIA as well as RA (E. Brahn, "Animal Models of Rheumatoid Arthritis: Clues to Etiology and Treatment" in Clinical Orthopedics and Related Research (B. Hahn, ed., Philadelphia, JB Lippincott Company, 1991). Consequently, CIA is a useful animal model of RA that serves as an in vivo system for the investigation of potentially new therapeutic interventions as described in the present invention.

Pharmaceutical Compositions

T cell populations of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration. The present invention further provides for pharmaceutical compositions comprising sensitizing compositions as described herein.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials. When "an immunologically effective amount" or "therapeutic amount" is indicated, the precise amount of the compositions of the present invention to be administered can be determined by a physician with consideration of individual differences in age, weight, disease severity and condition of the patient and any other factors relevant to treatment of the patient. It can generally be stated that a pharmaceutical composition comprising the subject T or B cells, may be administered at a dosage of $10^4$ to $10^7$ APC/kg body weight, preferably $10^5$ to $10^6$ APC/kg body weight, including all integer values within those ranges. Cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain adoptive immunotherapy studies, T cells are administered approximately at $1\times10^9$ to $2\times10^{11}$ cells to the patient. (See, e.g., U.S. Pat. No. 5,057,423). In some aspects of the present invention, particularly in the use of allogeneic or xenogeneic cells, lower numbers of cells, in the range of $10^6$/kilogram ($10^6$-$10^{11}$ per patient) may be administered. In certain embodiments, T or B cells are administered at $1\times10^5$, $1\times10^6$, $1\times10^7$, $1\times10^8$, $5\times10^8$, $1\times10^9$, $5\times10^9$, $1\times10^{10}$, $5\times10^{10}$, $1\times10^{11}$, $5\times10^{11}$, or $1\times10^{12}$ cells to the subject. T or B cell compositions may be administered multiple times at dosages within these ranges. The T or B cells may be autologous or heterologous (allogeneic or xenogeneic) to the patient undergoing therapy. If desired, the treatment may also include administration of mitogens (e.g., PHA) or lymphokines, cytokines, and/or chemokines (e.g., GM-CSF, IL-4, IL-13, Flt3-L, RANTES, MIP1α, etc.) as described herein to enhance restoration of the immune response.

The present invention also provides methods for preventing, inhibiting, or reducing the severity of autoimmune disease in an animal, which comprise administering to an animal an effective amount of the subject activated polyclonal T cells that have been cleared of undesired subpopulations of autoreactive T cells. The T cell compositions of the present invention can be administered in conjunction with T cell ablative therapy and/or other therapies for the treatment of autoimmune diseases.

The present invention also provides methods for preventing, inhibiting, or reducing the severity of graft-versus-host disease in an animal requiring a hematopoietic stem cell transplant, which comprise administering to an animal an effective amount of the subject donor bone marrow that has been cleared of undesired subpopulations of alloreactive T cells. The compositions of the present invention can be administered in conjunction with other therapies for the treatment of immune defects associated with hematopoietic stem cell transplantation.

The present invention also provides methods for preventing, inhibiting, or reducing the severity of host-versus-graft disease or graft rejection in an animal requiring an organ transplant, which comprise administering to an animal an effective amount of the subject T cell compositions that has been cleared of undesired subpopulations of alloreactive T cells. The compositions of the present invention can be administered in conjunction with other therapies for the treatment of immune defects associated with organ transplantation.

One aspect of the present invention is to administer activated and expanded T cells that proliferate and grow rapidly in vivo. Without being bound by theory, the infused T cells may suppress in vivo homeostatic T cell proliferation and prevent unwanted T cells from proliferating in vivo, for example cancer cells, autoreactive T cells, alloreactive T cells, HIV infected T cells, and the like (see King, et al., 2004, Cell 117:265-277). Accordingly, the compositions described herein comprising T cells that have been cultured so as to delete at least a substantial portion of unwanted cells can be infused into a patient. The infused cells then prevent homeostatic proliferation and therefore, prevent unwanted cells from regenerating in vivo.

The administration of the subject pharmaceutical compositions may be carried out in any convenient manner, including by aerosol inhalation, injection, ingestion, transfusion, implantation or transplantation. The compositions of the present invention may be administered to a patient subcutaneously, intradermally, intramuscularly, by intravenous (i.v.) injection, intratumorally, or intraperitoneally. Preferably, the T cell compositions of the present invention are administered by i.v. injection. The compositions of activated T cells may be injected directly into a tumor or lymph node.

In yet another embodiment, the pharmaceutical composition can be delivered in a controlled release system. In one embodiment, a pump may be used (see Langer, 1990, *Science* 249:1527-1533; Sefton 1987, *CRC Crit. Ref. Biomed. Eng.* 14:201; Buchwald et al., 1980; *Surgery* 88:507; Saudek et al., 1989, *N. Engl. J. Med.* 321:574). In another embodiment, polymeric materials can be used (see Medical Applications of Controlled Release, 1974, Langer and Wise (eds.), CRC Pres., Boca Raton, Fla.; Controlled Drug Bioavailability, Drug Product Design and Performance, 1984, Smolen and Ball (eds.), Wiley, New York; Ranger and Peppas, 1983; *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105). In yet another embodiment, a controlled release system can be placed in proximity of the therapeutic target, thus requiring only a fraction of the systemic dose (see, e.g., Medical Applications of Controlled Release, 1984, Langer and Wise (eds.), CRC Pres., Boca Raton, Fla., vol. 2, pp. 115-138).

The T cell and/or sensitizing composition compositions of the present invention may also be administered using any number of matrices. Matrices have been utilized for a number of years within the context of tissue engineering (see, e.g., Principles of Tissue Engineering (Lanza, Langer, and Chick (eds.)), 1997. The present invention utilizes such matrices within the novel context of acting as an artificial lymphoid organ to support, maintain, or modulate the immune system, typically through modulation of T cells. Accordingly, the present invention can utilize those matrix compositions and formulations which have demonstrated utility in tissue engineering. Accordingly, the type of matrix that may be used in the compositions, devices and methods of the invention is virtually limitless and may include both biological and synthetic matrices. In one particular example, the compositions and devices set forth by U.S. Pat. Nos. 5,980,889; 5,913,998; 5,902,745; 5,843,069; 5,787,900; or 5,626,561 are utilized. Matrices comprise features commonly associated with being biocompatible when administered to a mammalian host. Matrices may be formed from both natural and synthetic materials. The matrices may be non-biodegradable in instances where it is desirable to leave permanent structures or removable structures in the body of an animal, such as an implant; or biodegradable. The matrices may take the form of sponges, implants, tubes, telfa pads, fibers, hollow fibers, lyophilized components, gels, powders, porous compositions, liposomes, cells, or nanoparticles. In addition, matrices can be designed to allow for sustained release of seeded cells or produced cytokine or other active agent. In certain embodiments, the matrix of the present invention is flexible and elastic, and may be described as a semisolid scaffold that is permeable to substances such as inorganic salts, aqueous fluids and dissolved gaseous agents including oxygen.

A matrix is used herein as an example of a biocompatible substance. However, the current invention is not limited to matrices and thus, wherever the term matrix or matrices appears these terms should be read to include devices and other substances which allow for cellular retention or cellular traversal, are biocompatible, and are capable of allowing traversal of macromolecules either directly through the substance such that the substance itself is a semi-permeable membrane or used in conjunction with a particular semi-permeable substance.

All references referred to within the text are hereby incorporated by reference in their entirety. Moreover, all numerical ranges utilized herein explicitly include all integer values within the range and selection of specific numerical values within the range is contemplated depending on the particular use. Further, the following examples are offered by way of illustration, and not by way of limitation.

Example 1

Deletion of Antigen-Specific T Cells Following Restimulation with CD3/CD28 XCELLERATE™ Beads This example describes the elimination of antigen-specific T cells from a mixed population of cells by restimulation with anti CD3/CD28 XCELLERATE™ beads (3×28 beads). The generation of XCELLERATED T Cells™ using the processes described herein is essentially as described in U.S. patent application Ser. No. 10/133,236.

Human PBMC were screened for HLA-A2 CMVpp65 positivity by flow cytometry using HLA-A2 tetramers loaded with CMVpp65 peptide (HLA-A2-CMVpp65). Approximately 3% of the CD3+CD8+ T cells in the donor selected expressed TCR specific for HLA-A2-CMVpp65 (FIG. 1).

PBMC from the donor (donor 2) and control donor (donor 1) were activated with CMV antigen coated onto paramagnetic beads and by day 10 of culture, many cells were shown by flow cytometric analysis to be CD25 (IL-2R) positive, and all of the HLA-A2 CMVpp65+ T cells expressed high levels of CD25, indicating activation (FIG. 2, right panel).

At day 14 post-primary stimulation, cultures were then either left unstimulated (FIG. 3, panels A1-A4) or were restimulated using the XCELLERATE™ process with 3×28 beads for 16 hours (FIG. 3, panels B1-B4). As shown in FIG. 3, CD25 is upregulated on restimulated cells (panel B2), but tetramer-positive (i.e., CMVpp65-Ag-specific) prestimulated cells were deleted by the secondary strong stimulation provided by the 3×28 beads (panels B3 and B4), while the other cells were unaffected. Similar results were observed when cells were attached to beads or associated with cells attached to beads, magnetically selected and placed back into culture prior to restimulation with the 3×28 beads. In an additional study, the cells were restimulated for an additional 4 days. Deletion of the tetramer-positive cells was still observed after 4 additional days in the 3×28 restimulated cultures.

These results demonstrate that activated CMVpp65-antigen-specific T cells that are restimulated with 3×28 beads are eliminated from the population of cells, most likely through apoptosis.

Example 2

Determination of Apoptosis

This example describes an illustrative assay for measuring apoptosis.

DNA Fragmentation Assay

Cells are lysed in 50 µl of lysis buffer (10 mM EDTA, 50 mM Tris pH 8, 0.5% sodium dodecyl sulfate, 0.5 mg/ml proteinase K). RNAse A (0.5 mg/ml) is added and lysates are incubated for 1 hr. at 37° C. Two phenol extraction (equal volumes) are performed, followed by one chloroform extraction. DNA is precipitated with two volumes of ice-cold ethanol and incubated at −80° C. for 1 hr. DNA is pelleted by centrifugation at 14,000 rpm for 10 minutes at 4° C. Pellets are air-dried for 30 minutes, resuspended in 50 µl of Tris-EDTA pH 8. DNA is electrophoresed in a 1.8% agarose gel in 1×TBE running buffer (0.05 M Tris base, 0.05 M boric acid, 1 mM disodium EDTA), according to the methods of Preston, et al., Cancer Res., 1994, 54, 4214-4223.

Example 3

Induction of Apoptosis in B-Cells by Coculture with XCELLERATED T Cells™

This example describes the deletion of leukemic B-cells in B-CLL patient samples by co-culture with XCELLERATED T Cells™.

Figures 5A, 5B:
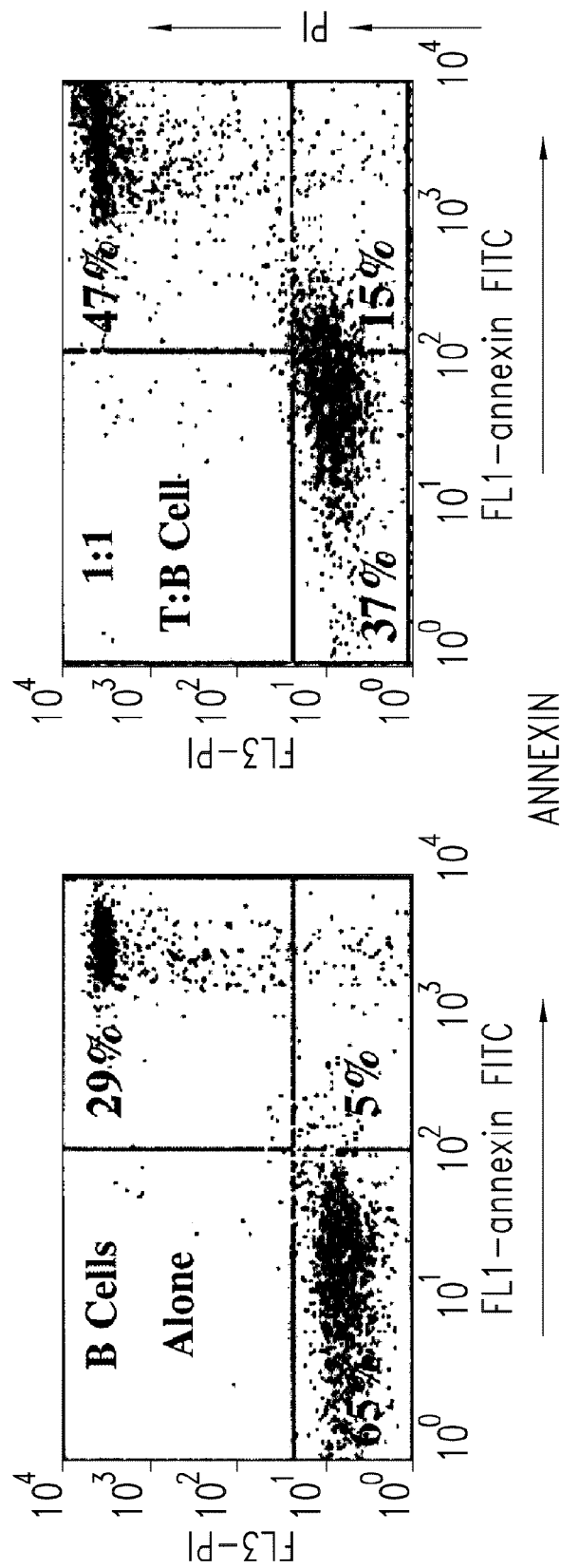
FIG. 5 is a dot plot showing the induction of apoptosis in leukemic B-cells co-cultured with XCELLERATED T Cells™.
Figures 5C, 5D:
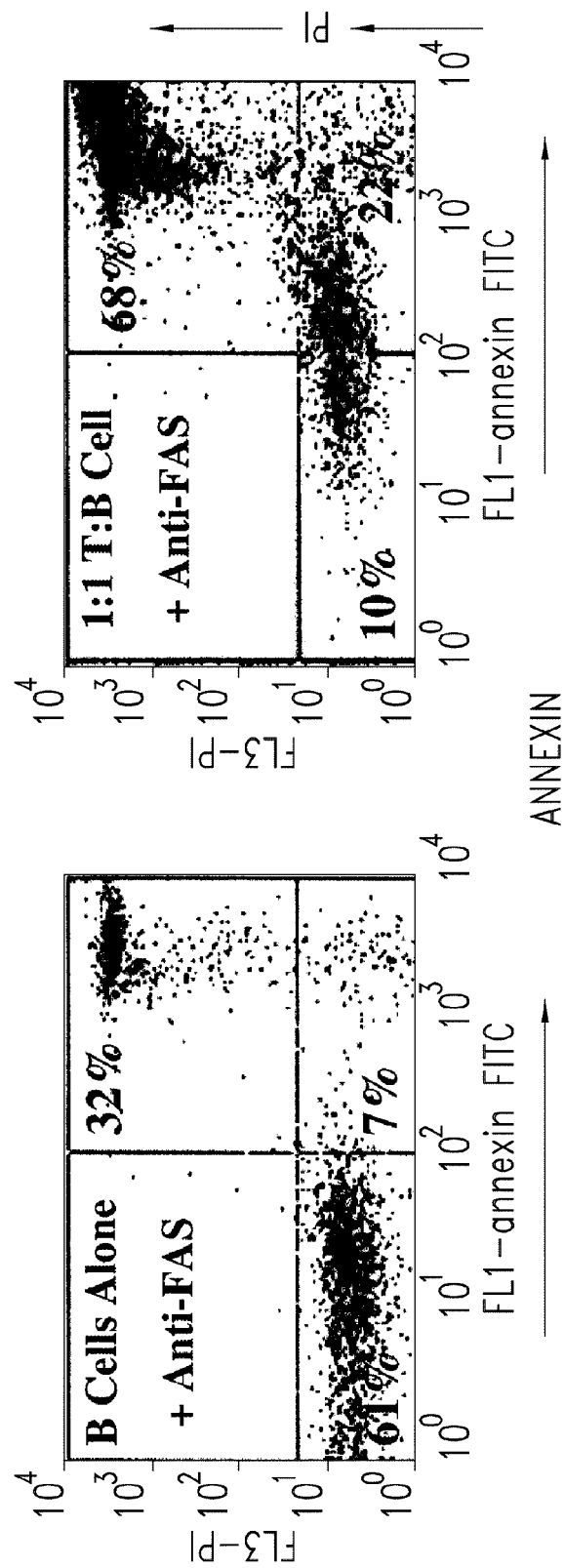
Figure 6:
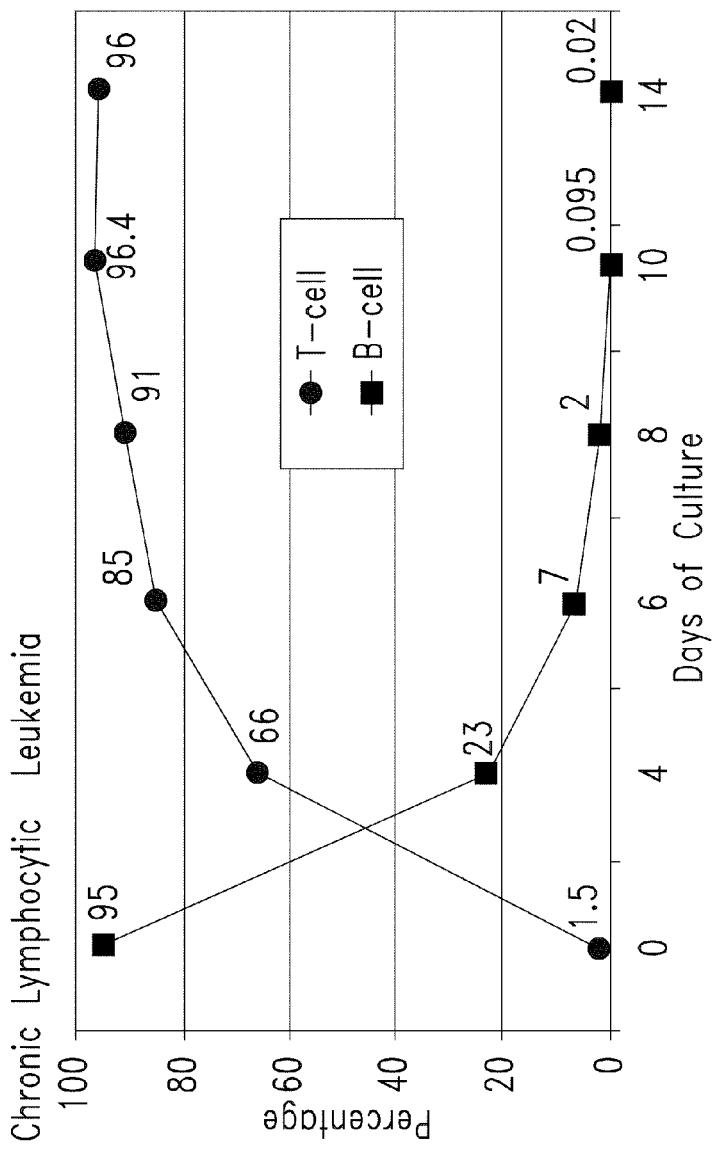
FIG. 6 is a graph showing the disappearance of leukemic B-cells during the XCELLERATE™ process and the concomitant expansion of T cells.

XCELLERATED T Cells™, generated essentially as described in U.S. patent application Ser. No. 10/133,236, were co-cultured with unmanipulated autologous leukemic cells from B-CLL patients. Cell surface markers for CD54, CD80, CD95 (FAS) and CD86, and Annexin/PI (apoptosis) were measured at 24 and 48 hours by flow cytometry. XCELLERATED T Cells™ were shown to drive up expression of CD95 (FAS) on leukemic B cells (FIG. 4). After 48 hours of co-culture with day 12 XCELLERATED T Cells™, autologous leukemic B cells show increased expression of CD95 and sensitivity to anti-FAS as measured by flow cytometry (FIG. 5). As shown in FIG. 5, addition of anti-FAS antibody to co-cultured T:B cells led to increased apoptosis in the leukemic B-cells. In an additional study, it was shown that T cells grow whereas leukemic B-cells are eliminated during the XCELLERATE™ process (FIG. 6).

In summary, XCELLERATED T Cells™ upregulate important effector molecules on leukemic B cells, induce functional FAS on leukemic B-cells, and can drive leukemic B-cells into apoptosis pathways. Leukemic B cells were virtually undetectable by the end of the XCELLERATE™ process. Therefore, XCELLERATED T Cells™ can be used as a sensitizing composition or a pro-apoptotic composition for the elimination of leukemic B-cells from a mixed population of cells.

Example 4

Varying Bead:Cell Ratios can Selectively Expand or Delete Memory CD8 T Cells

This example shows that the bead:cell ratio can have a profound effect on expansion of different populations of T cells. In particular, a high bead:cell ratio (3:1-10:1) tends to induce death in antigen-specific T cells while a lower bead:cell ratio (1:1-1:10) leads to expansion of antigen-specific T cells. Further, the data described below show that lower bead:cell ratios lead to improved cell expansion in polyclonal cell populations as well. Thus, this example shows that lower bead:cell ratios improve overall cell expansion. Further, this example demonstrates that at high bead:cell ratios, the beads described herein can be used as pro-apoptotic compositions.

Cells were prepared and stimulated using the XCELLERATE I™ process essentially as described in U.S. patent application Ser. No. 10/187,467 filed Jun. 28, 2002. Briefly, in this process, the XCELLERATED T Cells™ are manufactured from a peripheral blood mononuclear cell (PBMC) apheresis product. After collection from the patient at the clinical site, the PBMC apheresis are washed and cryopreserved. Cells were then thawed, and placed in culture @37° C./5% $CO_2$ for 1 hour to allow monocytes and other adherent cells to bind to the culture plate. Non-adherent cells were transferred to new culture plates for stimulation as follows. Following this monocyte-depletion step, a volume containing a total of $5\times10^8$ CD3$^+$ T cells is taken and set-up with $1.5\times10^9$ DYNABEADS® M-450 CD3/CD28 T to initiate the XCELLERATE™ process (approx. 3:1 beads to T cells). The mixture of cells and DYNABEADS® M-450 CD3/CD28 T are then incubated at 37° C., 5% $CO_2$ for approximately 8 days to generate XCELLERATED T Cells™ for a first infusion. The remaining monocyte-depleted PBMC are cryopreserved until a second or further cell product expansion (approximately 21 days later) at which time they are thawed, washed and then a volume containing a total of $5\times10^8$ CD3$^+$ T cells is taken and set-up with $1.5\times10^9$ DYNABEADS® M-450 CD3/CD28 T to initiate the XCELLERATE™ Process for a second infusion. During the incubation period of ≈8 days at 37° C., 5% $CO_2$, the CD3$^+$ T cells activate and expand. The anti-CD3 mAb used is BC3 (XR-CD3; Fred Hutchinson Cancer Research Center, Seattle, Wash.), and the anti-CD28 mAb (B-T3, XR-CD28) is obtained from Diaclone, Besançon, France.

For the experiment described below, cultures containing cells for which adherent cells had been removed then have beads added at bead:T cell ratios as shown in Table 1. The beads used in this Example comprised the DYNABEADS® M-450 CD3/CD28 T with a 1:1 CD3:CD28 antibody ratio bound on the beads.

TABLE 1

Varying Bead:Cell Ratios can Selectively
Expand or Delete Memory CD8 T cells

| Bead:Cell Ratio | Fold Increase | |
|---|---|---|
| | Polyclonal T cells | CMV Antigen-Specific T cells |
| 10:1 | 149 | 0 |
| 5:1 | 294 | 0 |
| 3:1 | 346 | 1.4 |
| 1:1 | 562 | 20.6 |
| 1:5 | 113 | 53 |
| 1:10 | 79 | 45.8 |

Figure 7:
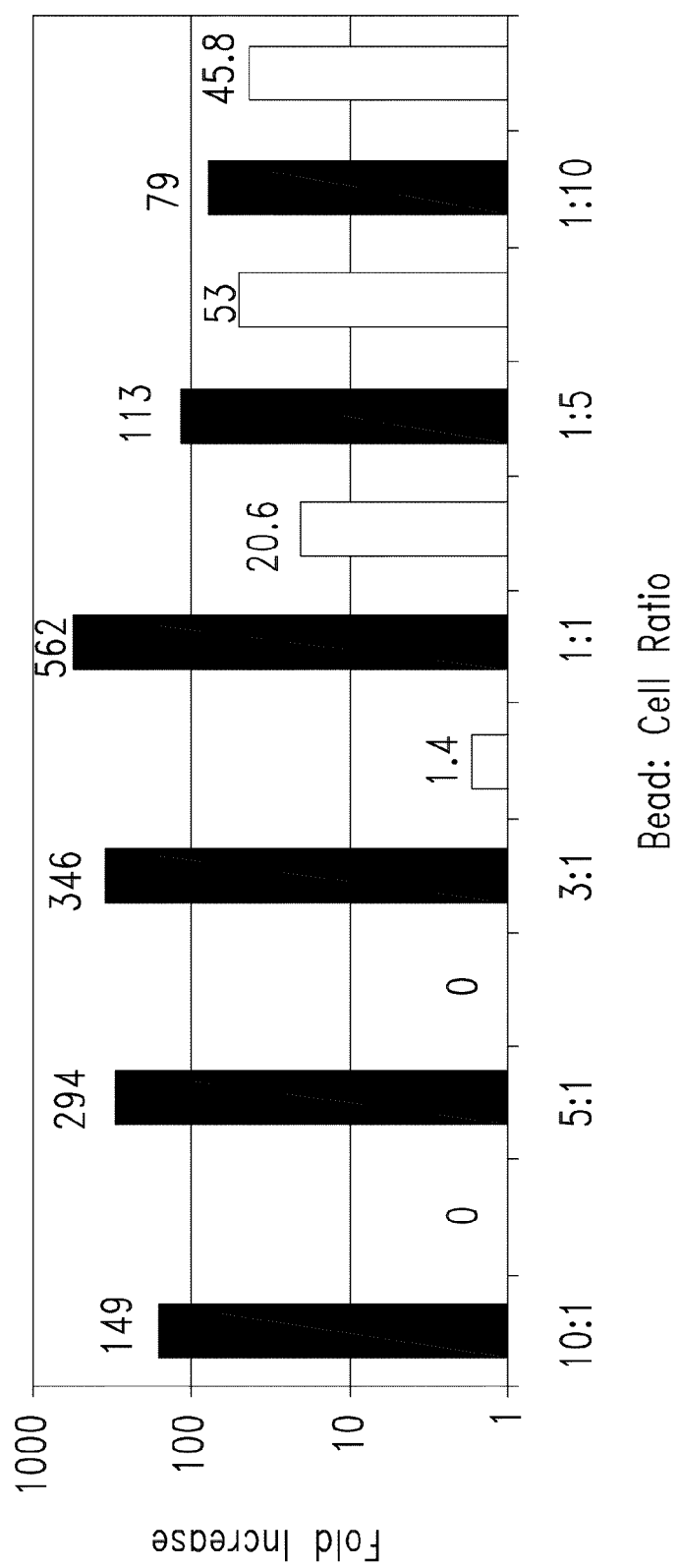
FIG. 7 is a graph comparing fold increase of polyclonal T cells to the fold increase of CMV pp65 A2-tetramer+ (antigen-specific) T cells using varying bead:cell ratios. Solid bars represent polyclonal T cells. Striped bars represent CMV-specific T cells.

The results summarized in Table 1 and shown graphically in FIG. 7 demonstrate that antigen-specific T cells can be selectively deleted by using high bead:cell ratios and expanded using low bead:cell ratios. Similar results were observed with EBV-specific CD8$^+$ T cells and influenza-specific CD8$^+$ T cells and CD4$^+$ T cells (not shown). Without being bound by theory, it is thought that the antigen-specific T cells are sensitized to further stimulation. Stimulation with high bead:cell ratios provides a high concentration of stimulating antibody, leading to over-stimulation of antigen-specific T cells, causing them to die, either by apoptosis or other mechanisms. Thus, in this regard, the beads are functioning as a pro-apoptotic composition. Using lower bead:cell ratios provides a stimulation signal to antigen-specific T cells that does not over-stimulate, but rather induces rapid proliferation of these cells. An increase in proliferation is also observed in the polyclonal population of T cells using lower bead:cell ratios. In particular, the results indicate that a bead:cell ratio of 1:1 is optimal for polyclonal T cell expansion.

Therefore, in this Example, evidence is provided to support the use of differing bead:cell ratios depending on the outcome desired. For expansion of antigen-specific T cells, a lower bead:cell ratio is preferable. If deletion of antigen-specific T cells is the desired outcome, a higher bead:cell ratio is preferable.

Example 5

Deletion of Allo-Reactive T Cells Following Restimulation with CD3/CD28 XCELLERATE™ Beads This example describes the deletion of allo-reactive T cells following restimulation with CD3/CD28 XCELLERATE™ beads.

PBMC were stimulated for 3 days with either allogeneic PBMC or the JY B-lymphoblastoid allogeneic cell line. On day 3, the allogeneic PBMC- or JY-stimulated PBMC were then cultured with CD3/CD28 beads using the XCELLERATE™ process essentially as described in U.S. patent application Ser. No. 10/350,305, with and without 30 minute positive selection with CD3/CD28 beads. Following the XCELLERATE™ process, the cells were then restimulated with either allogeneic PBMC or JY allogeneic antigen and CD25 up-regulation was measured. Restimulation with allogeneic cells following the XCELLERATE™ process did not lead to upregulation of CD25 expression (measured using flow cytometric analysis), indicating that the allo-reactive cells had been deleted. In particular, positive selection of JY stimulated CD8+ T cells during the XCELLERATE™ process significantly decreased allo-reactivity. However, the T cells remained competent to respond to irrelevant antigens in XCELLERATED™ cultures as demonstrated by 3rd party allogeneic PBMC and JY responses (e.g., restimulation of JY-stimulated culture with allogeneic PBMC or restimulation of allo-PBMC-stimulated culture with JY).

Thus, these results show that activated allo-reactive T cells are deleted by restimulation with CD3/CD28 beads while the remaining polyclonal T cells can be expanded exponentially for use in any number of immunotherapeutic applications.

Example 6

Restoration of T Cell Repertoire in Patients with Autoimmune Disease

T cells from patients with autoimmune disease were expanded using the XCELLERATE™ process and T cell repertoire observed by spectratype analysis.

Figure 8A:
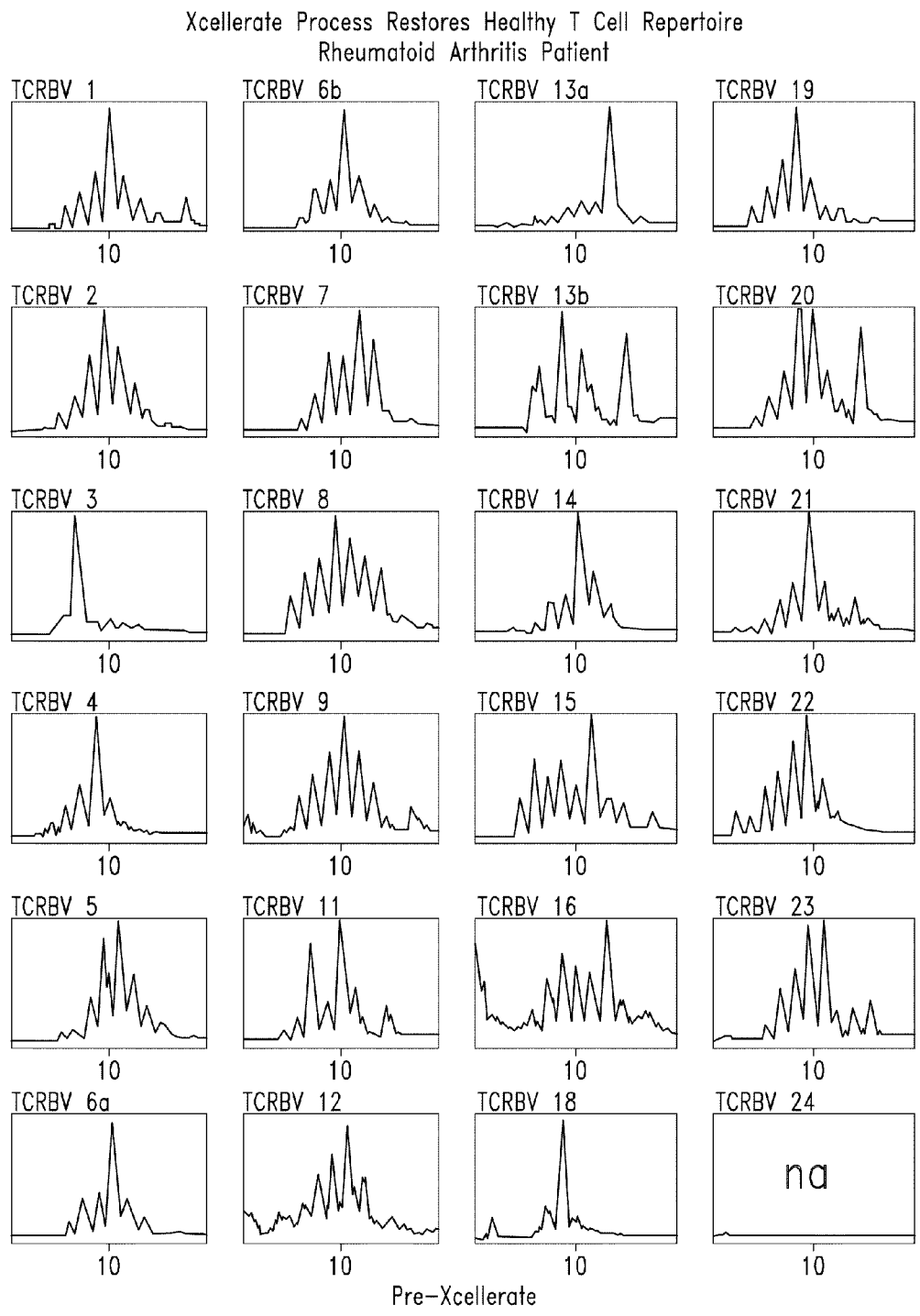
FIG. 8 shows the spectratype analysis of T cells from a rheumatoid arthritis patient pre-XCELLERATE™ (left panels) and post-XCELLERATE™ (right panels) (5:1 bead:T cell ratio). Restoration of healthy T cell repertoire was observed (see in particular TCRBV 13a and TCRBV 3 panels, pre and post XCELLERATE™).
Figure 8B:
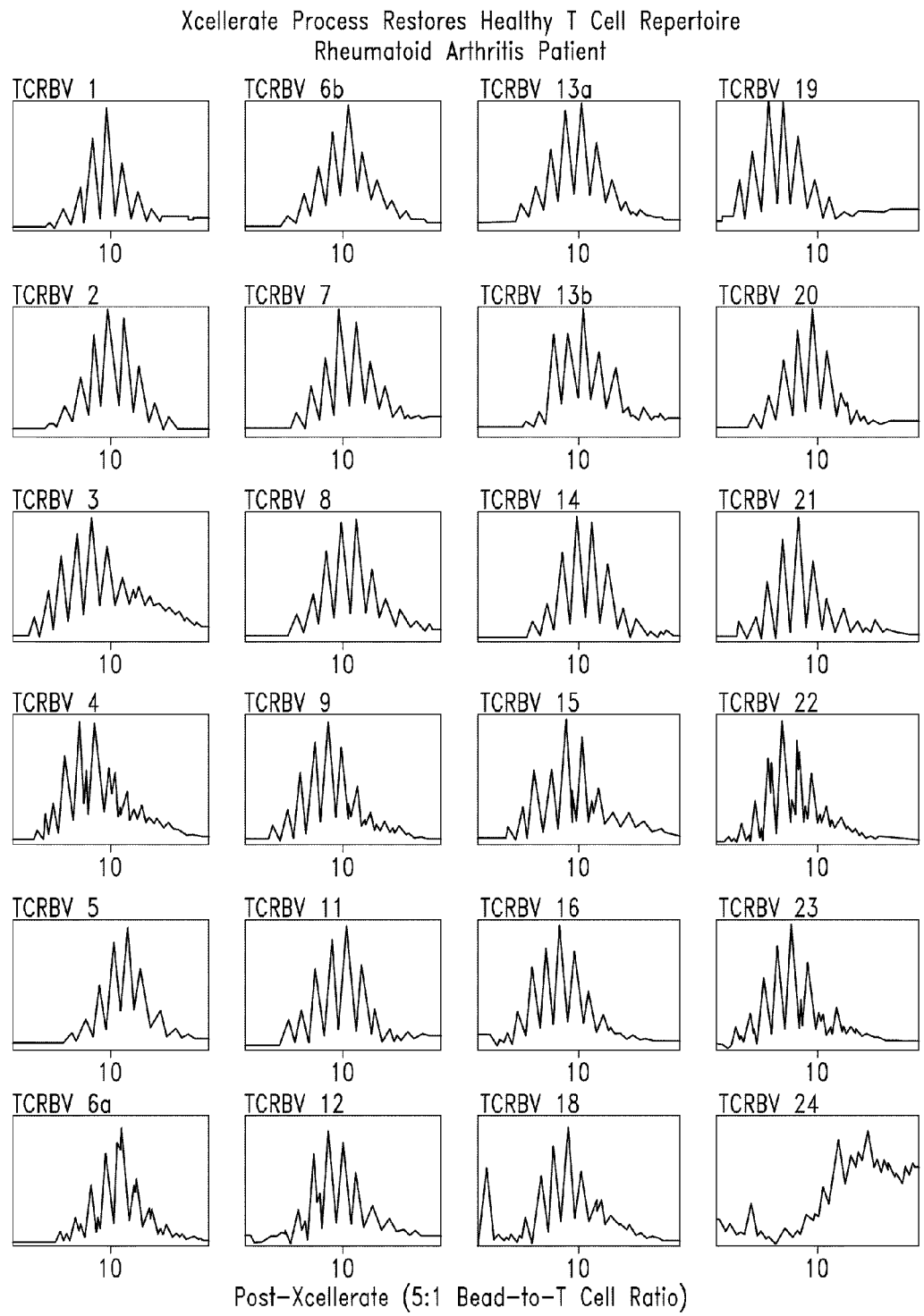

Samples from patients with systemic lupus erythematosus, rheumatoid arthritis, scleroderma, Crohn's disease, and psoriatic arthritis were analyzed. Total T cell expansion in these patients (n=9) using the XCELLERATE™ process was similar to that observed in normal donors (as seen in FIG. 7) using bead:T cell ratios from 1:5 to 5:1. Further study of T cells from patients with rheumatoid arthritis, psoriatic arthritis, and Crohn's disease using spectratype analysis showed that a healthy T cell repertoire is restored following the XCELLERATE™ process (5:1 bead:T cell ratio) (Representative sample from a patient with rheumatoid arthritis is shown in FIG. 8. Similar results were observed in a patient with psoriatic arthritis and a Crohn's disease patient (not shown)). Further analysis showed that XCELLERATED™ T cells from these patients exhibit a Th1 phenotype (see FIG. 9).

In summary, in autoimmune disease patients, the XCELLERATE™ process can be used to expand T cells more than one thousand fold, restore a broad T cell repertoire and generate a Th1-type T cell population.

Example 7

Figure 10:
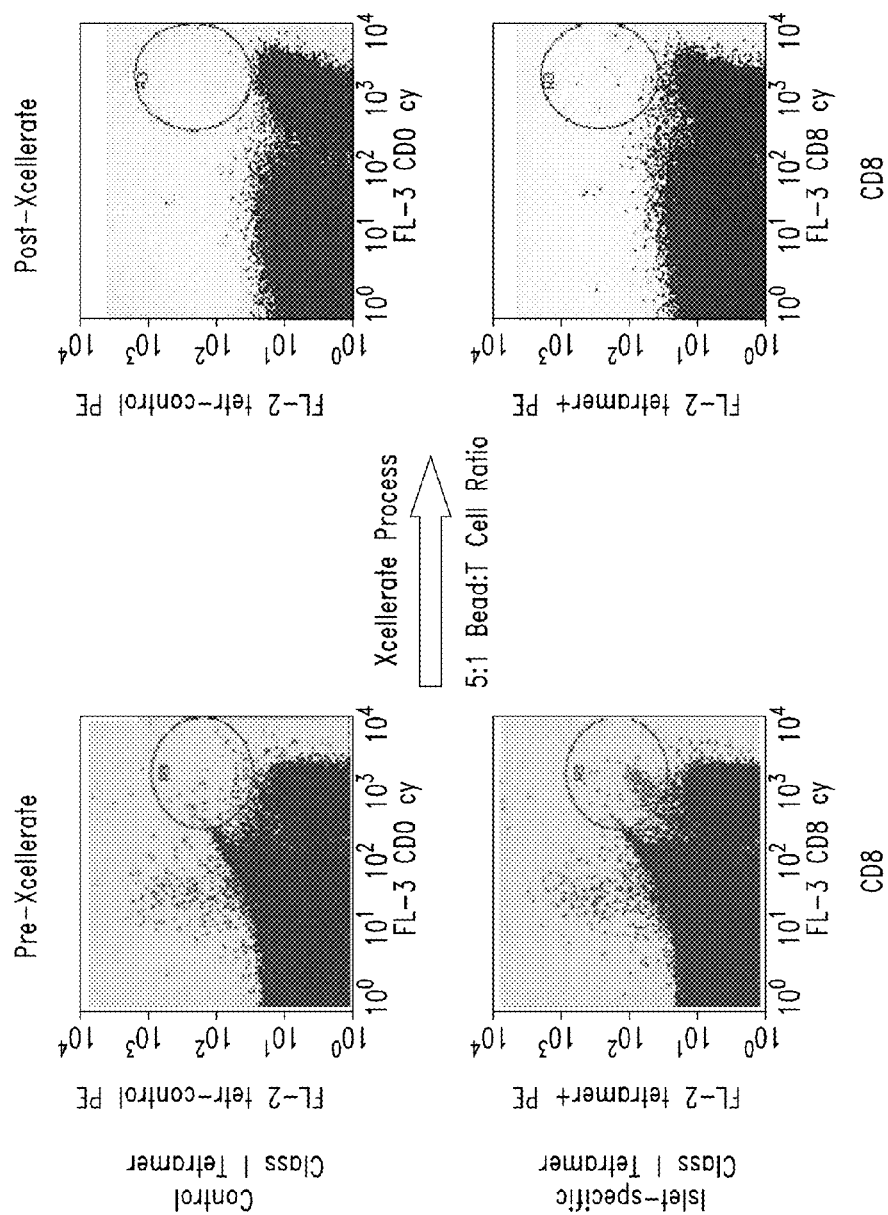
FIG. 10 is a 4 panel dot plot showing the deletion of islet-specific CD8+ autoreactive T cells in a mouse diabetes model. Islet-specific T cells were detected using flow cytometry and MHC-class I tetramer staining.

High Bead:T Cell Ratio Deletes Autoreactive CD8+ T Cells in a Mouse Diabetes Model In a related experiment, the XCELLERATE™ process (5:1 bead:T cell ratio) was used to expand T cells in a mouse diabetes model. Cells were expanded using the XCELLERATE™ process and further analyzed using an islet-specific MHC Class I tetramer. The results shown in FIG. 10 demonstrate that the autoreactive CD8+ T cells were deleted.

In summary, using a pre-clinical mouse diabetes model, the XCELLERATE™ process eliminated autoreactive CD8+ T cells.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for eliminating at least a substantial portion of a clonal antigen-specific memory T cell subpopulation from a mixed population of T cells from an individual, comprising,
exposing a population of cells comprising the mixed population of T cells to a surface,
said exposure comprising contacting said population of cells with said surface at a ratio of surface to cells of at least 5:1, wherein the surface has attached thereto an anti-CD3 antibody and an anti-CD28 antibody, or antigen-binding fragments thereof; and wherein said exposure results in apoptosis or growth inhibition in at least a substantial portion of at least one clonal antigen-specific memory T cell population present in the mixed population of T cells without requiring further activation or stimulation;
thereby eliminating at least a substantial portion of said clonal antigen-specific memory T cell population from the mixed population of T cells.

2. The method of claim 1 further comprising expanding the remaining mixed population of T cells.

3. The method of claim 2 wherein the remaining mixed population of cells is expanded by further exposing the remaining mixed population of cells to the surface; wherein the ratio of surface to cells is from about 1:1 to about 1:10, thereby stimulating and expanding said remaining T cells.

4. The method of claim 3 wherein the exposure of said cells to said surface is for a time sufficient to increase polyclonality.

5. The method of claim 4 wherein the increase comprises a shift from mono to oligoclonality or to polyclonality of the T cell population as measured by a Vβ, Vα, Vγ, or Vδ spectratype profile of at least one Vβ, Vα, Vγ, or Vδ family gene.

6. The method of claim 1 or claim 3 wherein the surface is a paramagnetic bead.

* * * * *

UNITED STATES PATENT AND TRADEMARK OFFICE
CERTIFICATE OF CORRECTION

| | | |
|---|---|---|
| PATENT NO. | : 8,617,884 B2 | Page 1 of 1 |
| APPLICATION NO. | : 12/324593 | |
| DATED | : December 31, 2013 | |
| INVENTOR(S) | : Ronald Berenson, Mark Bonyhadi and Dale Kalamasz | |

It is certified that error appears in the above-identified patent and that said Letters Patent is hereby corrected as shown below:

Title page, Related U.S. Application Data should read item (63) Continuation of application No. 10/900,046, filed on Jul. 27, 2004, now abandoned, which is a continuation-in-part of application No. 10/729,822, filed on Dec. 5, 2003, now abandoned, which is a continuation-in-part of application No. 10/603,577, filed on Jun. 24, 2003, now abandoned.

item (60) Provisional application No. 60/442,001, filed on Jan 22, 2003; Provisional application No. 60/431,212, filed on Dec. 4, 2002; Provisional application 60/393,042, filed Jun. 28, 2002

In the Specification

Column 1 line 6 should read     CROSS-REFERENCE TO RELATED
                                APPLICATIONS This application is a continuation of U.S. patent application Ser. No. 10/900,046, filed Jul. 27, 2004, now abandoned, which application is a continuation-in-part of U.S. patent application Ser. No. 10/729,822, filed Dec. 5, 2003, now abandoned, which application is a continuation-in-part of U.S. patent application Ser. No. 10/603,577, filed Jun. 24, 2003, now abandoned, and which claims the benefit under 35 U.S.C. §119(3) of U.S. Provisional Patent Application No. 60/442,001, filed Jan. 22, 2003, now expired, U.S. Provisional Patent Application No. 60/431,212, filed December 4, 2002, now expired, and U.S. Provisional Patent Application No. 60/393,042, filed June 28, 2002, now expired.

Signed and Sealed this
Sixteenth Day of September, 2014

Michelle K. Lee
*Deputy Director of the United States Patent and Trademark Office*